US011331383B2

(12) United States Patent
Abrams et al.

(10) Patent No.: US 11,331,383 B2
(45) Date of Patent: *May 17, 2022

(54) ATTENUATED AFRICAN SWINE FEVER VIRUS VACCINE

(71) Applicant: THE PIRBRIGHT INSTITUTE, Woking (GB)

(72) Inventors: Charles Abrams, Woking (GB); Ana-Luisa Reis, Woking (GB); Chris Netherton, Woking (GB); Linda Dixon, Woking (GB); Dave Chapman, Woking (GB); Pedro Sanchez-Cordon, Woking (GB)

(73) Assignee: THE PIRBRIGHT INSTITUTE, Woking (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/668,384

(22) Filed: Oct. 30, 2019

(65) Prior Publication Data

US 2020/0129609 A1 Apr. 30, 2020

Related U.S. Application Data

(63) Continuation of application No. 15/319,856, filed as application No. PCT/GB2015/051798 on Jun. 19, 2015, now Pat. No. 10,507,237.

(30) Foreign Application Priority Data

Jun. 19, 2014 (GB) .................................. 1410971

(51) Int. Cl.
*A61K 39/12* (2006.01)
*C12N 7/00* (2006.01)
*A61K 39/00* (2006.01)

(52) U.S. Cl.
CPC ................ *A61K 39/12* (2013.01); *C12N 7/00* (2013.01); *A61K 2039/5254* (2013.01);
(Continued)

(58) Field of Classification Search
None
See application file for complete search history.

(56) References Cited

U.S. PATENT DOCUMENTS 10,507,237 B2 12/2019 Abrams et al.
2002/0086427 A1 7/2002 Leiden et al.

FOREIGN PATENT DOCUMENTS

CN 103172749 A 6/2013
WO WO-2008/147799 A1 12/2008

OTHER PUBLICATIONS

Gerner et al. Identification of novel foot-and-mouth disease virus specific T-cell epitopes in c/c and d/d haplotype miniature swine. Virus Research. vol. 121, Issue 2, Nov. 2006, pp. 223-228 (Year: 2006).*

(Continued)

*Primary Examiner* — Michelle S Horning
(74) *Attorney, Agent, or Firm* — Marshall, Gerstein & Borun LLP

(57) ABSTRACT

The present invention provides an attenuated African Swine Fever (ASF) virus which lacks a functional version of the following genes:
   multigene-family 360 genes 9L, 10L, 11L, 12L, 13L and 14L; and
   multigene-family 505 genes 1R, 2R, 3R and 4R.
The invention further provides an attenuated African Swine Fever (ASF) virus which Lacks a functional version of the DP148R gene. The present invention also provides a vaccine comprising such an attenuated virus and its use to prevent
(Continued)

ASF. Further, the invention relates to intranasal administration of an attenuated ASF virus.

16 Claims, 46 Drawing Sheets

Specification includes a Sequence Listing.

(52) U.S. Cl.
CPC .. *A61K 2039/543* (2013.01); *A61K 2039/552* (2013.01); *C12N 2710/12021* (2013.01); *C12N 2710/12022* (2013.01); *C12N 2710/12034* (2013.01); *C12N 2710/12062* (2013.01)

(56) References Cited

OTHER PUBLICATIONS

De Leon et al. Laboratory methods to study African swine fever virus. Virus Research. vol. 173, Issue 1, Apr. 2013, pp. 168-179. (Year: 2013).*
Abrams et al., Sequential deletion of genes from the African swine fever virus genome using the cre/loxP recombination system, Virology, 433(1):142-8 (2012).
Afonso et al., African swine fever virus multigene family 360 and 530 genes affect host interferon response, J. Virol., 78(4):1858-64 (2004).
Alonso et al., African swine fever virus-specific cytotoxic T lymphocytes recognize the 32 kDa immediate early protein (vp32), Virus Res., 49(2):123-30 (1997).
Boinas et al., Characterization of pathogenic and non-pathogenic African swine fever virus isolates from Ornithodoros erraticus inhabiting pig premises in Portugal, J. Gen. Virol., 85(Pt. 8):2177-87 (2004).
Burrage et al., African Swine Fever Virus Multigene Family 360 Genes Affect Virus Replication and Generalization of Infection in *Ornithodoros porcinus* Ticks, Journal of Virology, 78(5):2445-2453 (2004).
Chapman et al., Comparison of the genome sequences of non-pathogenic and pathogenic African swine fever virus isolates, J. Gen. Virol., 89(Pt. 2):397-408 (2008).
Dixon et al., Prospects for development of African swine fever virus vaccines, Dev. Biol. (Basel), 135:147-57 (2013).
Escribano et al., Antibody-mediated neutralization of African swine fever virus: myths and facts, Virus Res., 173(1):101-9 (2013).
Galindo-Cardiel et al., Standardization of pathological investigations in the framework of experimental ASFV infections, Virus Res., 173(1):180-90 (2013).
Gerner et al., Identification of novel foot-and-mouth disease virus specific T-cell epitopes in c/c and d/d haplotype miniature swine, Virus Res., 121(2):223-8 (2006).
International Preliminary Report on Patentability, International Application No. PCT/GB2015/051798, dated Dec. 29, 2016.
International Search Report and Written Opinion, International Application No. PCT/GB2015/051798, dated Nov. 13, 2015.
King et al., Development of a TaqMan PGR assay with internal amplification control for the detection of African swine fever virus, J. Virol. Methods, 107(1):53-61 (2003).
King et al., Protection of European domestic pigs from virulent African isolates of African swine fever virus by experimental immunisation, Vaccine, 29(28):4593-600 (2011).
Neilan et al., Novel swine virulence determinant in the left variable region of the African swine fever virus genome, J. Virol., 76(7):3095-104 (2002).
Oura et al., In vivo depletion of CD8+ T lymphocytes abrogates protective immunity to African swine fever virus, J. Gen. Virol., 86 (Pt. 9):2445-50 (2005).
Piriou et al., Humoral and cell-mediated immune responses of d/d histocompatible pigs against classical swine fever (CSF) virus, Vet. Res., 34(4):389-404 (2003).
The Pig Site, downloaded from the Internet at: < http://www.thepigsite.com/pighealth/article/441/african-swine-fever-asf> (year).
Tulman et al., African swine fever virus, Curr. Top. Microbiol. Immunol., 328:43-87 (2009).
Ventura, Strategies of the African swine fever virus to manipulate innate immunity, Ph.D. in Biology Dissertation, Institute de Tecnologia Química e Biológica, Universidade Nova de Lisboa (Jun. 2012).
Zsak et al., African swine fever virus multigene family 360 and 530 genes are novel macrophage host range determinants, J. Virol., 75(7):3066-76 (2001).
Greig A. et al., "The excretion of two virulent strains of african swine fever virus by domestic pigs", JHyg Camb., Dec. 31, 1970, vol. 68, pp. 673-682.
Abrams C. A. et al., Deletion of virulence associated genes from attenuated African swine fever virus isolate Our T88/3 decreases its ability to protect against challenge with virulent virus, Virology, vol. 443, No. 1, pp. 99-105.
Huang F. et al., Research progress of African swine fever, Chine Swine Industry, Dec. 31, 2013, vol. 6, pp. 58-60.
First Office Action for CN Application No. 201580032193.1 dated Sep. 10, 2019.

* cited by examiner

Sequence at left flank of deletion/insertion

BeninΔMGFA2
vp72 promoter    loxP

AGAGAGGGGTACCATTTAATAAAAACAATAAATTATTTTTTATAACATTATATATAACTTTGTATAGCATACATTATACGAAGTTATATGTTACGT (SEQ ID NO: 31)
MGF 360-9
19462
GUS

AGAGAGGACCATATTTCTTTTTTTGAAAAAATCAAATTAAAAAAAAACATGCTTGTTTGGCATACATGTAACTATGTTATAACCATGTTATAACCA (SEQ ID NO: 32)
MGF 360-9L
19427
NON-CODING REGION
Benin 97/1

BeninΔMGFA2
30033
GUS    NotI   MGF 505-4R
CAGCCAGGGAGGCAAACAATGAGGAATTCTGCAGATATCCATCACTGGCGGCCGCCTCTCCAAGACATCTTGT (SEQ ID NO: 33)

TTTTATCATACATTAAAATTCCAGTAAAATTTATATTTTTTTGGTAAACAAATGTTTTCTCTCCAAGACATCTTGT (SEQ ID NO: 34)
NON-CODING REGION    MGF 505-4R
30026
Benin 97/1

Sequence at right flank of deletion/insertion

Growth curves of Benin 97/1 and BeninΔMGF

─◇─ Benin 97/1
─☐─ BeninΔMGF

Figure 4

Figure 7
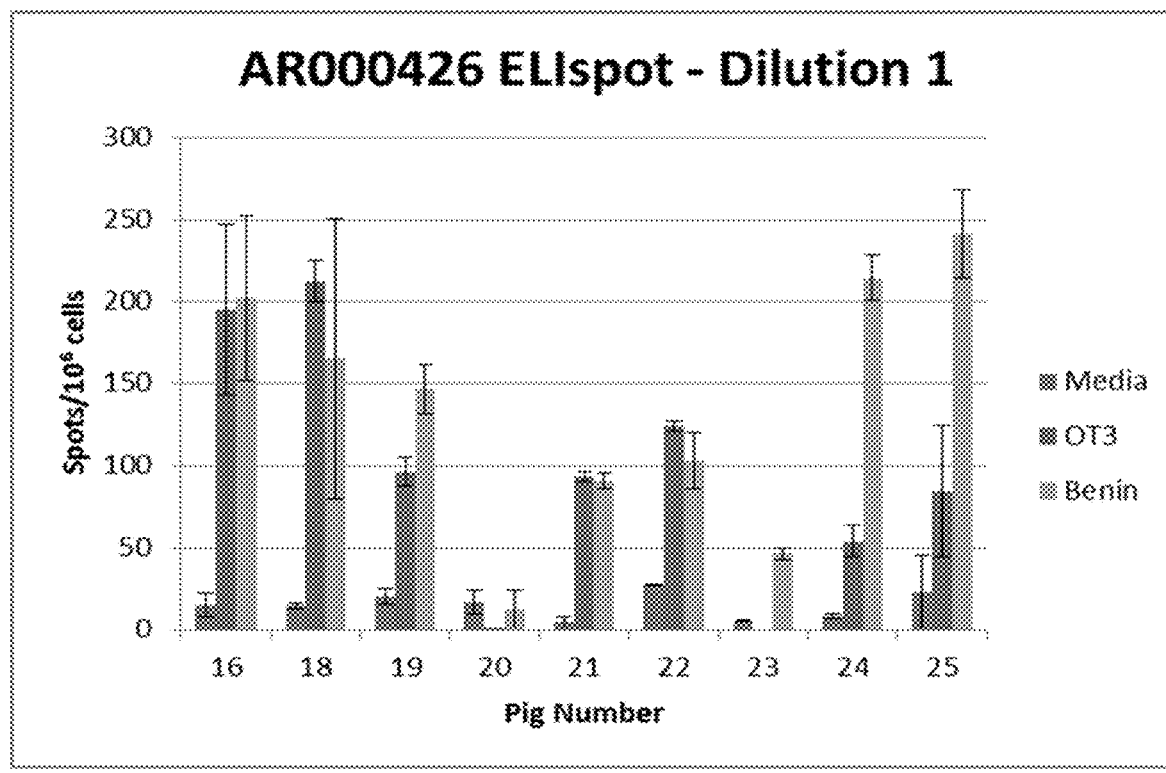
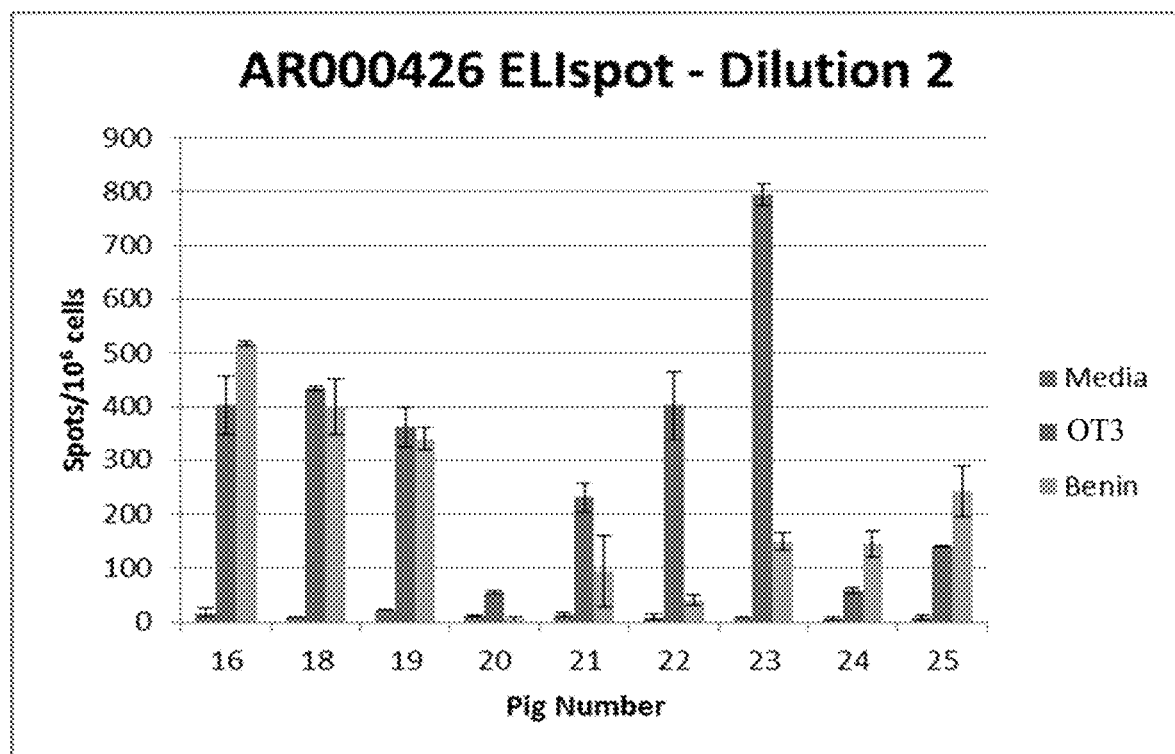

Figure 14

Gamma Delta percentage of cells (as compared with day 0)

Days post infection

○ Ourt 88/3
▨ Benin delta MGF

Figure 19

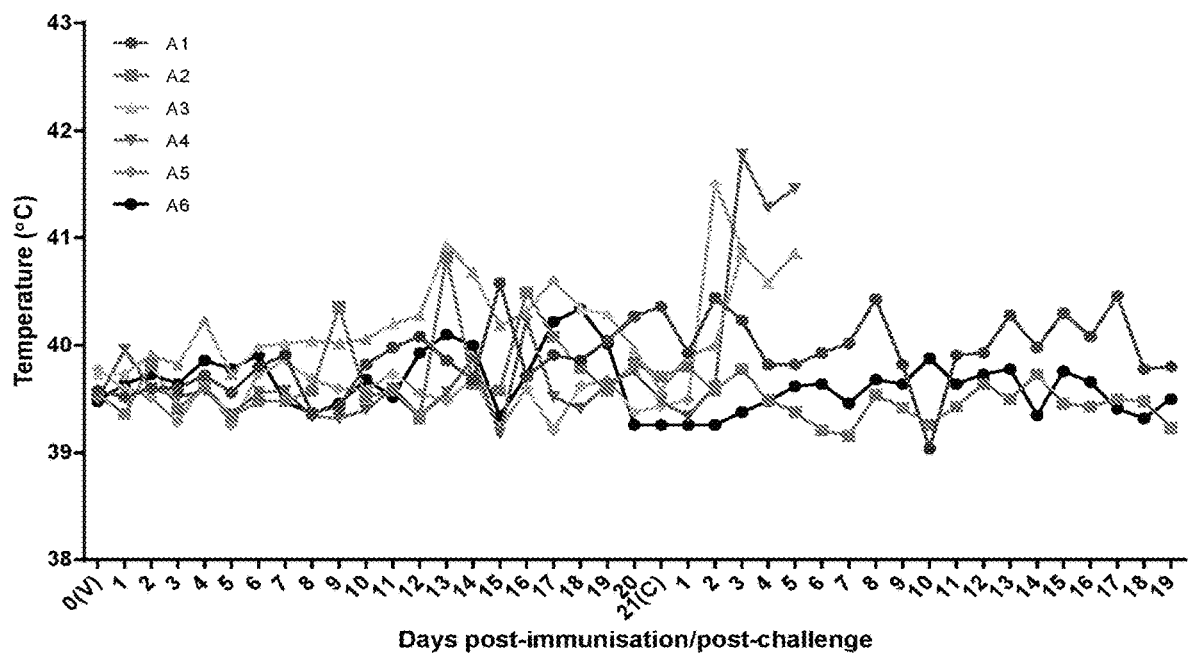
Figure 21A  $10^3$ (IM)
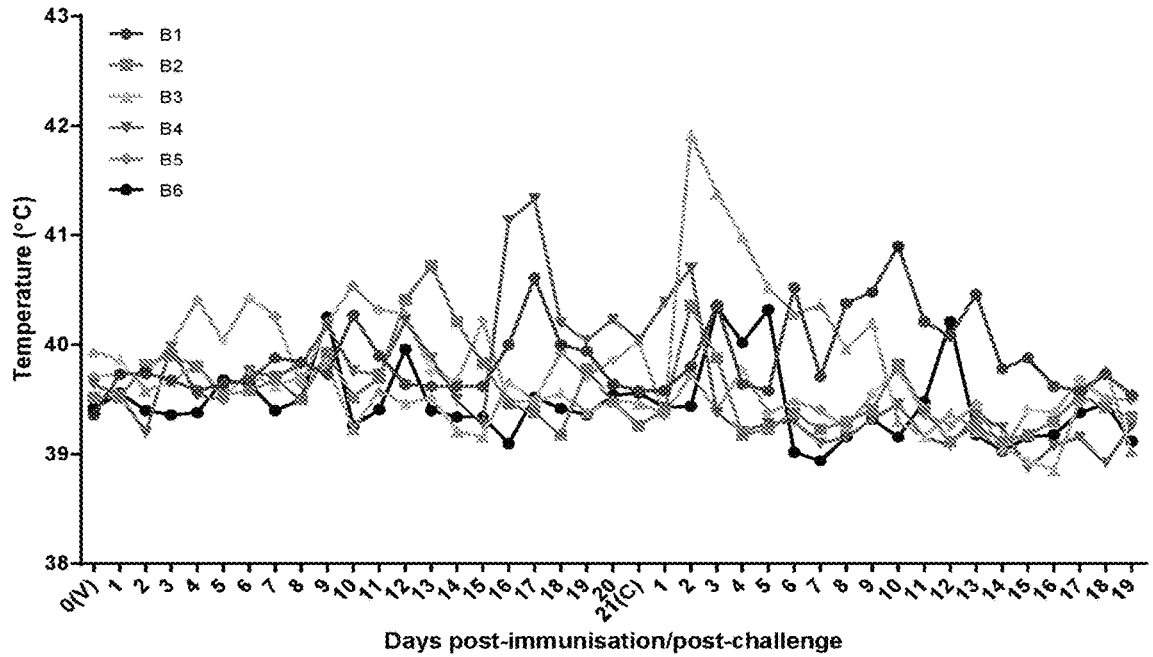
Figure 21B  $10^3$ (IN)

Figure 22C

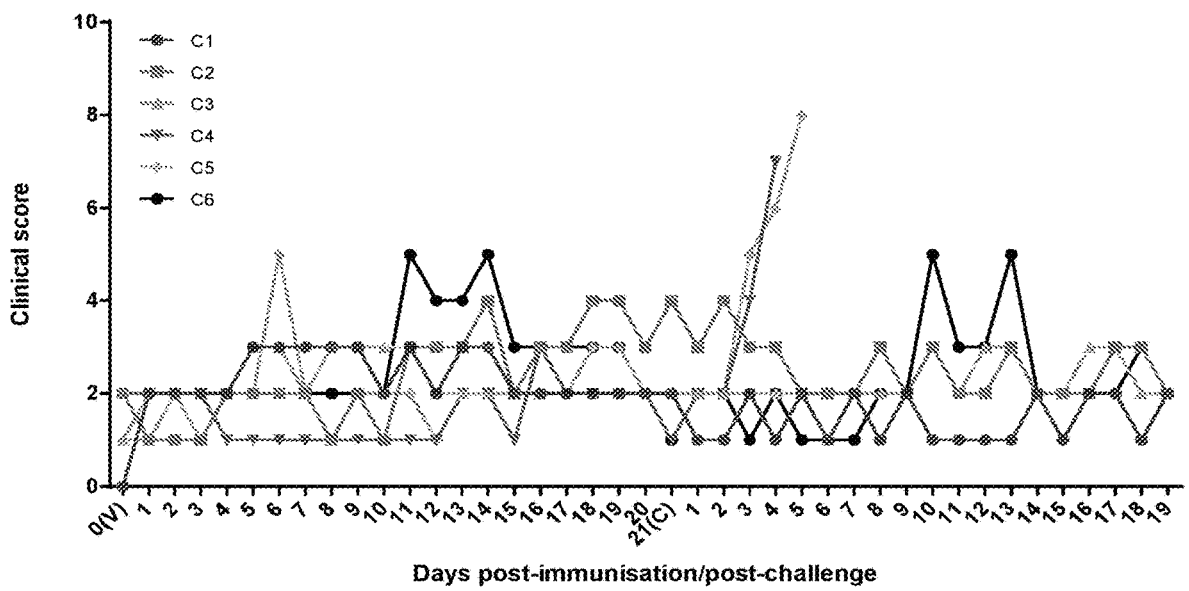
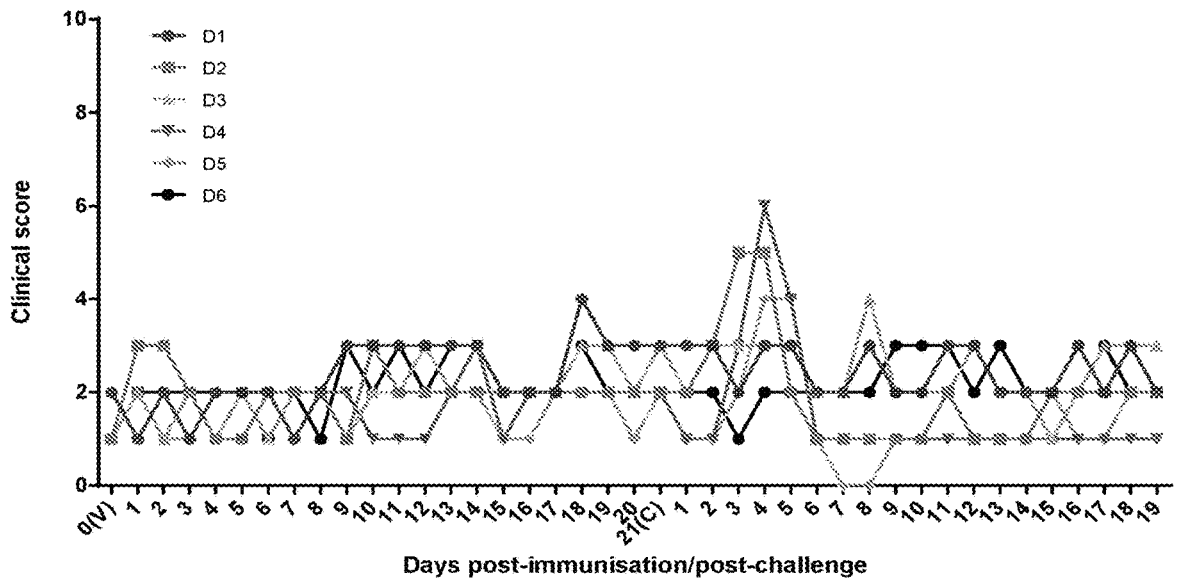

Figure 26
A
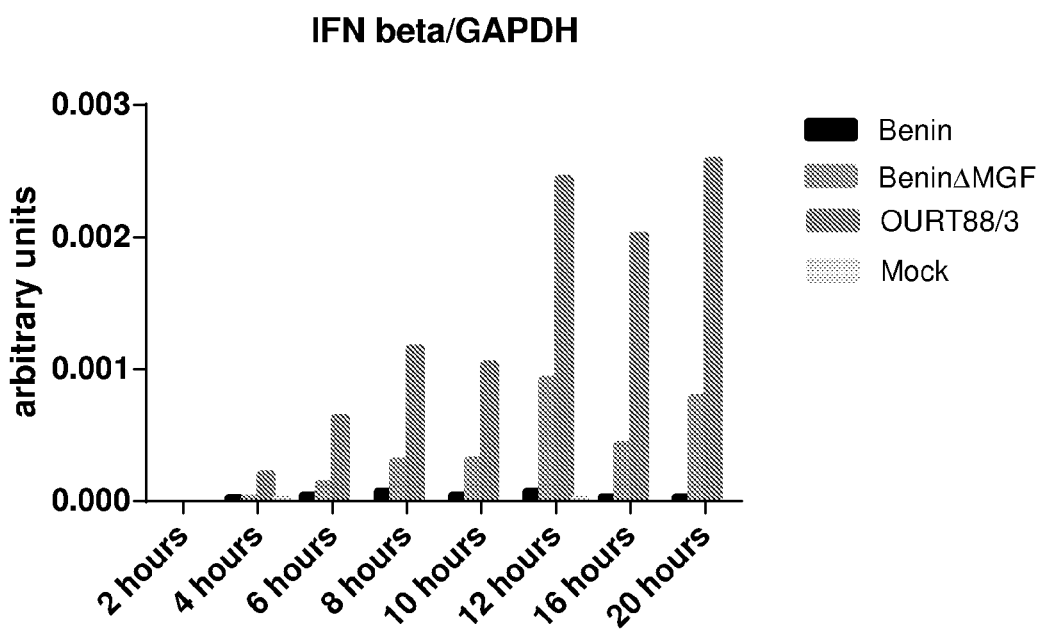
B
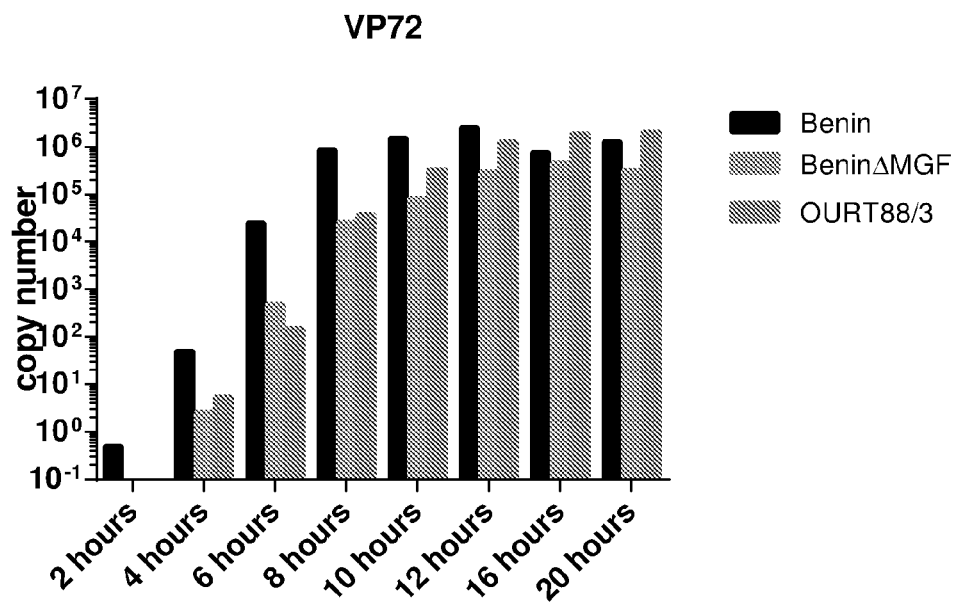

Figure 27

AAATGAATAGATTTAATCCAAGTAGTATTAAAATTTTTTAGAAATAGTGTTCTACAAATAATGAAATGA
ATAGCCCAAAAAAAATAAGGTGTACATTAATGTAATATATTGTTAGGCTAAGTAAATTTAATATTTAAA
GTACTTGGAAAAATATTTTTTAACATATGCTGTCTAGGAATTTTTTTAGACATTTAAAACCATATAGTT
ACTTTATTTATTACACTTAACTTGAAAAGAATTATTGCCTAAAATATTAATAGATGAAGTAATATTGTG
TAATTGAGTCCATAACATGGGTGGGAAACAAAAATCTCGTAATATGAAAAATAAACATCCTAAAAAGAG
TGCAATTGTTATAAGTTTATGTAACTTTATTTTAAAGTAAGAATATAAAAATATGAGTACAAGAGGAAT
AGGGGCCATTACTAATATTGGCTCCAACATCCTGTTGTCTACAAAAAAAATATTTTTTGGCAAAAAA
AAATCCATGGAAGGATATTAATACACATAATTGTTTGACATCATATTGGTATACTTACCAAATAGTAAT
ATACAACCATCCTAATATTCACTTTATGAAATGACCCCCCCCCCACCTATACAGTAAAATAGTATAGG
TTTTAATAAAGAAAAAAGATATTTATGTAGTTTTTATTTTTGTATAGTGCGTGAATGCAAAATAAAATCC
CAAATTTTAACCTTTTCTTTTTTTTTCTATACAGGATGTTAGAAATAGTATTGGCAACGCTGCTAGGCG
ACCTGCAGCGGCTCCGGGTTCTTACCCCTCAGCAGCGGGCGGTTGCCTTCTTTCGAGCCAATACTAAGG
AGCTAGAGGACTTCTTACGCTCAGATGGGCAATCTGAGGAGATACTGTCTGGCCCCCTCCTTAACCGTC
TACTAGAACCCTCATGCCCTCTTGATATTTTAACCGGATATCACCTATTTCGTCAGAATCCCAAGGCAG
GTCAGTTGCGCGGCCTTGAGGTCAAGATGCTTGAACGGTTATACGATGCTAATATTTACAATATATTGT
CTCGGCTGCGACCTAAAAAAGTCCGCAACAAGGCTATTGAGCTATACTGGGTTTTCCGAGCTATCCATA
TTTGTCATGCTCCTTTAGTTTTAGATATTGTACGATATGAGGAACCGGACTTTGCTGAACTGGCCTTTA
TTTGTGCTGCTTACTTTGGTGAACCTCAGGTAATGTATTTGCTCTACAAATATATGCCTCTGACCCGCG
CAGTTCTTACGGATGCCATCCAGATAAGTCTTGAGAGCAACAACCAGGTAGGGATTTGCTATGCTTACT
TGATGGGAGGCAGCCTCAAGGGACTAGTCTCCGCCCCACTGCGTAAACGTCTGCGCGCCAAACTACGCT
CGCAGCGCAAAAAGAAGGACGTTCTTTCACCCCACGACTTCTTACTGCTGCTCCAGTAGCTTTTTTGC
CGCAGGAGCACCGTGGATAGGAGCTCCTCCACGCTCGCGATCCGGCGCTGGAAGCGGAACCGATCGACC
GCCACCTGCTCCCAGGGACCCTTGCGCTCGATGTCGTCGGCTTCCCATACCTCGACGGCTGCAGCAAAG
CGGACGTGCTTCGTGTCATTCGTCCGTTTTTGCGCCGCCGCCCCCCCCCCATTATTCCTGTAAGATTA
GTGTTTAATACCTATAATAACATAATTTTAAGATTTAATATACCAAAACTTAAACTATTTTTGTATAGT
AACTATTAGCATGTCTACACATGATTGTTTTTCAAAAGAGAAACCAGTTGATATGAACGATATATCTGA
GAAATCATCTGTCGTGGATAATGCACCCGAGAAACCAGCTGGAGCGAATCATATACCTGAGAAGTCGGC
CCGCGAAATGACATCATCAGAATGGATTGCTGAATATTGGAAAGGTATAAAACGTGGAAATGACGTGCC
ATGTTGTTGTCCAAGAAAAATGACCAGTGCAGACAAAAAGTTTTCAGTATTTGGTAAGGGATCCCTAAT
ACGCTCCATCCAGAAGAATAATTAAAAAAAATATTTTTTTGGTAAGTTTATAAACTATATAGTTAAAT
ATGGTAAAAAAAATCACATAATAATTAAACTGAACGTGTTAGAATTAATATTTTTTATAATCGGATAT
AATATCCATTAAATCAATAAA (SEQ ID NO: 35)

Left flank - 529bp Right flank - 740bp

PRIMERS FOR CLONING

360-18RFlankL-for-Benin: GCTATCCAAGCTTCTACAAATAATGAAATGAATAGCCC (SEQ ID NO: 36)
360-18RFlankL-rev-Benin2:GCTATCCGGTACCCATAAAGTGAATATTAGGATGGTTG (SEQ ID NO: 37)
360-18RFlankR-for: GCTATCCGCGGCCGCCGACTTCTTACTGCTGCTCCAG (SEQ ID NO: 38)
360-18RFlankR-rev: GCTATCCTCTAGATCTTCTGGATGGAGCGTATTAGG (SEQ ID NO: 39)

PRIMERS FOR SCREENING

18R-Benin-Pair1-For: GAGTACAAGAGGAATAGGGGCC (SEQ ID NO: 40)
18R-OURT-Pair1-Rev: GCATGACAAATATGGATAGCTCG (SEQ ID NO: 41)
Pair 1: 715 bp
18R-OURT-Pair2-For: GTCCGCAACAAGGCTATTGAG (SEQ ID NO: 42)
18R-OURT-Pair2-Rev: GACGTTTACGCAGTGGGC (SEQ ID NO: 43)
Pair 2: 307 bp
18R-OURT-Pair3-For: CAACCAGGTAGGGATTTGCTATGC (SEQ ID NO: 44)
18R-OURT-Pair3-Rev: GCTGCAGCCGTCGAGG (SEQ ID NO: 45)
Pair 3: 301 bp Figure 28
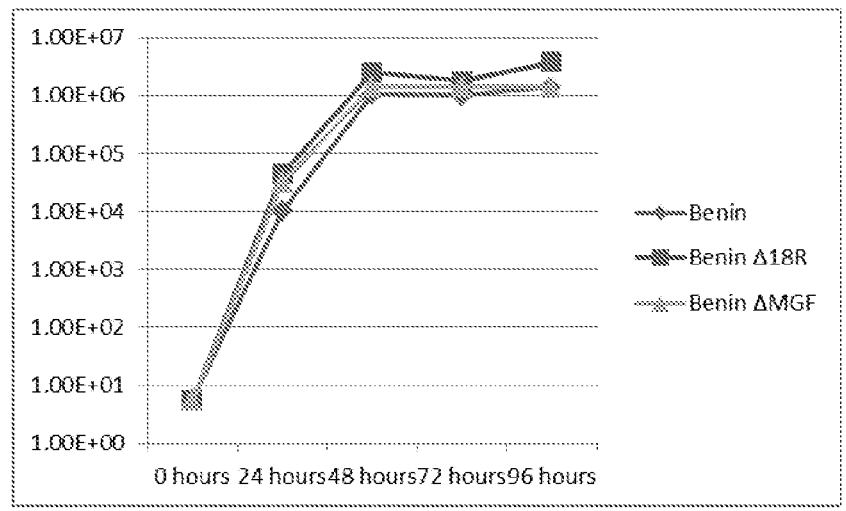
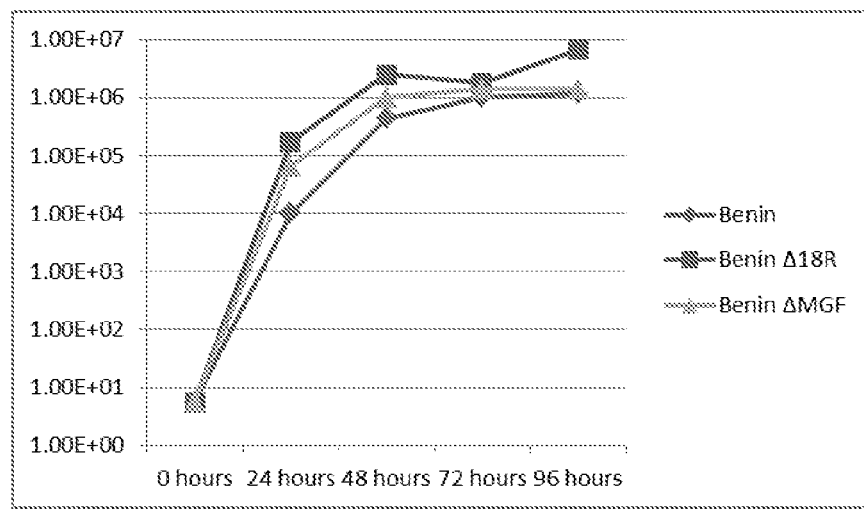

Figure 29C

Benin delta MGF $10^4$ (IM)

Days post-immunisation/post-challenge

Figure 29D

Benin Delta MGF 10^3 (IN)

Days post-immunisation/post-challenge

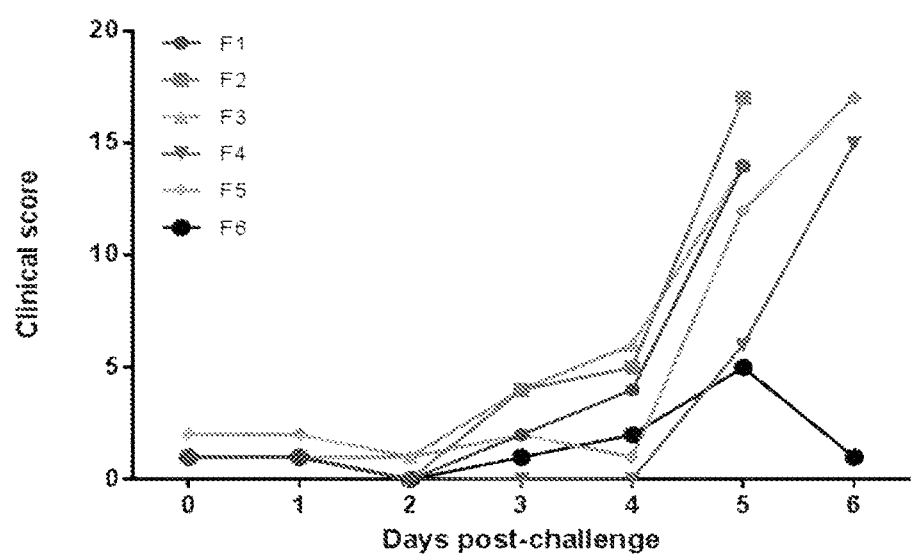

Figure 32

SEQUENCE LISTING

<160> NUMBER OF SEQ ID NOS: 45

<210> SEQ ID NO 1
<211> LENGTH: 350
<212> TYPE: PRT
<213> ORGANISM: African swine fever virus

<400> SEQUENCE: 1

Met Val Leu Ser Leu Gln Thr Leu Thr Lys Lys Val Leu Ala Ser Gln
1               5                   10                  15

Tyr Pro Ala Lys Cys His Pro His Phe Leu Lys Cys Cys Gly Leu Trp
            20                  25                  30

Trp His Asn Gly Pro Ile Met Tyr His Gln Lys Lys Ile Trp Thr Pro
        35                  40                  45

Tyr Phe Lys Asn Gly Thr Asn Leu Asn Ala Ala Leu Val Lys Ala Val
    50                  55                  60

Glu Glu Asn Asn His Asp Leu Ile Glu Leu Phe Thr Glu Trp Gly Ala
65                  70                  75                  80

Asn Ile Asn Tyr Gly Leu Leu Ser Val Asn Thr Glu His Thr Arg Asp

```
                85                  90                  95
Leu Cys Arg Gln Leu Gly Ala Lys Glu Gln Leu Asn Asp Gln Glu Ile
            100                 105                 110
Leu Arg Phe Phe Tyr Thr Leu Lys Arg Asp Leu Thr Ser Ser Asn Ile
            115                 120                 125
Ile Phe Cys His Glu Val Phe Ser Asn Asn Pro Ile Leu Asp Thr Ile
            130                 135                 140
Asn Arg Phe Glu Val Lys Gly Met Ile Tyr Glu Gln Leu Glu Gly Leu
145                 150                 155                 160
Met Val Glu Thr Asp Ile Leu Ser Glu Met Phe Thr Lys Tyr Trp Tyr
                165                 170                 175
Ala Met Ala Ile Glu Phe Asn Leu Lys Glu Ala Ile Cys Tyr Phe Tyr
            180                 185                 190
Gln Arg Tyr Ala His Leu His Arg Trp Arg Leu Met Cys Ala Leu Phe
            195                 200                 205
Tyr Asn Asn Val Phe Asp Leu His Glu Leu Tyr Ala Lys Glu Lys Val
            210                 215                 220
Arg Met Asp Met Asp Glu Met Leu Arg Trp Ala Cys Arg Lys Asn Tyr
225                 230                 235                 240
Asn Tyr Leu Thr Ile Tyr Tyr Cys Cys Val Ala Leu Gly Ala Asp Ile
                245                 250                 255
Asn Gln Ala Met Phe His Ser Ile Gln Phe Tyr Asn Ile Gly Asn Ile
            260                 265                 270
Phe Phe Cys Ile Asp Leu Gly Ala Asn Ala Phe Glu Glu Gly Lys Thr
            275                 280                 285
Leu Ala His Gln Lys Asp Asn Ser Phe Ile Ala Ser Met Leu Ser Leu
            290                 295                 300
Asn Cys Tyr Ser Met Asn Asp Ser Leu Ser Leu Lys Glu Thr Asp Pro
305                 310                 315                 320
Glu Val Ile Lys Arg Met Leu Lys Asp Tyr His Ser Lys Asn Leu Ser
                325                 330                 335
Ile Ala His Lys His Tyr Ile Asn Asp Gly Phe Asn Asp Ile
            340                 345                 350

<210> SEQ ID NO 2
<211> LENGTH: 356
<212> TYPE: PRT
<213> ORGANISM: African swine fever virus

<400> SEQUENCE: 2

Met Val Pro Ser Leu Gln Ser Phe Ala Lys Lys Val Leu Ala Ser Gln
1               5                   10                  15
His Val Ser Ile Asp Tyr His Val Ile Leu Glu Arg Cys Gly Leu Trp
            20                  25                  30
Trp Tyr Lys Ala Pro Ile Ser Leu Asp Cys Lys His Met Leu Ile Lys
        35                  40                  45
Leu Pro Asn Phe Ala Asp Gly Leu Asp Leu Asn Thr Ala Leu Met Leu
    50                  55                  60
Ala Thr Lys Glu Asn Asn Tyr Gln Leu Ile Lys Met Phe Thr Asp Trp
65                  70                  75                  80
Gly Ala Asp Ile Asn Tyr Gly Leu Ile Cys Ala Asn Thr Pro Pro Ile
                85                  90                  95
Arg Glu Phe Cys Trp Glu Leu Gly Ala Lys Tyr Gln Val Asp Lys Lys
            100                 105                 110
```

Lys Ile Met His Ile Phe Phe Lys Leu Ile His Pro Asn Thr Thr Ser
            115                 120                 125

Asn Asn Ile Ile Leu Cys Leu Lys Phe Asn Asp Asn Pro Phe Ser
130                 135                 140

Ala Tyr Val Ile Ile Arg Glu Ile Lys Ser Cys Ile His Trp Lys Leu
145                 150                 155                 160

Lys Asn Leu Ala Glu Asp Thr Asn Val Leu Ser Asn Ile Ser Asp Gly
                165                 170                 175

Asp Met Leu Thr Ile Tyr Cys Phe Ile Val Ala Leu Gln Asp Asn Leu
            180                 185                 190

Arg Glu Ala Ile Ser Tyr Val Tyr Gln His Phe Lys Tyr Leu Asn Thr
            195                 200                 205

Trp Trp Leu Thr Cys Ala Leu Cys Tyr Asn Lys Leu Phe Asp Leu His
            210                 215                 220

Asn Leu Tyr Glu Lys Glu Lys Ile Arg Met Asp Met Asp Glu Met Met
225                 230                 235                 240

Arg Ile Ala Cys Thr Lys Asp Asn Asn Phe Leu Thr Ile Tyr Tyr Cys
                245                 250                 255

Phe Ile Leu Gly Ala Asn Ile Asn Leu Ala Met Ile Ala Ser Ile Arg
            260                 265                 270

Phe Tyr Asn Met Asp Asn Leu Phe Phe Cys Ile Asp Leu Gly Ala Asp
            275                 280                 285

Ala Phe Glu Glu Ala Lys Ala Leu Ala Glu Gln Gln Asn Tyr Tyr Leu
            290                 295                 300

Ile Ser His Arg Leu Ser Leu Asp Ile Tyr Ser Pro Asp Ser Ser Leu
305                 310                 315                 320

Leu Thr Leu Lys Glu Ala Asp Pro Asn Lys Ile Tyr Arg Leu Leu Lys
                325                 330                 335

Asn Tyr Lys Ser Lys Ser Met Leu Ala Tyr Leu Asn Tyr Asp Ile Asn
            340                 345                 350

Asp Thr Ser Leu
            355

<210> SEQ ID NO 3
<211> LENGTH: 353
<212> TYPE: PRT
<213> ORGANISM: African swine fever virus

<400> SEQUENCE: 3

Met Leu Pro Ser Leu Gln Ser Leu Thr Lys Lys Val Leu Ala Gly Gln
1               5                   10                  15

Cys Val Ser Val Asp His Tyr His Ile Leu Lys Cys Cys Gly Leu Trp
                20                  25                  30

Trp His Asn Gly Pro Ile Met Leu His Ile Arg Arg Asn Lys Leu Phe
            35                  40                  45

Ile Arg Ser Thr Cys Phe Ser Gln Gly Ile Glu Leu Asn Ile Gly Leu
        50                  55                  60

Met Lys Ala Val Lys Glu Asn Asn His Asp Leu Ile Lys Leu Phe Thr
65                  70                  75                  80

Glu Trp Gly Ala Asp Ile Asn Tyr Gly Met Ile Cys Ala Leu Thr Glu
                85                  90                  95

Asn Thr Arg Asp Leu Cys Lys Glu Leu Gly Ala Lys Glu Tyr Leu Glu
            100                 105                 110

Arg Glu Tyr Ile Leu Lys Ile Phe Phe Asp Thr Thr Arg Asp Lys Thr
            115                 120                 125

```
Ser Ser Asn Ile Ile Phe Cys His Glu Val Phe Ser Asn Asn Pro Asn
        130                 135                 140

Leu Arg Ile Ile Asp Asn Leu Asp Leu Arg Gly Glu Ile Met Trp Glu
145                 150                 155                 160

Leu Arg Gly Leu Met Glu Ile Thr Phe Met Leu Asp His Asp Asp Ser
                165                 170                 175

Phe Ser Thr Val Leu Thr Lys Tyr Trp Tyr Ala Ile Ala Val Asp Tyr
                180                 185                 190

Asp Leu Lys Asp Ala Ile Arg Tyr Phe Tyr Gln Lys Tyr Pro Arg Leu
            195                 200                 205

His Arg Trp Arg Leu Met Cys Ala Leu Phe Tyr Asn Asn Val Phe Asp
        210                 215                 220

Leu His Glu Leu Tyr Glu Ile Glu Arg Val Arg Met Asp Ile Asp Glu
225                 230                 235                 240

Met Met His Ile Ala Cys Ile Gln Asp Tyr Ser Tyr Ser Ala Ile Tyr
                245                 250                 255

Tyr Cys Phe Ile Met Gly Ala Asn Ile Asn Gln Ala Met Leu Val Ser
                260                 265                 270

Ile Gln Asn Tyr Asn Leu Gly Asn Leu Phe Phe Cys Ile Asp Leu Gly
            275                 280                 285

Ala Asn Ala Phe Glu Glu Gly Lys Ala Leu Ala Glu Gln Lys Glu Asn
        290                 295                 300

Tyr Leu Ile Ala His Ala Leu Ser Leu Lys His Tyr Asn Pro Val Ile
305                 310                 315                 320

Ser Leu Leu Ser Asn Val Met Asp Pro Glu Lys Ile Asn Tyr Met Leu
                325                 330                 335

Lys Asn Tyr His Ser Ile Asn Met Gly Ile Phe Leu Asp Tyr Glu Gln
                340                 345                 350

Arg

<210> SEQ ID NO 4
<211> LENGTH: 350
<212> TYPE: PRT
<213> ORGANISM: African swine fever virus

<400> SEQUENCE: 4

Met Leu Pro Ser Leu Gln Ser Leu Thr Lys Lys Val Leu Ala Gly Gln
1               5                   10                  15

Cys Val Pro Thr Asn Gln His Tyr Leu Leu Lys Tyr Tyr Asp Leu Trp
                20                  25                  30

Trp Tyr Asn Ala Pro Ile Thr Phe Asp His Asn Leu Arg Leu Ile Lys
            35                  40                  45

Ser Ser Gly Ile Lys Glu Gly Leu Asp Leu Asn Thr Ala Leu Val Lys
        50                  55                  60

Ala Val Arg Glu Asn Asn Tyr Ser Leu Ile Lys Leu Phe Thr Glu Trp
65                  70                  75                  80

Gly Ala Asp Ile Asn Tyr Gly Leu Val Ser Val Asn Thr Glu His Thr
                85                  90                  95

Arg Asp Leu Cys Gln Glu Leu Gly Ala Lys Glu Ile Leu Asn Glu Glu
            100                 105                 110

Glu Ile Leu Gln Ile Phe Ile Asp Leu Lys Phe His Lys Thr Ser Ser
        115                 120                 125

Asn Ile Ile Leu Cys His Glu Val Phe Ser Asn Asn Pro Ile Leu Gln
    130                 135                 140
```

```
Lys Val Asn Asn Leu Lys Leu Arg Ile Glu Ile Phe Trp Glu Leu Arg
145                 150                 155                 160

Glu Leu Ile Glu Lys Thr Asp Leu Leu Asn Asn Glu Phe Leu Leu Ser
            165                 170                 175

Thr Leu Leu Lys Tyr Trp Tyr Ala Ile Ala Val Arg Tyr Ser Leu
        180                 185                 190

Lys Glu Ala Ile Gln Tyr Phe Tyr Gln Lys Tyr Thr His Met Asn Thr
            195                 200                 205

Trp Arg Leu Thr Cys Ala Leu Cys Phe Asn Asn Val Phe Asp Leu His
        210                 215                 220

Glu Ala Tyr Glu Lys Asp Lys Ile His Met Asp Ile Glu Glu Met Met
225                 230                 235                 240

Arg Ile Ala Cys Ile Lys Asp His Asn Leu Ser Thr Met Tyr Tyr Cys
                245                 250                 255

Tyr Met Leu Gly Ala Asn Ile Asn Gln Ala Met Leu Thr Ser Ile Gln
            260                 265                 270

Tyr Tyr Asn Ile Glu Asn Met Phe Phe Cys Met Asp Leu Gly Ala Asp
        275                 280                 285

Val Phe Glu Glu Gly Thr Thr Ala Leu Gly Glu Gly Tyr Glu Leu Ile
        290                 295                 300

Lys Asn Ile Leu Ser Leu Lys Ile Tyr Ser Pro Thr Thr Ile Pro Leu
305                 310                 315                 320

Pro Lys Ser Thr Asp Pro Glu Ile Ile Asp His Ala Leu Lys Asn Tyr
                325                 330                 335

Phe Ser Lys Asn Met Met Ile Phe Leu Ser Tyr Asp Leu Arg
            340                 345                 350

<210> SEQ ID NO 5
<211> LENGTH: 353
<212> TYPE: PRT
<213> ORGANISM: African swine fever virus

<400> SEQUENCE: 5

Met Ser Leu Pro Leu Ser Leu Gln Thr Leu Val Lys Lys Thr Val Ala
1               5                   10                  15

Ser Gln Cys Leu Ser Ile Asp Glu His Cys Ile Leu Lys Tyr Cys Gly
            20                  25                  30

Leu Trp Trp His Asp Ala Pro Leu Lys Leu Cys Met Asp Arg Gly Arg
        35                  40                  45

Ile Gln Ile Lys Ser Gly Phe Leu Gly Glu Asp Ile Asp Leu Arg Val
50                  55                  60

Ala Leu Ile Ile Ala Val Lys Glu Asn Asn Tyr Ser Leu Ile Lys Leu
65                  70                  75                  80

Phe Thr Glu Trp Gly Ala Asn Ile Asn Tyr Ser Leu Leu Ser Ile Asn
            85                  90                  95

Thr Lys His Ile Arg Glu Leu Cys Arg Gln Leu Gly Ala Lys Glu Thr
            100                 105                 110

Leu Glu Asp Asn Asp Ile Phe Arg Ile Phe Thr Arg Ile Met His Asn
        115                 120                 125

Lys Thr Ser Gly Ser Ile Ile Leu Cys His Glu Ile Phe Met Asn Asn
130                 135                 140

Pro Met Leu Glu Asn Lys Phe Val Ile Gln Leu Arg Gly Leu Ile Tyr
145                 150                 155                 160

Lys Arg Leu Trp Gly Leu Ile Glu Ile Lys Glu Thr Asp Glu Leu Asn
```

-continued

```
                165                 170                 175
Asp Leu Leu Val Lys Tyr Trp Tyr Ala Lys Ala Val Gln Tyr Val Cys
            180                 185                 190

Lys Asn Ala Ile Cys Phe Leu Asp Glu Lys Tyr Thr Asp Leu Asn Glu
            195                 200                 205

Trp Arg Leu Lys Cys Leu Leu Tyr Tyr Asn Lys Ile Tyr Glu Leu His
            210                 215                 220

Glu Met Tyr His Lys Lys Val Gln Ile Asp Val His Asp Met Ile
225                 230                 235                 240

Cys Leu Ala Cys Ala Lys Asp Asn Asn Leu Leu Thr Ile Tyr Tyr Cys
                245                 250                 255

Tyr Ala Leu Gly Gly Asn Ile Asn Gln Ala Met Leu Thr Ser Val Gln
                260                 265                 270

Tyr Tyr Asn Val Gly Asn Ile Phe Phe Cys Ile Asp Leu Gly Gly Asn
                275                 280                 285

Ala Phe Glu Glu Gly Arg Ala Ile Ala Glu Gln Lys Gly Tyr Asn Phe
            290                 295                 300

Leu Ser His Ser Leu Thr Leu Asp Ile Tyr Ser Ser Asp Ala Ser Leu
305                 310                 315                 320

Pro Leu Asn Leu Lys Asp Pro Glu Lys Ile Ser Ser Leu Leu Lys Asp
                325                 330                 335

Tyr Lys Ser Lys Asn Leu Ser Ile Ile Trp Glu Tyr Ser His Asn Ile
                340                 345                 350

Leu

<210> SEQ ID NO 6
<211> LENGTH: 357
<212> TYPE: PRT
<213> ORGANISM: African swine fever virus

<400> SEQUENCE: 6

Met Leu Ser Leu Gln Thr Leu Ala Lys Lys Val Val Ala Cys Asn Tyr
1               5                   10                  15

Leu Ser Ser Asp Tyr Asp Tyr Thr Leu Gln Arg Phe Gly Leu Trp Trp
            20                  25                  30

Asp Leu Gly Pro Ile His Leu Cys Asn Asn Cys Lys Gln Val Phe Ser
        35                  40                  45

Tyr Lys His Leu Gln Cys Phe Ser Glu Asp Leu Cys Leu Glu Ala
    50                  55                  60

Ala Leu Val Lys Ala Val Lys Ser Asp Asn Leu Glu Leu Ile Arg Leu
65                  70                  75                  80

Phe Val Asp Trp Gly Ala Asn Pro Glu Tyr Gly Leu Ile Arg Val Pro
                85                  90                  95

Ala Val Tyr Leu Lys Arg Leu Cys Ala Glu Leu Gly Gly Leu Thr Pro
            100                 105                 110

Val Ser Glu Pro Arg Leu Leu Glu Ile Leu Lys Glu Val Ala Asn Leu
        115                 120                 125

Lys Ser Cys Ala Gly Val Leu Leu Gly Tyr Asp Met Phe Cys His Asn
    130                 135                 140

Pro Leu Leu Glu Thr Val Thr Arg Thr Thr Leu Asp Thr Val Thr Tyr
145                 150                 155                 160

Thr Cys Ser Asn Ile Pro Leu Thr Gly Asp Thr Ala His Leu Leu Leu
                165                 170                 175

Thr Lys Phe Trp Phe Ala Leu Ala Leu Arg His Asn Phe Thr Lys Ala
```

-continued

```
                180                 185                 190
    Ile His Tyr Phe Tyr Lys Arg His Lys Asn Gln Leu Tyr Trp Arg Val
                    195                 200                 205

Ala Cys Ser Leu Tyr Phe Asn Asn Ile Phe Asp Ile His Glu Leu Cys
    210                 215                 220

Arg Glu Lys Glu Ile Cys Ile Ser Pro Asn Leu Met Met Lys Phe Ala
    225                 230                 235                 240

Cys Leu Arg Glu Lys Asn Tyr Ala Ala Ile Tyr Tyr Cys His Arg Leu
                    245                 250                 255

Gly Ala Ser Leu Asp Tyr Gly Met Asn Leu Ser Ile Tyr Asn Asn Asn
                260                 265                 270

Thr Leu Asn Met Phe Phe Cys Ile Asp Leu Gly Ala Ala Asp Phe Asp
                275                 280                 285

Arg Ala Gln Leu Ile Ala His Lys Ala Tyr Met Tyr Asn Leu Ser Asn
                290                 295                 300

Ile Phe Leu Val Lys Gln Leu Phe Ser Arg Asp Val Thr Leu Val Leu
    305                 310                 315                 320

Asp Val Thr Glu Pro Gln Glu Ile Tyr Asp Met Leu Lys Thr Tyr Thr
                    325                 330                 335

Ser Lys Asn Met Lys Arg Ala Glu Glu Tyr Leu Thr Ala His Pro Glu
                340                 345                 350

Ile Ile Val Ile Asp
                355

<210> SEQ ID NO 7
<211> LENGTH: 531
<212> TYPE: PRT
<213> ORGANISM: African swine fever virus

<400> SEQUENCE: 7

Met Phe Ser Leu Gln Asn Leu Cys Arg Lys Thr Leu Pro Asp Cys Lys
1               5                   10                  15

Leu Pro Glu Phe Phe Asp Asp Tyr Ile Leu Gln Leu Leu Gly Leu Tyr
                20                  25                  30

Trp Glu Asn His Gly Thr Ile Gln Arg Ala Gly Asn Asn Cys Val Leu
            35                  40                  45

Ile Gln Gln His Thr Leu Ile Pro Val Asn Glu Ala Leu Arg Ile Ala
    50                  55                  60

Ala Ser Glu Glu Asn Tyr Glu Ile Val Gly Leu Leu Ala Trp Glu
65                  70                  75                  80

Gly Asn Leu Tyr Tyr Ala Ile Ile Gly Ala Leu Glu Gly Asn Arg Tyr
                85                  90                  95

Asn Leu Ile Arg Lys Tyr Asp Asp Gln Ile Lys Asp His His Asp Ile
            100                 105                 110

Leu Pro Phe Ile Asp Asp Pro Ile Ile Phe His Lys Cys His Ile Met
    115                 120                 125

Arg Arg Cys Phe Phe Asp Cys Ile Leu Tyr Gln Ala Val Lys Tyr Ser
    130                 135                 140

Lys Phe Arg Val Leu Leu Tyr Phe Lys Tyr Thr Leu Glu Asp Asp Leu
145                 150                 155                 160

Pro Leu Val His Leu Leu Ile Glu Lys Ala Cys Glu Asp His Asn Tyr
                165                 170                 175

Glu Val Ile Lys Trp Ile Tyr Glu Asn Leu His Val Cys His Ile Ile
            180                 185                 190
```

Asp Thr Phe Asp Cys Ala Ile Ala His Lys Asp Leu Arg Leu Tyr Cys
            195                 200                 205

Leu Gly Tyr Thr Phe Ile Tyr Asn Arg Ile Val Pro Tyr Lys Tyr His
        210                 215                 220

His Leu Asp Ile Leu Ile Leu Ser Ser Leu Gln Leu Leu His Lys Val
225                 230                 235                 240

Ala Ala Lys Gly Tyr Leu Asp Phe Ile Leu Glu Thr Leu Lys Tyr Asp
                245                 250                 255

His Asn Ile Asp Asn Leu Asp Val Ile Leu Thr Gln Ala Ala Thr Tyr
            260                 265                 270

Asn His Arg Lys Ile Leu Thr Tyr Phe Ile Pro Gln Ser Thr Tyr Ala
        275                 280                 285

Gln Ile Glu Gln Cys Leu Phe Val Ala Ile Lys Thr Lys Ser Ser Lys
    290                 295                 300

Lys Thr Leu Asn Leu Leu Ser His Leu Asn Leu Ser Ile Lys Leu
305                 310                 315                 320

Ile Gln Lys Ile Ser Gln Tyr Val Ala Thr Phe Asn Ser Thr Asn Ile
                325                 330                 335

Ile Gly Ile Leu Ser Met Lys Arg Lys Lys Ile Tyr Leu Asp Ile
            340                 345                 350

Ile Leu Thr Lys Phe Val Lys Asn Ala Ile Phe Asn Lys Phe Val Val
        355                 360                 365

Arg Cys Met Glu Arg Phe Ser Ile Asn Pro Glu Arg Ile Val Lys Met
    370                 375                 380

Ala Ala Arg Ile Asn Lys Met Met Leu Val Lys Lys Ile Ser Glu His
385                 390                 395                 400

Val Trp Lys Asn His Ala Ala Arg Leu Lys His Leu Lys His Ala Val
                405                 410                 415

His Thr Met Lys His Lys Asp Gly Lys Asn Arg Leu Met Asn Phe Ile
            420                 425                 430

Tyr Glu His Cys Tyr Tyr His Met Gln Gly Glu Ile Phe Ser Leu
        435                 440                 445

Ala Arg Phe Tyr Ala Ile His His Ala Pro Lys Leu Phe Asp Val Phe
    450                 455                 460

Tyr Asn Cys Cys Ile Leu Asp Thr Ile Arg Phe Lys Ser Leu Leu Leu
465                 470                 475                 480

Asp Cys Ser His Ile Ile Gly Lys Asn Ala His Asp Ala Thr Asn Ile
                485                 490                 495

Asn Ile Val Asn Lys Tyr Ile Gly Asn Leu Phe Ala Met Gly Val Leu
            500                 505                 510

Ser Lys Lys Glu Ile Leu Gln Asp Tyr Pro Ser Ile Tyr Ser Lys His
        515                 520                 525

Tyr Met Pro
    530

<210> SEQ ID NO 8
<211> LENGTH: 526
<212> TYPE: PRT
<213> ORGANISM: African swine fever virus

<400> SEQUENCE: 8

Met Phe Ser Leu Gln Asp Leu Cys Arg Lys His Leu Phe Ile Leu Pro
1               5                   10                  15

Asp Val Phe Gly Glu His Val Leu Gln Arg Leu Gly Leu Tyr Trp Arg
            20                  25                  30

Cys His Gly Ser Leu Gln Arg Ile Gly Asp Asp His Ile Leu Ile Arg
         35                  40                  45

Arg Asp Leu Ile Leu Ser Thr Asn Glu Ala Leu Arg Met Ala Gly Glu
 50                  55                  60

Glu Gly Asn Asn Glu Val Val Lys Leu Leu Leu Trp Lys Gly Asn
 65                  70                  75                  80

Leu His Tyr Ala Val Ile Gly Ala Leu Gln Gly Asp Gln Tyr Asp Leu
                 85                  90                  95

Ile His Lys Tyr Glu Asn Gln Ile Gly Asp Phe His Phe Ile Leu Pro
                100                 105                 110

Leu Ile Gln Asp Ala Asn Thr Phe Glu Lys Cys His Ala Leu Glu Arg
                115                 120                 125

Phe Cys Gly Val Ser Cys Leu Leu Lys His Ala Thr Lys Tyr Asn Met
                130                 135                 140

Leu Pro Ile Leu Gln Lys Tyr Gln Glu Glu Leu Ser Met Arg Ala Tyr
145                 150                 155                 160

Leu His Glu Thr Leu Phe Glu Leu Ala Cys Leu Trp Gln Arg Tyr Asp
                165                 170                 175

Val Leu Lys Trp Ile Glu Gln Thr Met His Val Tyr Asp Leu Lys Ile
                180                 185                 190

Met Phe Asn Ile Ala Ile Ser Lys Arg Asp Leu Thr Met Tyr Ser Leu
                195                 200                 205

Gly Tyr Ile Phe Leu Phe Asp Arg Gly Asn Thr Glu Ala Thr Leu Leu
                210                 215                 220

Thr Gln His Leu Glu Lys Thr Ala Ala Lys Gly Leu Leu His Phe Val
225                 230                 235                 240

Leu Glu Thr Leu Lys Tyr Gly Gly Asn Ile Asp Thr Val Leu Thr Gln
                245                 250                 255

Ala Val Lys Tyr Asn His Arg Lys Leu Leu Asp Tyr Phe Leu Arg Gln
                260                 265                 270

Leu Pro Arg Lys His Ile Glu Lys Leu Leu Leu Ala Val Gln Glu
                275                 280                 285

Lys Ala Ser Lys Lys Thr Leu Asn Leu Leu Ser His Leu Asn Tyr
                290                 295                 300

Ser Val Lys Arg Ile Lys Lys Leu Leu Arg Tyr Val Ile Glu Tyr Glu
305                 310                 315                 320

Ser Thr Leu Val Ile Lys Ile Leu Leu Lys Lys Arg Val Asn Leu Ile
                325                 330                 335

Asp Ala Met Leu Glu Lys Met Val Arg Tyr Phe Ser Ala Thr Lys Val
                340                 345                 350

Arg Thr Ile Met Asp Glu Leu Ser Ile Ser Pro Glu Arg Val Ile Lys
                355                 360                 365

Met Ala Ile Gln Lys Met Arg Thr Asp Ile Val Ile His Thr Ser Tyr
370                 375                 380

Val Trp Glu Asp Asp Leu Glu Arg Leu Thr Arg Leu Lys Asn Met Val
385                 390                 395                 400

Tyr Thr Ile Lys Tyr Glu His Gly Lys Lys Met Leu Ile Lys Val Met
                405                 410                 415

His Gly Ile Tyr Lys Asn Leu Leu Tyr Gly Glu Arg Glu Lys Val Met
                420                 425                 430

Phe His Leu Ala Lys Leu Tyr Val Ala Gln Asn Ala Ala Thr Gln Phe
                435                 440                 445

```
Arg Asp Ile Cys Lys Asp Cys Tyr Lys Leu Asp Val Ala Arg Phe Lys
    450                 455                 460
Pro Arg Phe Lys Gln Leu Ile Leu Asp Cys Leu Glu Ile Val Thr Lys
465                 470                 475                 480
Lys Ser Cys Tyr Ser Ile Leu Glu Ile Leu Glu Lys His Ile Ile Ser
                485                 490                 495
Leu Phe Thr Met Lys Val Met Thr Glu Glu Lys Asn Leu Cys Leu
                500                 505                 510
Glu Ile Leu Tyr Lys Val Ile His Tyr Lys Thr Ile Gln Cys
        515                 520                 525

<210> SEQ ID NO 9
<211> LENGTH: 280
<212> TYPE: PRT
<213> ORGANISM: African swine fever virus

<400> SEQUENCE: 9

Met Ser Ser Ser Leu Gln Glu Leu Cys Arg Lys Lys Leu Pro Asp Cys
1               5                   10                  15
Ile Leu Pro Glu Phe Phe Asp Asp Tyr Val Leu Gln Leu Leu Gly Leu
                20                  25                  30
His Trp Gln Asp His Gly Ser Leu Gln Arg Ile Glu Lys Asn Gln Ile
            35                  40                  45
Leu Val Gln Gln Glu Pro Ile His Ile Asn Glu Ala Leu Lys Val Ala
        50                  55                  60
Ala Ser Glu Gly Asn Tyr Glu Ile Val Glu Leu Leu Ser Trp Glu
65                  70                  75                  80
Ala Asp Pro Arg Tyr Ala Val Val Gly Ala Leu Glu Ser Lys Tyr Tyr
                85                  90                  95
Asp Leu Val Tyr Lys Tyr Asp Leu Val Lys Asp Cys His Asp Ile
                100                 105                 110
Leu Pro Leu Ile Gln Asn Pro Glu Thr Phe Glu Lys Cys His Glu Leu
            115                 120                 125
Asn Asn Pro Cys Ser Leu Lys Cys Leu Phe Lys His Ala Val Ile His
130                 135                 140
Asp Met Leu Pro Ile Leu Gln Lys Tyr Thr Tyr Phe Leu Asp Gly Trp
145                 150                 155                 160
Glu Tyr Cys Asn Gln Met Leu Phe Glu Leu Ala Cys Ser Lys Lys Lys
                165                 170                 175
Tyr Glu Met Val Val Trp Ile Glu Gly Val Leu Gly Ile Gly Lys Val
                180                 185                 190
Thr Ser Leu Phe Thr Ile Ala Ile Ser Asn Arg Asp Leu His Leu Tyr
            195                 200                 205
Ser Leu Gly His Leu Ile Ile Leu Glu Arg Met Gln Ser Cys Gly Gln
        210                 215                 220
Asp Pro Thr Phe Leu Leu Asn His Phe Leu Arg Asp Val Ser Ile Lys
225                 230                 235                 240
Gly Leu Leu Pro Phe Val Leu Lys Thr Ile Glu Tyr Gly Gly Ser Lys
                245                 250                 255
Glu Ile Ala Ile Thr Leu Ala Lys Lys Tyr Gln His Lys His Ile Leu
                260                 265                 270
Lys Tyr Phe Glu Thr Gly Lys Cys
        275                 280

<210> SEQ ID NO 10
```

```
<211> LENGTH: 505
<212> TYPE: PRT
<213> ORGANISM: African swine fever virus

<400> SEQUENCE: 10
```

| | | | | | | | | | | | | | | |
|---|---|---|---|---|---|---|---|---|---|---|---|---|---|---|
| Met | Phe | Ser | Leu | Gln | Asp | Ile | Cys | Arg | Lys | Tyr | Leu | Phe | Gln | Leu | Pro |
| 1 | | | | 5 | | | | | 10 | | | | | 15 | |

Asp Ser Phe Asp Glu Tyr Thr Leu Gln Val Leu Gly Leu Tyr Trp Glu
            20                  25                  30

Lys His Gly Ser Leu Gln Arg Ile Arg Lys Asp Ala Val Phe Val Gln
        35                  40                  45

Arg Asn Leu Ile Ile Ser Ile Asn Glu Ala Leu Arg Ile Ala Ala Ser
    50                  55                  60

Glu Gly Asn Gly Arg Val Val Lys Leu Leu Ser Trp Glu Gly Asn
65                  70                  75                  80

Phe His Tyr Val Ile Ile Gly Ala Leu Glu Gly Asp His Tyr Asp Leu
                85                  90                  95

Ile His Lys Tyr Gly Ser Gln Ile Glu Asp Tyr His Met Ile Leu Ser
            100                 105                 110

Ser Ile His Asn Ala Asn Thr Phe Glu Lys Cys His Glu Leu Ser Asn
        115                 120                 125

Cys Asp Met Trp Cys Leu Ile Gln Asn Ala Ile Lys Tyr Asn Met Leu
130                 135                 140

Pro Ile Leu Gln Lys His Arg Asn Ile Leu Thr His Glu Gly Glu Asn
145                 150                 155                 160

Gln Glu Leu Phe Glu Met Ala Cys Glu Glu Gln Lys Tyr Asp Ile Val
                165                 170                 175

Leu Trp Ile Gly Gln Thr Leu Met Leu Asn Glu Pro Glu Phe Ile Phe
            180                 185                 190

Asp Ile Ala Phe Glu Arg Ile Asp Phe Ser Leu Leu Thr Met Gly Tyr
        195                 200                 205

Ser Leu Leu Phe Asn Asn Lys Met Ser Ser Ile Asp Ile His Asp Glu
    210                 215                 220

Glu Asp Leu Ile Ser Leu Leu Thr Glu His Leu Glu Lys Ala Ala Thr
225                 230                 235                 240

Lys Gly Cys Phe Phe Phe Met Leu Glu Thr Leu Lys His Gly Gly Asn
                245                 250                 255

Val Asn Met Ala Val Leu Ser Lys Ala Val Glu Tyr Asn His Arg Lys
            260                 265                 270

Ile Leu Asp Tyr Phe Ile Arg Gln Lys Cys Leu Ser Arg Lys Asp Ile
        275                 280                 285

Glu Lys Leu Leu Leu Val Ala Ile Ser Asn Ser Ala Ser Lys Lys Thr
    290                 295                 300

Leu Asn Leu Leu Leu Ser Tyr Leu Asn His Ser Val Lys Asn Ile Ile
305                 310                 315                 320

Gly Lys Ile Val Gln Ser Val Leu Lys Asn Gly Asp Phe Thr Ile Ile
                325                 330                 335

Ile Phe Leu Lys Lys Lys Ile Asn Leu Val Glu Pro Ala Leu Ile
            340                 345                 350

Gly Phe Ile Asn Tyr Tyr Ser Tyr Cys Phe Leu Glu Gln Phe Ile
        355                 360                 365

His Glu Phe Asp Ile Arg Pro Glu Lys Met Ile Lys Met Ala Ala Arg
    370                 375                 380

Lys Gly Lys Leu Asn Met Ile Ile Glu Phe Leu Asn Glu Lys Tyr Val

```
                385                 390                 395                 400
His Lys Asp Asp Leu Gly Ala Ile Phe Lys Phe Leu Lys Asn Leu Val
                    405                 410                 415

Cys Thr Met Lys His Lys Gly Lys Glu Thr Leu Ile Val Leu Ile
                    420                 425                 430

His Lys Ile Tyr Gln Val Ile Gln Leu Glu Thr Lys Glu Lys Phe Lys
                    435                 440                 445

Leu Leu Arg Phe Tyr Val Met His Asp Ala Thr Ile Gln Phe Ile Ser
                    450                 455                 460

Met Tyr Lys Asp Cys Phe Asn Leu Ala Gly Phe Lys Pro Phe Leu Leu
465                 470                 475                 480

Glu Cys Leu Asp Ile Ala Ile Lys Lys Asn Tyr Pro Asp Met Ile Arg
                    485                 490                 495

Asn Ile Glu Thr Leu Leu Lys Cys Glu
                    500                 505

<210> SEQ ID NO 11
<211> LENGTH: 254
<212> TYPE: PRT
<213> ORGANISM: African swine fever virus

<400> SEQUENCE: 11

Met Gln Asn Lys Ile Pro Asn Phe Asn Leu Phe Phe Phe Leu Tyr
1               5                   10                  15

Arg Met Leu Glu Ile Val Leu Ala Thr Leu Leu Gly Asp Leu Gln Arg
                20                  25                  30

Leu Arg Val Leu Thr Pro Gln Gln Arg Ala Val Ala Phe Phe Arg Ala
            35                  40                  45

Asn Thr Lys Glu Leu Glu Asp Phe Leu Arg Ser Asp Gly Gln Ser Glu
        50                  55                  60

Glu Ile Leu Ser Gly Pro Leu Leu Asn Arg Leu Leu Glu Pro Ser Cys
65                  70                  75                  80

Pro Leu Asp Ile Leu Thr Gly Tyr His Leu Phe Arg Gln Asn Pro Lys
                85                  90                  95

Ala Gly Gln Leu Arg Gly Leu Glu Val Lys Met Leu Glu Arg Leu Tyr
            100                 105                 110

Asp Ala Asn Ile Tyr Asn Ile Leu Ser Arg Leu Arg Pro Lys Lys Val
        115                 120                 125

Arg Asn Lys Ala Ile Glu Leu Tyr Trp Val Phe Arg Ala Ile His Ile
130                 135                 140

Cys His Ala Pro Leu Val Leu Asp Ile Val Arg Tyr Glu Glu Pro Asp
145                 150                 155                 160

Phe Ala Glu Leu Ala Phe Ile Cys Ala Ala Tyr Phe Gly Glu Pro Gln
                165                 170                 175

Val Met Tyr Leu Leu Tyr Lys Tyr Met Pro Leu Thr Arg Ala Val Leu
            180                 185                 190

Thr Asp Ala Ile Gln Ile Ser Leu Glu Ser Asn Asn Gln Val Gly Ile
        195                 200                 205

Cys Tyr Ala Tyr Leu Met Gly Gly Ser Leu Lys Gly Leu Val Ser Ala
210                 215                 220

Pro Leu Arg Lys Arg Leu Arg Ala Lys Leu Arg Ser Gln Arg Lys Lys
225                 230                 235                 240

Lys Asp Val Leu Ser Pro His Asp Phe Leu Leu Leu Leu Gln
                245                 250
```

<210> SEQ ID NO 12
<211> LENGTH: 148
<212> TYPE: PRT
<213> ORGANISM: African swine fever virus

<400> SEQUENCE: 12

```
Met Leu Glu Arg Leu Tyr Asp Ala Asn Ile Tyr Asn Ile Leu Ser Arg
1               5                   10                  15

Leu Arg Pro Glu Lys Val Arg Asn Lys Ala Val Glu Leu Tyr Trp Val
            20                  25                  30

Phe Arg Ala Ile Asn Met Cys His Ala Pro Leu Val Leu Asp Ile Val
        35                  40                  45

Arg Tyr Glu Glu Pro Asp Phe Ala Glu Leu Ala Phe Ile Cys Ala Ala
    50                  55                  60

Tyr Phe Gly Glu Pro Gln Val Met Tyr Leu Leu Tyr Lys Tyr Met Pro
65                  70                  75                  80

Leu Thr Arg Ala Val Leu Thr Asp Ala Ile Gln Ile Ser Leu Glu Ser
                85                  90                  95

Asn Ser Gln Val Gly Ile Cys Tyr Ala Tyr Leu Met Gly Gly Ser Leu
            100                 105                 110

Lys Gly Leu Val Arg Ala Pro Leu Arg Lys Arg Leu Arg Ala Lys Leu
        115                 120                 125

Arg Ser Gln Arg Lys Lys Asp Val Leu Pro Pro His Asp Phe Leu
    130                 135                 140

Leu Leu Leu Gln
145
```

<210> SEQ ID NO 13
<211> LENGTH: 151
<212> TYPE: PRT
<213> ORGANISM: African swine fever virus

<400> SEQUENCE: 13

```
Met Leu Glu Arg Leu Tyr Asp Ala Asn Ile Tyr Asn Met Leu Ala Arg
1               5                   10                  15

Leu Arg Pro Glu Leu Val Arg Asp Lys Ala Ile Glu Leu Tyr Trp Leu
            20                  25                  30

Phe Arg Ala Ile Leu Met Cys His Ser Pro Leu Val Leu Glu Ile Val
        35                  40                  45

Arg His Glu Thr Met Asp Phe Ala Glu Thr Ala Phe Ile Cys Ala Ala
    50                  55                  60

Tyr Phe Ser Glu Pro Gln Val Met Tyr Ala Leu Tyr Lys Phe Ile Pro
65                  70                  75                  80

Ile Ser Arg Ala Val Leu Ala Asp Ala Ile Gln Met Cys Leu Glu Ser
                85                  90                  95

Asn Ser Glu Ala Gly Ile Cys Tyr Ala Tyr Leu Met Gly Gly Ser Leu
            100                 105                 110

Lys Gly Lys Val Pro Gly Ser Leu Arg Lys Arg Leu Arg Ala Ser Pro
        115                 120                 125

Leu Arg Gln Glu Arg Lys Lys Lys Asn Val Leu Pro Pro His Glu Phe
    130                 135                 140

Leu Leu Met Leu His Gly Ile
145                 150
```

<210> SEQ ID NO 14
<211> LENGTH: 219

<212> TYPE: PRT
<213> ORGANISM: African swine fever virus

<400> SEQUENCE: 14

```
Met Gln Arg Ala Val Ala Phe Phe Arg Val Asn Thr Lys Glu Leu Glu
1               5                   10                  15

Asp Phe Leu Tyr Pro Asp Gly Gln Ser Glu Glu Leu Leu Pro Gly Leu
            20                  25                  30

Leu Leu Asn Arg Leu Leu Glu Pro Ser Gly Pro Ile Asp Ile Leu Thr
        35                  40                  45

Gly Tyr His Leu Phe Arg Glu Asn Pro Lys Ala Gly Arg Leu Arg Gly
    50                  55                  60

Leu Glu Val Lys Leu Leu Glu Arg Leu Tyr Asp Ala Asn Ile Tyr Asn
65                  70                  75                  80

Met Leu Ala Gln Ile Arg Pro Glu Leu Val Arg Ile Lys Ala Ile Glu
                85                  90                  95

Leu Tyr Trp Leu Phe Arg Ala Ile Leu Met Cys His Ser Pro Leu Val
            100                 105                 110

Leu Glu Ile Val Arg His Glu Thr Met Asp Phe Ala Glu Leu Ala Phe
        115                 120                 125

Ile Cys Ala Ala Tyr Phe Ser Glu Pro Gln Val Met Tyr Ala Leu Tyr
    130                 135                 140

Lys Phe Ile Pro Ile Ser Arg Ala Val Leu Ala Asp Ala Ile Glu Met
145                 150                 155                 160

Ser Leu Glu Ser Asn Ser Glu Thr Gly Ile Cys Tyr Ala Tyr Leu Met
                165                 170                 175

Gly Gly Ser Leu Lys Gly Lys Val Pro Gly Pro Leu Arg Lys Arg Leu
            180                 185                 190

Arg Ala Ser Pro Leu Arg Gln Glu Arg Lys Lys Lys Asn Val Leu Pro
        195                 200                 205

Pro His Glu Phe Leu Leu Met Leu His Gly Ile
    210                 215
```

<210> SEQ ID NO 15
<211> LENGTH: 254
<212> TYPE: PRT
<213> ORGANISM: African swine fever virus

<400> SEQUENCE: 15

```
Met Gln Asn Lys Ile Pro Asn Phe Asn Leu Phe Phe Phe Leu Tyr
1               5                   10                  15

Arg Met Leu Glu Ile Val Leu Ala Thr Leu Leu Gly Asp Leu Gln Arg
            20                  25                  30

Leu Arg Val Leu Thr Pro Gln Gln Arg Ala Val Ala Phe Phe Arg Ala
        35                  40                  45

Asn Thr Lys Glu Leu Glu Asp Phe Leu Cys Ser Asp Gly Gln Ser Glu
    50                  55                  60

Glu Ile Leu Ser Gly Pro Leu Leu Asn Arg Leu Leu Glu Pro Ser Gly
65                  70                  75                  80

Pro Leu Asp Ile Leu Thr Gly Tyr His Leu Phe Arg Gln Asn Pro Lys
                85                  90                  95

Ala Gly Gln Leu Arg Gly Leu Glu Val Lys Met Leu Glu Arg Leu Tyr
            100                 105                 110

Asp Ala Asn Ile Tyr Asn Ile Leu Ser Arg Leu Arg Pro Glu Lys Val
        115                 120                 125
```

```
Arg Asn Lys Ala Ile Glu Leu Tyr Trp Val Phe Arg Ala Ile His Ile
    130                 135                 140

Cys His Ala Pro Leu Val Leu Asp Ile Val Arg Tyr Glu Glu Pro Asp
145                 150                 155                 160

Phe Ala Glu Leu Ala Phe Ile Cys Ala Ala Tyr Phe Gly Pro Gln
                165                 170                 175

Val Met Tyr Leu Leu Tyr Lys Tyr Met Pro Leu Thr Arg Ala Val Leu
                180                 185                 190

Thr Asp Ala Ile Arg Ile Ser Leu Glu Ser Asn Asn Gln Val Gly Ile
                195                 200                 205

Cys Tyr Ala Tyr Leu Met Gly Gly Ser Leu Lys Gly Leu Val Ser Ala
210                 215                 220

Pro Leu Arg Lys Arg Leu Cys Ala Lys Leu Arg Ser Gln Arg Lys Lys
225                 230                 235                 240

Lys Asp Val Leu Ser Pro His Asp Phe Leu Leu Leu Gln
                245                 250

<210> SEQ ID NO 16
<211> LENGTH: 148
<212> TYPE: PRT
<213> ORGANISM: African swine fever virus

<400> SEQUENCE: 16

Met Leu Glu Arg Leu Tyr Asp Ala Asn Ile Tyr Asn Ile Leu Ser Arg
1               5                   10                  15

Leu Arg Pro Glu Lys Val Arg Asn Lys Ala Val Glu Leu Tyr Trp Val
                20                  25                  30

Phe Arg Ala Ile Asn Met Cys His Ala Pro Leu Val Leu Asp Ile Val
            35                  40                  45

Arg Tyr Glu Glu Pro Asp Phe Ala Glu Leu Ala Phe Ile Cys Ala Ala
        50                  55                  60

Tyr Phe Gly Glu Pro Gln Val Met Tyr Leu Leu Tyr Lys Tyr Met Pro
65                  70                  75                  80

Leu Ser Arg Ala Val Leu Thr Asp Ala Ile Gln Ile Ser Leu Glu Ser
                85                  90                  95

Asn Ser Gln Val Gly Ile Cys Tyr Ala Tyr Leu Met Gly Gly Ser Leu
                100                 105                 110

Lys Gly Leu Val Arg Ala Pro Leu Arg Lys Arg Leu Arg Ala Lys Leu
            115                 120                 125

Arg Ser Gln Arg Lys Lys Lys Asp Val Leu Pro Pro His Asp Phe Leu
        130                 135                 140

Leu Leu Leu Gln
145

<210> SEQ ID NO 17
<211> LENGTH: 148
<212> TYPE: PRT
<213> ORGANISM: African swine fever virus

<400> SEQUENCE: 17

Met Leu Glu Arg Leu Tyr Asp Ala Asn Ile Tyr Asn Ile Leu Ser Arg
1               5                   10                  15

Leu Arg Pro Glu Lys Val Arg Asn Lys Ala Val Glu Leu Tyr Trp Val
                20                  25                  30

Phe Arg Ala Ile Asn Met Cys His Ala Pro Leu Val Leu Asp Ile Val
            35                  40                  45
```

```
Arg Asn Glu Glu Leu Asp Phe Ala Glu Leu Ala Phe Ile Cys Ala Ala
    50                  55                  60

Tyr Phe Gly Glu Pro Gln Val Met Tyr Leu Leu Tyr Lys Tyr Met Pro
65                  70                  75                  80

Leu Thr Arg Ala Val Leu Thr Asp Ala Ile Gln Ile Ser Leu Glu Ser
                85                  90                  95

Asn Ser Gln Val Gly Ile Cys Tyr Ala Tyr Leu Met Gly Gly Ser Leu
            100                 105                 110

Lys Gly Leu Val Arg Ala Pro Leu Arg Lys Arg Leu Arg Ala Lys Leu
        115                 120                 125

Arg Ser Gln Arg Lys Lys Asp Val Leu Pro Pro His Asp Phe Leu
    130                 135                 140

Leu Leu Leu Gln
145

<210> SEQ ID NO 18
<211> LENGTH: 148
<212> TYPE: PRT
<213> ORGANISM: African swine fever virus

<400> SEQUENCE: 18

Met Leu Glu Arg Leu Tyr Asp Ala Asn Ile Tyr Asn Ile Leu Ser Arg
1               5                   10                  15

Leu Arg Pro Glu Lys Val Arg Asn Lys Ala Ile Glu Leu Tyr Trp Val
            20                  25                  30

Phe Arg Ala Ile His Ile Cys His Ala Pro Leu Val Leu Asp Ile Val
        35                  40                  45

Arg Tyr Glu Glu Pro Asp Phe Ala Glu Leu Ala Phe Ile Cys Ala Ala
    50                  55                  60

Tyr Phe Gly Glu Pro Gln Val Met Tyr Leu Leu Tyr Lys Tyr Met Pro
65                  70                  75                  80

Leu Thr Arg Ala Val Leu Thr Asp Ala Ile Arg Ile Ser Leu Glu Ser
                85                  90                  95

Asn Asn Gln Val Gly Ile Cys Tyr Ala Tyr Leu Met Gly Gly Ser Leu
            100                 105                 110

Lys Gly Leu Val Ser Ala Pro Leu Arg Lys Arg Leu Arg Ala Lys Leu
        115                 120                 125

Arg Ser Gln Arg Lys Lys Asp Val Leu Ser Pro His Asp Phe Leu
    130                 135                 140

Leu Leu Leu Gln
145

<210> SEQ ID NO 19
<211> LENGTH: 148
<212> TYPE: PRT
<213> ORGANISM: African swine fever virus

<400> SEQUENCE: 19

Met Leu Glu Arg Leu Tyr Asp Ala Asn Ile Tyr Asn Ile Leu Ser Arg
1               5                   10                  15

Leu Arg Pro Glu Lys Val Arg Asn Lys Ala Ile Glu Leu Tyr Trp Val
            20                  25                  30

Phe Arg Ala Ile His Ile Cys His Ala Pro Leu Val Leu Asp Ile Val
        35                  40                  45

Arg Tyr Glu Glu Pro Asp Phe Ala Glu Leu Ala Phe Ile Cys Ala Ala
    50                  55                  60
```

```
Tyr Phe Gly Glu Pro Gln Val Met Tyr Leu Leu Tyr Lys Tyr Met Pro
 65                  70                  75                  80

Leu Thr Arg Ala Val Leu Thr Asp Ala Ile Gln Ile Ser Leu Glu Ser
                 85                  90                  95

Asn Asn Gln Val Gly Ile Cys Tyr Ala Tyr Leu Met Gly Gly Ser Leu
            100                 105                 110

Lys Gly Leu Val Ser Ala Pro Leu Arg Lys Arg Leu Arg Ala Lys Leu
        115                 120                 125

Arg Ser Gln Arg Lys Lys Lys Asp Val Leu Ser Pro His Asp Phe Leu
    130                 135                 140

Leu Leu Leu Gln
145

<210> SEQ ID NO 20
<211> LENGTH: 36
<212> TYPE: DNA
<213> ORGANISM: Artificial Sequence
<220> FEATURE:
<223> OTHER INFORMATION: Primer FlankLF

<400> SEQUENCE: 20
acgttgcaaa gcttccatta atccctccag ttgttc                         36

<210> SEQ ID NO 21
<211> LENGTH: 36
<212> TYPE: DNA
<213> ORGANISM: Artificial Sequence
<220> FEATURE:
<223> OTHER INFORMATION: Primer Flank LR

<400> SEQUENCE: 21
acgttgcagg tacccctctc tctgcagact ctcacc                         36

<210> SEQ ID NO 22
<211> LENGTH: 36
<212> TYPE: DNA
<213> ORGANISM: Artificial Sequence
<220> FEATURE:
<223> OTHER INFORMATION: Primer Flank RF

<400> SEQUENCE: 22
acgttgcagc ggccgcctct ccaagacatc tgtcgg                         36

<210> SEQ ID NO 23
<211> LENGTH: 40
<212> TYPE: DNA
<213> ORGANISM: Artificial Sequence
<220> FEATURE:
<223> OTHER INFORMATION: Primer Flank RR

<400> SEQUENCE: 23
acgtacgtct cgagcctcac atgccatctc aaacaattcc                     40

<210> SEQ ID NO 24
<211> LENGTH: 22
<212> TYPE: DNA
<213> ORGANISM: Artificial Sequence
<220> FEATURE:
<223> OTHER INFORMATION: Primer BeninD8F

<400> SEQUENCE: 24
ggtgagagtc tgcagagaga gg                                        22
```

```
<210> SEQ ID NO 25
<211> LENGTH: 18
<212> TYPE: DNA
<213> ORGANISM: Artificial Sequence
<220> FEATURE:
<223> OTHER INFORMATION: Primer BeninD8R

<400> SEQUENCE: 25
gccctagcac ttgtaacg                                                 18

<210> SEQ ID NO 26
<211> LENGTH: 27
<212> TYPE: DNA
<213> ORGANISM: Artificial Sequence
<220> FEATURE:
<223> OTHER INFORMATION: Primer RGUS

<400> SEQUENCE: 26
ccttctctgc cgtttccaaa tcgccgc                                       27

<210> SEQ ID NO 27
<211> LENGTH: 18
<212> TYPE: DNA
<213> ORGANISM: Artificial Sequence
<220> FEATURE:
<223> OTHER INFORMATION: Primer BeninD8INTF

<400> SEQUENCE: 27
cgatgtatca ttgatgtc                                                 18

<210> SEQ ID NO 28
<211> LENGTH: 19
<212> TYPE: DNA
<213> ORGANISM: Artificial Sequence
<220> FEATURE:
<223> OTHER INFORMATION: Primer BeninD8INTR

<400> SEQUENCE: 28
ggataatctt agggaggcc                                                19

<210> SEQ ID NO 29
<211> LENGTH: 19
<212> TYPE: DNA
<213> ORGANISM: Artificial Sequence
<220> FEATURE:
<223> OTHER INFORMATION: Primer 9LF

<400> SEQUENCE: 29
atgacgcatt aaaccggcg                                                19

<210> SEQ ID NO 30
<211> LENGTH: 20
<212> TYPE: DNA
<213> ORGANISM: Artificial Sequence
<220> FEATURE:
<223> OTHER INFORMATION: Primer 4RR

<400> SEQUENCE: 30
cagtatagcc ctagcacttg                                               20

<210> SEQ ID NO 31
<211> LENGTH: 96
<212> TYPE: DNA
<213> ORGANISM: Artificial Sequence
<220> FEATURE:
<223> OTHER INFORMATION: Recombinant virus sequence (left flank of
      deletion/insertion)
```

<400> SEQUENCE: 31

```
agagagggt accatttaat aaaaacaata aattattttt tataacatta tatataactt    60
tgtatagcat acattatacg aagttatatg ttacgt                             96
```

<210> SEQ ID NO 32
<211> LENGTH: 96
<212> TYPE: DNA
<213> ORGANISM: African swine fever virus

<400> SEQUENCE: 32

```
agagaggacc atatttcttt ttttgaaaaa atcaaattaa aaaaaaacat gcttgtttgg    60
catacatgta actatgttat aaccatgtta taacca                             96
```

<210> SEQ ID NO 33
<211> LENGTH: 73
<212> TYPE: DNA
<213> ORGANISM: Artificial Sequence
<220> FEATURE:
<223> OTHER INFORMATION: Recombinant virus sequence (right flank of
      deletion/insertion)

<400> SEQUENCE: 33

```
cagccaggga ggcaaacaat gaggaattct gcagatatcc atcactggcg gccgcctctc    60
caagacatct tgt                                                      73
```

<210> SEQ ID NO 34
<211> LENGTH: 77
<212> TYPE: DNA
<213> ORGANISM: African swine fever virus

<400> SEQUENCE: 34

```
ttttatcata cattaaaatt ccagtaaaat ttatattttt tttggtaaac aaatgttttc    60
tctccaagac atcttgt                                                  77
```

<210> SEQ ID NO 35
<211> LENGTH: 2160
<212> TYPE: DNA
<213> ORGANISM: African swine fever virus

<400> SEQUENCE: 35

```
aaatgaatag atttaatcca agtagtatta aaattttta gaaatagtgt tctacaaata     60
atgaaatgaa tagcccaaaa aaaataaggt gtacattaat gtaatatatt gttaggctaa   120
gtaaatttaa tatttaaagt acttggaaaa atatttttta acatatgctg tctaggaatt   180
tttttagaca tttaaaacca tatagttact ttatttatta cacttaactt gaaaagaatt   240
attgcctaaa atattaatag atgaagtaat attgtgtaat tgagtccata acatgggtgg   300
gaaacaaaaa tctcgtaata tgaaaaataa acatcctaaa aagagtgcaa ttgttataag   360
tttatgtaac tttattttaa agtaagaata taaaaatatg agtacaagag aatagggc    420 cattactaat attggctcca acatcctgtt gtctacaaaa aaaatatttt ttttggcaaa   480
aaaaaatcca tggaaggata ttaatacaca taattgtttg acatcatatt ggtatactta   540
ccaaatagta atatacaacc atcctaatat tcactttatg aaatgacccc ccccccacc    600 tatacagtaa aatagtatag gttttaataa agaaaaaaga tattatgtag ttttatttt    660 tgtatagtgc gtgaatgcaa aataaaatcc caaatttaa cctttctttt tttttctat    720 acaggatgtt agaaatagta ttggcaacgc tgctaggcga cctgcagcgg ctccgggttc   780
```

```
ttacccctca gcagcgggcg gttgccttct ttcgagccaa tactaaggag ctagaggact    840
tcttacgctc agatgggcaa tctgaggaga tactgtctgg ccccctcctt aaccgtctac    900
tagaaccctc atgccctctt gatattttaa ccggatatca cctatttcgt cagaatccca    960
aggcaggtca gttgcgcggc cttgaggtca agatgcttga acggttatac gatgctaata   1020
tttacaatat attgtctcgg ctgcgaccta aaaagtccg caacaaggct attgagctat    1080
actgggtttt ccgagctatc catatttgtc atgctccttt agtttagat attgtacgat    1140 atgaggaacc ggactttgct gaactggcct ttatttgtgc tgcttacttt ggtgaacctc   1200
aggtaatgta tttgctctac aaatatatgc ctctgacccg cgcagttctt acggatgcca   1260
tccagataag tcttgagagc aacaaccagg tagggatttg ctatgcttac ttgatgggag   1320
gcagcctcaa gggactagtc tccgccccac tgcgtaaacg tctgcgcgcc aaactacgct   1380
cgcagcgcaa aagaaggac gttctttcac cccacgactt cttactgctg ctccagtagc    1440 ttttttgcc gcaggagcac cgtggatagg agctcctcca cgctcgcgat ccggcgctgg    1500
aagcggaacc gatcgaccgc cacctgctcc cagggaccct tgcgctcgat gtcgtcggct   1560 tcccataccct cgacggctgc agcaaagcgg acgtgcttcg tgtcattcgt ccgttttttg   1620
cgccgccgcc ccccccccat tattcctgta agattagtgt ttaataccta taataacata   1680
attttaagat ttaatatacc aaaacttaaa ctattttttgt atagtaacta ttagcatgtc   1740
tacacatgat tgttttttcaa aagagaaacc agttgatatg aacgatatat ctgagaaatc   1800
atctgtcgtg gataatgcac ccgagaaacc agctggagcg aatcatatac ctgagaagtc   1860
ggcccgcgaa atgacatcat cagaatggat tgctgaatat tggaaaggta taaaacgtgg   1920
aaatgacgtg ccatgttgtt gtccaagaaa aatgaccagt gcagacaaaa agttttcagt   1980
atttggtaag ggatccctaa tacgctccat ccagaagaat aattaaaaaa atatttttt    2040 ttggtaagtt tataaactat atagttaaat atggtaaaaa aaatcacata ataattaaac   2100
tgaacgtgtt agaattaata tttttttata atcggatata atatccatta aatcaataaa   2160
```

<210> SEQ ID NO 36
<211> LENGTH: 38
<212> TYPE: DNA
<213> ORGANISM: Artificial Sequence
<220> FEATURE:
<223> OTHER INFORMATION: Primer 360-18RFlankL-for-Benin

<400> SEQUENCE: 36
gctatccaag cttctacaaa taatgaaatg aatagccc                            38

<210> SEQ ID NO 37
<211> LENGTH: 38
<212> TYPE: DNA
<213> ORGANISM: Artificial Sequence
<220> FEATURE:
<223> OTHER INFORMATION: Primer 360-18RFlankL-rev-Benin2

<400> SEQUENCE: 37
gctatccggt acccataaag tgaatattag gatggttg                            38

<210> SEQ ID NO 38
<211> LENGTH: 37
<212> TYPE: DNA
<213> ORGANISM: Artificial Sequence
<220> FEATURE:
<223> OTHER INFORMATION: Primer 360-18RFlankR-for

<210> SEQ ID NO 38

<400> SEQUENCE: 38
gctatccgcg gccgccgact tcttactgct gctccag                              37

<210> SEQ ID NO 39
<211> LENGTH: 36
<212> TYPE: DNA
<213> ORGANISM: Artificial Sequence
<220> FEATURE:
<223> OTHER INFORMATION: Primer 360-18RFlankR-rev

<400> SEQUENCE: 39
gctatcctct agatcttctg gatggagcgt attagg                               36

<210> SEQ ID NO 40
<211> LENGTH: 22
<212> TYPE: DNA
<213> ORGANISM: Artificial Sequence
<220> FEATURE:
<223> OTHER INFORMATION: Primer 18R-Benin-Pair1-For

<400> SEQUENCE: 40
gagtacaaga ggaatagggg cc                                              22

<210> SEQ ID NO 41
<211> LENGTH: 23
<212> TYPE: DNA
<213> ORGANISM: Artificial Sequence
<220> FEATURE:
<223> OTHER INFORMATION: Primer 18R-OURT-Pair1-Rev

<400> SEQUENCE: 41
gcatgacaaa tatggatagc tcg                                             23

<210> SEQ ID NO 42
<211> LENGTH: 21
<212> TYPE: DNA
<213> ORGANISM: Artificial Sequence
<220> FEATURE:
<223> OTHER INFORMATION: Primer 18R-OURT-Pair2-For

<400> SEQUENCE: 42
gtccgcaaca aggctattga g                                               21

<210> SEQ ID NO 43
<211> LENGTH: 19
<212> TYPE: DNA
<213> ORGANISM: Artificial Sequence
<220> FEATURE:
<223> OTHER INFORMATION: Primer 18R-OURT-Pair2-Rev

<400> SEQUENCE: 43
gacgtttacg cagtggggc                                                  19

<210> SEQ ID NO 44
<211> LENGTH: 24
<212> TYPE: DNA
<213> ORGANISM: Artificial Sequence
<220> FEATURE:
<223> OTHER INFORMATION: Primer 18R-OURT-Pair3-For

<400> SEQUENCE: 44
caaccaggta gggatttgct atgc                                            24

<210> SEQ ID NO 45
<211> LENGTH: 16

```
<212> TYPE: DNA
<213> ORGANISM: Artificial Sequence
<220> FEATURE:
<223> OTHER INFORMATION: Primer 18R-OURT-Pair3-Rev

<400> SEQUENCE: 45
gctgcagccg tcgagg                                                     16
```

ATTENUATED AFRICAN SWINE FEVER VIRUS VACCINE

CROSS-REFERENCE TO RELATED APPLICATIONS

This application is a Continuation of U.S. patent application Ser. No. 15/319,856, filed Dec. 19, 2019, which is a U.S. National Phase Application of PCT/GB2015/051798, filed Jun. 19, 2015, which claims the priority benefit of Great Britain Patent Application No. 1410971.4, filed Jun. 19, 2014. The entire contents of these applications are incorporated herein by reference in their entirety.

FIELD OF THE INVENTION

The present invention relates to attenuated African Swine Fever Viruses. The engineered viruses protect pigs against subsequent challenge with virulent virus. The present invention also relates to the use of such attenuated viruses to treat and/or prevent African Swine Fever. The invention further relates to intranasal administration of attenuated African Swine Fever Viruses.

BACKGROUND TO THE INVENTION

African Swine Fever (ASF)

African swine fever is a devastating haemorrhagic disease of domestic pigs caused by a double-stranded DNA virus, African swine fever virus (ASFV). ASFV is the only member of the Asfarviridae family and replicates predominantly in the cytoplasm of cells. Virulent strains of ASFV can kill domestic pigs within about 5-14 days of infection with a mortality rate approaching 100%.

ASFV can infect and replicate in warthogs (*Phacochoerus* sp.), bushpigs (*Potamocherus* sp.) and soft ticks of the *Ornithodoros* species, but in these species few if any clinical signs are observed and long term persistent infections can be established. The disease is currently endemic in many sub-Saharan countries and in Europe in Sardinia. Following its introduction to Georgia in the Trans Caucasus region in 2007, ASFV has spread extensively through neighbouring countries including the Russian Federation. In 2012 the first outbreak was reported in Ukraine and in 2013 the first outbreaks in Belarus. In 2014 further outbreaks were reported in pigs in Ukraine and detection in wild boar in Lithuania and Poland.

There is currently no treatment for ASF. Prevention in countries outside Africa has been attempted on a national basis by restrictions on incoming pigs and pork products, compulsory boiling of waste animal products under licence before feeding to pigs and the application of a slaughter policy when the disease is diagnosed. Prevention in Africa is based on measures to keep warthogs and materials contaminated by warthogs away from the herd. To date, no effective attenuated or inactivated vaccines have been developed (see awww.thepigsite.com/pighealth/article/441/african-swine-fever-asf).

There is thus a need for improved measures to control ASFV infection and prevent spread of the disease.

African Swine Fever Virus (ASFV)

The ASFV genome encodes five multigene families (MGF 100, MGF 110, MGF 360 and MGF 505/530) located within the left hand 35 kb or right hand 15 kb terminal variable regions. The MGFs constitute between 17 and 25% of the total coding capacity of the ASFV genome. They lack similarity to other known genes. Although the function of individual MGF genes is unknown, it has been shown the MGF 360 and 505 families encode genes essential for host range function that involves promotion of infected-cell survival and suppression of type I interferon response.

The OURT88/3 Isolate

OURT88/3 is a non-pathogenic isolate of ASFV from Portugal. Previous infection with ASFV OURT88/3 has been shown to confer protection against challenge with related virulent viruses (Boinas et al (2004) J Gen Virol 85:2177-2187; Oura et al (2005) J. Gen. Virol. 86:2445-2450).

It has been demonstrated that CD8+ T cells are required for the protection induced by the OURT88/3 strain, since antibody mediated depletion of CD8+ T cells abrogates protection (Oura et al., 2005, as above).

Studies were carried out using the NIH inbred pig lines cc and dd. In these studies, a control group of 3 dd pigs and a control group of 6 dd pigs were immunised with OURT8813. In the first of these experiments, following OURT88/3 immunisation one dd pig developed a transient low viremia of log 10 2-3 TCID 50/ml, but no fever or clinical signs of disease. It was observed that 3 of 6 of the cc inbred pigs immunised with OURT88/3 were not protected following lethal challenge with OURT88/3 isolate, whereas protective responses were induced in all dd pigs. These results indicate that the genetic background of the pig influences the response to OURT88/3 innoculation.

In subsequent experiments 5 dd and 5 cc pigs were immunised with OURT88/3 and challenged with OURT88/1 (Takamatsu et al., 2003 unpublished results). This confirmed that protective responses were induced in all dd pigs, but not induced in all cc pigs following immunisation with OURT88/3 and that adverse reactions including transient pyrexia, joint swelling and lameness were induced in some of the cc pigs.

Subsequent experiments were carried out in France using the Anses herd of SPF pigs. In these pigs, similar to observations with cc pigs, some pigs developed adverse reactions including transient fever, joint swelling and lameness following immunisation with OURT88/3 (unpublished results).

Although OURT88/3 has been shown to induce a protective immune response in certain animals, this effect does not appear to be universal. Immunisation with OURT88/3 appears to be ineffective in protecting some pigs from subsequent challenge. It is also associated with the induction of adverse immune responses, such as joint swelling, in some pigs.

There is therefore a need for alternative ASFV vaccine candidates with improved efficacy and safety profiles.

DESCRIPTION OF THE FIGURES

FIG. 1—Schematic diagram showing the generation of recombinant virus BeninΔMGF with the deletion of five MGF 360 genes 10L, 11L, 12L, 13L, 14L and the deletion of three MGF 505 genes 1R, 2R, 3R. Recombinant virus BeninΔMGF was created by the homologous recombination between the MGF 360 gene 9L and the MGF 505 4R gene on the wild type Benin 97/1 genome and the transfer vector plasmid pΔMGFGUS resulting in the deletion of the eight MGF genes and the insertion of the GUS marker gene.

FIG. 3—DNA sequence analysis of recombinant virus BeninΔMGF at the deletion/insertion site compared to the published sequence of wild type Benin 97/1. Viral gDNA was isolated from BeninΔMGF infected cells and the left flank of the deletion/insertion was sequenced with primer 9LF and the right flank sequenced with primer 4RR. The left flank sequence of BeninΔMGF shows the insertion of sequences vp72 promoter, loxP and 5' GUS gene and the deletion of eight MGF genes and deletion of the first five nucleotides of the MGF 360 9L gene including the ATG start codon. The right flank sequence of BeninΔMGF shows the insertion of the 3' GUS gene and the deletion of the first seven nucleotides of the MGF 505 4R gene, including the ATG start codon.

FIG. 4—Replication kinetics of Benin 97/1 and recombinant BeninΔMGF viruses. Pig bone marrow macrophages were infected at high multiplicity of infection with parental BeninΔ97/1 or recombinant BeninΔMGF viruses. At various hours post-infection, as indicated on the x-axis, total virus was harvested and infectious virus titrated on 96 well plates by analysis of haemadsorption on cultures of pig bone marrow macrophages. The virus titre ($HAD_{50}$/ml) is the mean of three individual observations.

FIG. 7—IFN-γ ELISPOT assays. Peripheral blood mononuclear cells collected day 20 post first inoculation were stimulated ex vivo with either medium alone, OURT88/3 or BeninΔMGF. Results are shown as IFN-γ production per $10^6$ lymphocytes (y-axis) and pig number (x-axis). Spots per $10^6$ cells produced by PBMC purified on day 20 post inoculation with OUR T88/3 (pigs 16 to 20) or BeninΔMGF (pigs 21 to 25) in a porcine IFNγ ELIspot. Error bars represent standard deviation from the mean of duplicate wells. Dilution 1 contained twice as many cells as dilution 2.

Figure 14:
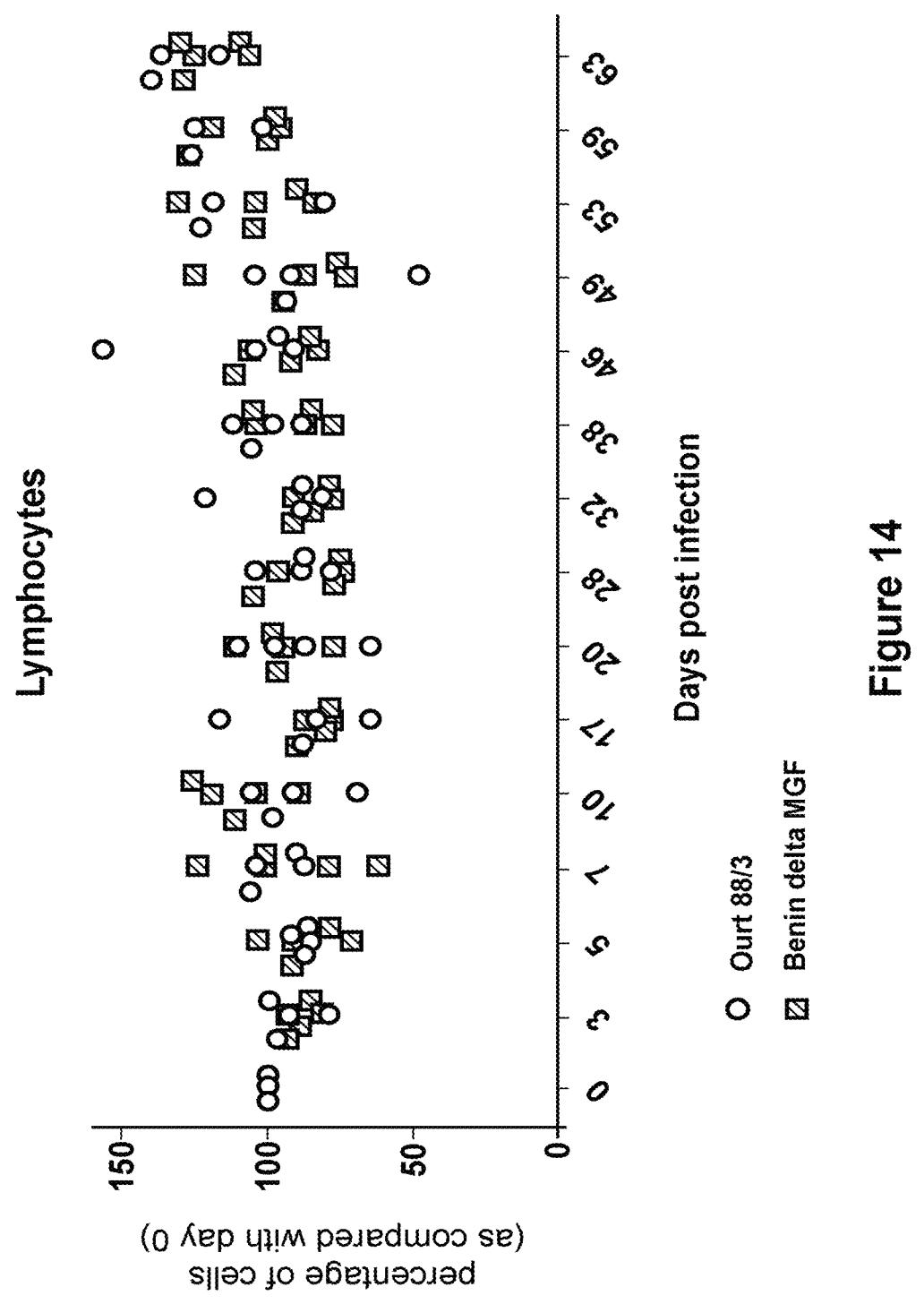

FIG. 14—Percentage of circulating total lymphocytes in peripheral blood samples (as compared with day 0) collected at different days post infection (x-axis) from pigs infected with OURT88/3 (pigs 16 to 20) or BeninΔMGF (pigs 21 to 25).

FIG. 19—Percentage of circulating gamma delta cells in peripheral blood samples (as compared with day 0) collected at different days post infection (x-axis) from pigs infected with OURT88/3 (pigs 16 to 20) or BeninΔMGF (pigs 21 to 25).

FIG. 21A-H—Temperatures of pigs in Example 6 Groups A (FIG. 21A), B (FIG. 21B), C (FIG. 21C), D (FIG. 21D), E (FIG. 21E), F (FIG. 21F) on different days post-immunisation and challenge and of control group G (FIG. 21G) after challenge. FIG. 21H control unvaccinated FIG. 22A-C—Mean temperatures of all pigs in groups A to F of Example 6 after immunisation and challenge are shown in panel A (FIG. 22A). Panel B (FIG. 22B) shows mean temperatures of surviving pigs in groups A to F and panel C (FIG. 22C) temperatures of non-survivors.

FIG. 23A-G—Clinical scores of pigs in Example 6 Groups (FIG. 23A), B (FIG. 23B), C (FIG. 23C), D (FIG. 23D), E (FIG. 23E), F (FIG. 23F) on different days post-immunisation and challenge and of control group G (FIG. 23G) after challenge.

FIG. 27—Shaded in grey is the sequence of the DP148R gene which was deleted from the ASFV genome. The start and stop codons are shown in bold. Sequences used to amplify the left and right flanking regions are underlined. The sequences amplified are between these primers.

FIG. 28—Growth curves of Benin97/1, BeninΔDP148R and BeninΔMGF in porcine alveolar macrophages.

FIG. FIG. 30A-F—Clinical scores of pigs in groups A to E as described for FIG. 29 [e.g., $HAD_{50}$ doses of $10^2$ (FIG. 30A), $10^3$ (FIG. 30B) and $10^4$ (FIG. 30C) using the IM route, $10^3$ $HAD_{50}$ using the intranasal route (FIG. 30D) and BeninΔDP148R at $10^3$ $HAD_{50}$ using IM route (FIG. 30E)] on different days post-immunisation and challenge and of control group F (FIG. 30F) after challenge.

FIG. 32—Mean clinical scores of all pigs in groups A to E as described for FIG. 29 after immunisation and challenge

SUMMARY OF ASPECTS OF THE INVENTION

Figure 2:
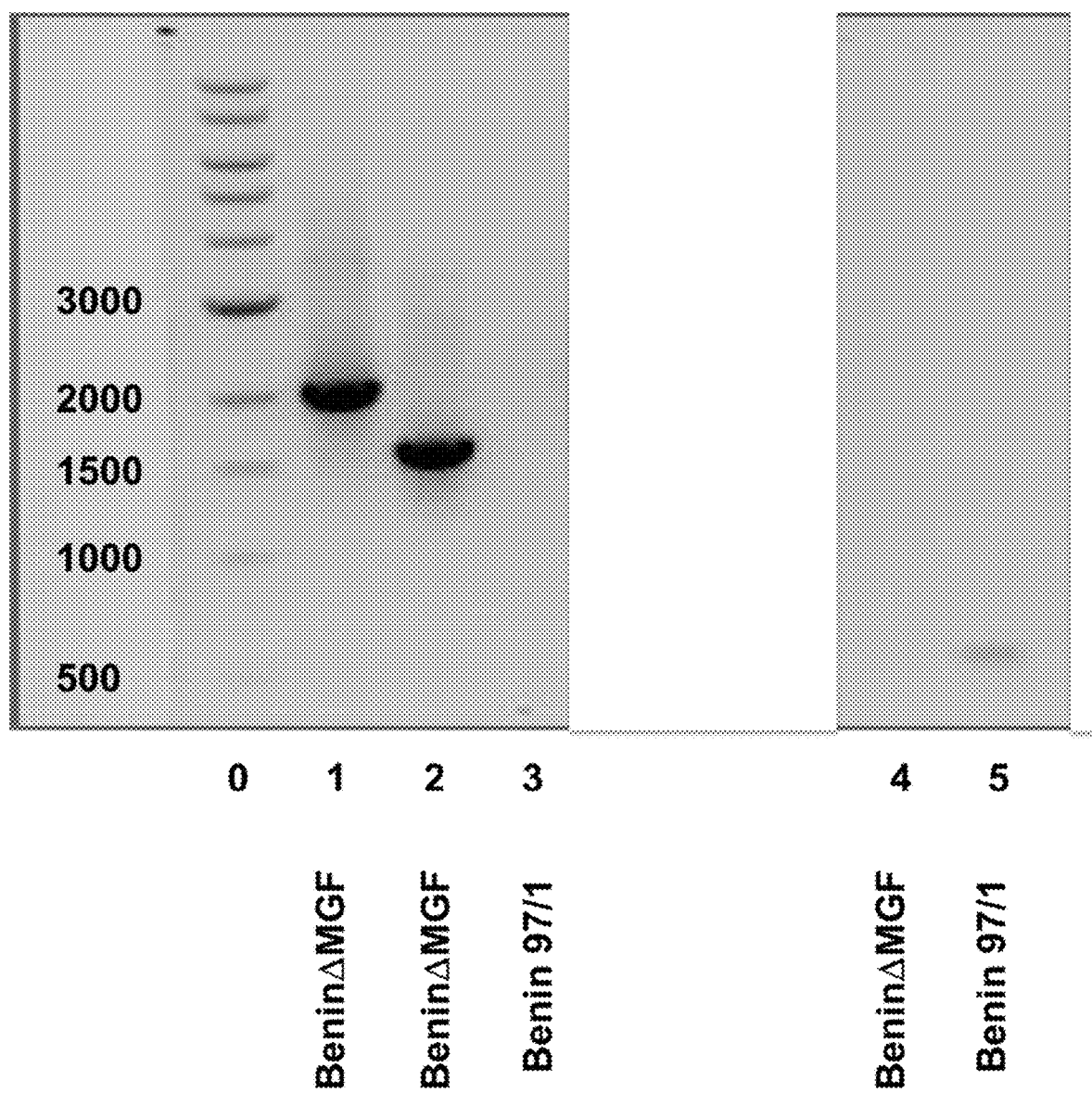
FIG. 2—Analysis of genomic viral DNA gene deletions and insertions by PCR. Viral DNA was extracted from wild type Benin 97/1 and the recombinant virus Benin ΔMGF. Specific fragments were amplified by PCR and the products were analysed on a 1% agarose TAE gel. The following primer sets were used in lane 1 (BeninD8F and BeninD8R), lanes 2 and 3 (BeninD8F and RGUS), lanes 4 and 5 (BeninD8INTF and BeninD8INT). Lane 0 contains a DNA ladder.

The present inventors have surprisingly found that deletion of five multi-gene family (MGF) 360 genes 10L, 11L, 12L, 13L, 14L and three MGF 505 genes 1R, 2R, 3R from the left hand end of the ASF virus genome and interruption of two additional genes (MGF360 9L and MGF 505 4R) resulted in attenuation of a virulent virus and induction of 100% protection against challenge with parental ASFV virulent virus.

Thus, in a first aspect, the present invention provides an attenuated African Swine Fever (ASF) virus which lacks a functional version of the following genes:
  multigene-family 360 genes 9L, 10L 11L, 12L, 13L and 14L; and
  multigene-family 505 genes 1R, 2R, 3R and 4R.

The following genes may be at least partially (i.e. partially or completely) deleted:
  multigene-family 360 genes 10L, 11L, 12L, 13L and 14L; and
  multigene-family 505 genes 1R, 2R and 3R.

The following genes may be interrupted:
  multigene-family 360 gene 9L; and
  multigene-family 505 gene 4R.

The inventors have also surprisingly found that deletion of only one gene, namely the DP148R gene, from a region close to the right end of the virulent Benin97/1 genome, resulted in attenuation of a virulent virus and does not reduce virus replication in macrophages. A group of 5 pigs immunised with BeninΔDP148R intramuscularly with $10^3$ $HAD_{50}$ units developed a transient fever and loss of appetite for 1 or 2 days at day 5 post-immunisation. No further clinical signs were observed following boost 21 days later or at challenge 42 days after the first immunisation. All 5 pigs survived challenge.

Accordingly, the invention further provides an attenuated African Swine Fever (ASF) virus which lacks a functional version of the DP148R gene. The gene may be partially or completely deleted, or interrupted.

The DP148R mutation may also be made in combination with mutation of the multigene-family 360 genes 9L, 10L, 11L, 12L, 13L and 14L and multigene-family 505 genes 1R, 2R, 3R and 4R as described herein. Therefore in one embodiment the invention provides an attenuated African Swine Fever (ASF) virus which lacks a functional version of the following genes:
  multigene-family 360 genes 9L, 10L, 11L, 12L, 13L and 14L;
  multigene-family 505 genes 1R, 2R, 3R and 4R; and
  DP148R.

The virus may be derivable from a virulent ASFV virus isolate. In other words, the genome of the attenuated virus of the invention (other than the genes MGF 360 genes 9L, 10L, 11L, 12L, 13L and 14L, and MGF 505 genes 1R, 2R, 3R and 4R; and/or DP148R) may correspond to the genome of a virulent ASFV virus isolate. The attenuated virus of the invention may be made by deleting/interrupting the genes: MGF 360 genes 9L, 10L, 11L, 12L, 13L and 14L and MGF 505 genes 1R, 2R, 3R and 4R; and/or DP148R; from a virulent ASFV virus isolate.

The virus may be derivable from one of the following virulent ASFV virus isolates: Georgia 2007/1, Benin 97/1, Kenyan, Malawi Lil20/1, Pretorisuskop/96/4 and Tengani 62.

The virus may be derivable from Benin 97/1.

The attenuated ASF virus, when administered to a subject, may induce an immune response which is protective against subsequent challenge with virulent ASF virus.

The attenuated ASF virus, when administered to a subject, may induce a reduced T cell mediated immune response compared to the immune response induced by attenuated virus OURT88/3. The immune response may involve a lower number of CD8+ positive γδT cells In a second aspect, the present invention provides a vaccine comprising an attenuated ASF virus according to the first aspect of the invention.

The vaccine may comprise a plurality of attenuated ASF viruses of different genotypes.

In a third aspect, the present invention provides a vaccine according to the second aspect of the invention for use in treating and/or preventing African Swine Fever.

The vaccine may induce a cross-protective immune response against a plurality of ASF virus genotypes.

In a fourth aspect, the present invention provides a method of attenuating an African Swine Fever (ASF) virus, which comprises the step of partially or completely deleting, or interrupting the expression of, the following genes:
  multigene-family 360 genes 9L, 10L, 11L, 12L, 13L and 14L; and
  multigene-family 505 genes 1R, 2R, 3R and 4R.

The following genes may be partially or completely deleted:
multigene-family 360 genes 10L, 11L, 12L, 13L and 14L; and
multigene-family 505 genes 1R, 2R and 3R.
The following genes may be interrupted:
multigene-family 360 gene 9L; and
multigene-family 505 gene 4R.

The invention further provides a method of attenuating an African Swine Fever (ASF) virus, which comprises the step of partially or completely deleting, or interrupting the expression of, the DP148R gene.

In a fifth aspect the present invention provides a method for treating and/or preventing African Swine Fever in a subject which comprises the step of administering to the subject an effective amount of a vaccine according to the second aspect of the invention.

The subject may, for example, be a domestic pig.

The vaccine may be administered following a prime-boost regime.

The engineered virus BeninΔMGF of the present invention has several advantages over OURT88/3, for example:
It is effective in inducing a protective immune response in a greater proportion of pigs than OURT88/3
It has an improved safety profile compared with OURT88/3 and does not induce adverse immunological reactions such as joint swelling.
It is more efficient and is effective at a lower dose than OURT88/3
It induces a "better" type of immune response than OURT88/3, as OURT88/3 induces a much higher IFNγ response. BeninΔMGF has a reduced T cell mediated response than OURT88/3.

The engineered virus BeninΔDP148R of the present invention also has several advantages over OURT88/3 for example:
It has an improved safety profile compared with OURT88/3 since no pulmonary, musculoskeletal or gross lesions were observed at post-mortem examination.
It has higher efficacy than OURT88/3 since 100% of pigs tested were protected against Benin 97/1 challenge.

The present inventors have furthermore surprisingly found that intranasal administration of an attenuated African Swine Fever (ASF) virus results in improved protection and fewer side effects compared to administration via the intramuscular route, and may require a lower dose to obtain protection.

Accordingly, in a sixth aspect the present invention provides an attenuated ASF virus for use in the treatment and/or prevention of African Swine Fever, wherein the attenuated virus is administered intranasally.

The invention further provides a method for treating and/or preventing African Swine Fever in a subject which comprises the step of administering an effective amount of an attenuated ASF virus to the subject by the intranasal route.

The invention also relates to a vaccine comprising an attenuated ASF virus, wherein the vaccine is formulated for intranasal administration.

Further provided is a kit for delivery of an intranasal vaccine formulation comprising:
a) an attenuated ASF virus vaccine; and
b) an intranasal delivery device.

The invention also provides an intranasal delivery device comprising an attenuated ASF virus vaccine.

The attenuated ASF virus may be any attenuated ASF virus, such as OURT88/13, BeninΔMGF or BeninΔDP148R.

DETAILED DESCRIPTION

African Swine Fever Virus (ASFV)

African swine fever virus (ASFV) is the causative agent of African swine fever (ASF). The virus causes a haemorrhagic fever with high mortality rates in pigs, but persistently infects its natural hosts, warthogs, bushpigs with no disease signs. It also infects soft ticks of the *Ornithodoros* genus, which are thought to be used as a vector.

ASFV replicates in the cytoplasm of infected cells, and is the only member of the Asfarviridae family. ASFV is endemic to sub-Saharan Africa and exists in the wild through a cycle of infection between ticks and wild pigs, bushpigs and warthogs. ASFV was first described after European settlers brought pigs into areas endemic with ASFV and, as such, is an example of an 'emerging infection'.

ASFV is a large, icosahedral, double-stranded DNA virus with a linear genome containing at least 150 genes. The number of genes differs slightly between different isolates of the virus. ASFV has similarities to the other large DNA viruses, e.g., poxvirus, iridovirus and mimivirus. In common with other viral haemorrhagic fevers, the main target cells for replication are those of monocyte, macrophage lineage.

Based on sequence variation in the C-terminal region of the B646L gene encoding the major capsid protein p72, 22 ASFV genotypes (i-XXII) have been identified. All ASFV p72 genotypes have been circulating in eastern and southern Africa. Genotype I has been circulating in Europe, South America, the Caribbean and western Africa. Genotype VIII is confined to four East African countries.

Examples of strains from some of the genotypes are given below:

Genotype I: OURT88/3; Brazil/79; Lisbon/60; BA715; Pret; Benin 97/1; IC/1/96; IC/576; CAM/82; Madrid/62; Malta78; ZAR85; Katange63; Togo; Dakar59; Ourt88/1; BEN/1/97; Dom_Rep; VAL/76; 10/2/96; Awoshie/99; NIG/1/99; NIG/1/98; ANG/70; BEL/85; SPEC120; Lisbon/57; ASFV-Warm; GHA/1/00; GAM/1/00; Ghana; HO186; NAM/1/80; NUR/90/1; CAM/4/85; ASFV-Teng; Tegani; ASFV-E75.

Genotype II: Georgia 2007/1
Genotype III: BOT 1/99
Genotype IV: ASFV-War; RSA/1/99,
Genotype VI: MOZ 94/1
Genotype VII: VICT/90/1; ASFV-Mku; RSA/1/98
Genotype VIII: NDA/1/90; KAL88/1; ZAM/2/84; JON89/13; KAV89/1; DEZda; AFSV-Mal; Malawi LIL 20/1
Gentoype IX: UGA/95
Genotype X: BUR/1/84; BUR/2/84; BUR/90/1; UGA/3/95; TAN/Kwh12; HindeII; ASFV-Ken; Virulent Uganda 65.

Multigene Families

ASFV contains five multi-gene families which are present in the left and right variable regions of the genome. The MGFs are named after the average number of codons present in each gene: MGF100, 110, 300, 360 and 505/530. The N-terminal regions of members of MGFs 300, 360 and 505/530 share significant similarity with each other. Several genes in MGF360 and 505/530 determine host range and virulence.

The five multigene families of the ASFV genome (MGF 100, MGF 110, MGF 360 and MGF 505/530) are located within the left hand 35 kb or right hand 15 kb terminal variable regions. The MGFs constititute between 17 and 25% of the total coding capacity of the ASFV genome. They lack similarity to other known genes.

The complete genome sequences of isolate Benin 97/1 (a highly pathogenic virus from West Africa, Group 1), isolate OURT88/3 (non-pathogenic, attenuated virus from Portugal, Group 1) and isolate BA71V (Vero cell tissue culture adapted non-pathogenic virus, Group 1) have been compared (Chapman et al (2008) J. Gen Virol. 89:397-408). The isolate OURT88/3 has a deletion of 10007 bp compared to Benin 97/1 extending from nucleotide number (nt no.) 19448 to nt no. 29525 in the Benin 97/1 genome. In all, five MGF 360 genes (10L, 11L, 12L, 13L and 14L) are deleted from the OURT88/3 genome. Two MGF 505 genes (1R, 2R) are deleted and the MGF 505R 3R gene is truncated in the OURT88/3 genome. These genes are present in the genomes of all eight other pathogenic isolates of ASFV that have been sequenced.

In the attenuated tissue-culture adapted BA71V isolate, the genome contains the MGF 505 3R gene but lacks the other seven MGF genes and in addition also has the MGF 360 9L gene truncated (total deletion of 8250 bp).

Previously six MGF 360 genes (9L, 10L, 11L, 12L, 13L and 14L) and two MGF 505 genes (1R and 2R) were deleted from the highly pathogenic South African isolate Pr4. This deletion markedly reduced viral growth in primary macrophage cell cultures by 100- to 1000-fold (Zsak et al 2001, as above) and led to attenuation of the virus (cited as unpublished results, Afonso et al 2004 J. Virol. 78:1858-1864). However no experiments were carried out to challenge the recovered pigs to determine if they were protected. In fact, at an African swine fever virus workshop at the Biosecurity Research Institute, Manhattan Kansas in May 2011 it was mentioned that the Pr4 deletion mutant was not protective and induced a chronic form of the disease.

It has also been shown that deletion of three MGF 360 genes (12L, 13L and 14L) and four MGF 505 genes (1R, 2R, 3R and 4R truncation) from the pathogenic virus MalawiΔDP71 reduces virus replication in pigs and in addition attenuated the virus (Neilan et al (2002) J. Virol. 76:3095-3104). However again, no experiments were reported to determine if the recovered pigs were protected against challenge.

The attenuated ASFV according to one embodiment of the present invention lacks a functional version of the following genes:

multigene-family 360 genes 9L, 10L, 11L, 12L, 13L and 14L; and multigene-family 505 genes 1R, 2R, 3R and 4R.

The location of these genes in the genomes of a variety of ASFV strains is provided below (Table 1). The sequence identity of each gene to the corresponding Benin 97/1 gene is also provided.

TABLE 1

| Strain | Start Nucleotide Number | Stop Nucleotide number | % Nucleotide Identity |
| --- | --- | --- | --- |
| MGF 360-9L | | | |
| Benin 97/1 | 19487 | 18435 | 100 |
| Georgia 2007/1 | 25215 | 24163 | 98 |
| BA71V | 17495 | 17057 | 100 |
| OURT88/3 | 20355 | 19937 | 99 |
| Kenya 1950 | 29478 | 28424 | 86 |
| Malawi-Lil/20 | 23685 | 22630 | 86 |
| Mkuzi 1979 | 26939 | 25887 | 99 |
| Pretorisuskop/96/4 | 26016 | 24958 | 85 |
| Tengani 62 | 20398 | 19346 | 98 |
| Warmbaths | 25244 | 24186 | 86 |
| Warthog | 22020 | 20962 | 85 |
| E75 | 18802 | 17750 | 99 |
| MGF 360-10L | | | |
| Benin 97/1 | 20677 | 19607 | 100 |
| Georgia 2007/1 | 26438 | 25368 | 93 |
| BA71V | Deleted | | |
| OURT88/3 | Deleted | | |
| Kenya 1950 | 30628 | 29563 | 82 |
| Malawi-Lil/20 | 24802 | 23763 | 91 |
| Mkuzi 1979 | 28139 | 27069 | 99 |
| Pretorisuskop/96/4 | 27186 | 26116 | 96 |
| Tengani 62 | 21600 | 20530 | 92 |
| Warmbaths | 26361 | 25322 | 94 |
| Warthog | 23130 | 22091 | 95 |
| E75 | 19981 | 18911 | 100 |
| MGF 360-11L | | | |
| Benin 97/1 | 21764 | 20703 | 100 |
| Georgia 2007/1 | 27526 | 26465 | 97 |
| BA71V | Deleted | | |
| OURT88/3 | Deleted | | |
| Kenya 1950 | 31716 | 30655 | 84 |
| Malawi-Lil/20 | 25892 | 24831 | 86 |
| Mkuzi 1979 | 29225 | 28164 | 99 |
| Pretorisuskop/96/4 | 28275 | 27214 | 97 |
| Tengani 62 | 22688 | 21627 | 97 |
| Warmbaths | 27449 | 26388 | 97 |
| Warthog | 24218 | 23157 | 97 |
| E75 | 21068 | 20007 | 100 |

TABLE 1-continued

| Strain | Start Nucleotide Number | Stop Nucleotide number | % Nucleotide Identity |
|---|---|---|---|
| MGF 360-12L | | | |
| Benin 97/1 | 24668 | 23616 | 100 |
| Georgia 2007/1 | 30434 | 29382 | 96 |
| BA71V | Deleted | | |
| OURT88/3 | Deleted | | |
| Kenya 1950 | 34566 | 33549 | 90 |
| Malawi-Lil/20 | 28731 | 27682 | 92 |
| Mkuzi 1979 | 32125 | 31073 | 97 |
| Pretorisuskop/96/4 | 31150 | 30098 | 95 |
| Tengani 62 | 25592 | 24540 | 96 |
| Warmbaths | 30346 | 29294 | 96 |
| Warthog | 27088 | 26035 | 96 |
| E75 | 23971 | 22920 | 99 |
| MGF 360-13L | | | |
| Benin 97/1 | 25901 | 24840 | 100 |
| Georgia 2007/1 | 31656 | 30595 | 97 |
| BA71V | Deleted | | |
| OURT88/3 | Deleted | | |
| Kenya 1950 | 35812 | 34757 | 90 |
| Malawi-Lil/20 | 29980 | 28925 | 91 |
| Mkuzi 1979 | 33347 | 32286 | 99 |
| Pretorisuskop/96/4 | 32368 | 31307 | 95 |
| Tengani 62 | 26814 | 25753 | 95 |
| Warmbaths | 31559 | 30498 | 95 |
| Warthog | 28338 | 27277 | 95 |
| E75 | 25204 | 24143 | 99 |
| MGF 360-14L | | | |
| Benin 97/1 | 27146 | 26073 | 100 |
| Georgia 2007/1 | 32913 | 31840 | 99 |
| BA71V | Deleted | | |
| OURT88/3 | Deleted | | |
| Kenya 1950 | 37194 | 36121 | 92 |
| Malawi-Lil/20 | 31266 | 30193 | 92 |
| Mkuzi 1979 | 34620 | 33547 | 99 |
| Pretorisuskop/96/4 | 33598 | 32525 | 97 |
| Tengani 62 | 28056 | 26983 | 97 |
| Warmbaths | 32820 | 31747 | 96 |
| Warthog | 29568 | 28495 | 97 |
| E75 | 26449 | 25376 | 100 |
| MGF 505-1R | | | |
| Benin 97/1 | 21971 | 23566 | 100 |
| Georgia 2007/1 | 27734 | 29329 | 95 |
| BA71V | Deleted | | |
| OURT88/3 | Deleted | | |
| Kenya 1950 | 31904 | 33496 | 91 |
| Malawi-Lil/20 | 26041 | 27627 | 93 |
| Mkuzi 1979 | 29425 | 31020 | 96 |
| Pretorisuskop/96/4 | 28449 | 30044 | 94 |
| Tengani 62 | 22891 | 24486 | 95 |
| Warmbaths | 27651 | 29246 | 95 |
| Warthog | 24387 | 25982 | 95 |
| E75 | 21275 | 22870 | 100 |
| MGF 505-2R | | | |
| Benin 97/1 | 27352 | 28932 | 100 |
| Georgia 2007/1 | 33119 | 34699 | 99 |
| BA71V | 17725 | 19304 | 99 |
| OURT88/3 | 29532 | 29981 | 76 |
| Kenya 1950 | 37419 | 38985 | 90 |
| Malawi-Lil/20 | 31541 | 33121 | 93 |
| Mkuzi 1979 | 34826 | 36406 | 99 |
| Pretorisuskop/96/4 | 33795 | 35374 | 97 |
| Tengani 62 | 26261 | 29830 | 98 |
| Warmbaths | 33029 | 34597 | 96 |
| Warthog | 29773 | 31352 | 97 |
| E75 | 26655 | 28236 | 99 |
| MGF 505-3R | | | |
| Benin 97/1 | 29019 | 29861 | 100 |
| Georgia 2007/1 | 34786 | 35625 | 96 |
| BA71V | 20398 | 21915 | 100 |
| OURT88/3 | 20850 | 22367 | 100 |
| Kenya 1950 | 40295 | 41815 | 89 |
| Malawi-Lil/20 | 34322 | 35842 | 89 |

TABLE 1-continued

| Strain | Start Nucleotide Number | Stop Nucleotide number | % Nucleotide Identity |
|---|---|---|---|
| Mkuzi 1979 | 37500 | 39017 | 99 |
| Pretorisuskop/96/4 | 36480 | 37985 | 89 |
| Tengani 62 | 30926 | 32443 | 90 |
| Warmbaths | 35712 | 37232 | 93 |
| Warthog | 32449 | 33954 | 90 |
| E75 | 29330 | 30847 | 100 |
| MGF 505-4R | | | |
| Benin 97/1 | 30026 | 31543 | 100 |
| Georgia 2007/1 | 35796 | 37316 | 94 |
| BA71V | 20394 | 21915 | 100 |
| OURT88/3 | 20850 | 22367 | 100 |
| Kenya 1950 | 40295 | 41815 | 89 |
| Malawi-Lil/20 | 34322 | 35842 | 89 |
| Mkuzi 1979 | 37500 | 39017 | 99 |
| Pretorisuskop/96/4 | 36480 | 37985 | 89 |
| Tengani 62 | 30926 | 32443 | 90 |
| Warmbaths | 35712 | 37232 | 93 |
| Warthog | 32449 | 33954 | 90 |
| E75 | 29330 | 30847 | 100 |

The translation products of these genes are given below:

translation of 360-9L
SEQ ID No. 1
MVLSLQTLTKKVLASQYPAKCHPHFLKCCGLWWHNGPIMYHQKKIWTPYFK
NGINLNAALVKAVEENNHDLIELFTEWGANINYGLLSVNTEHTRDLCRQLG
AKEQLNDQEILRFFYTLKRDLTSSNIIFCHEVFSNNPILDTINRFEVKGMI
YEQLEGLMVETDILSEMFTKYWYAMAIEFNLKEAICYFYQRYAHLHRWRLM
CALFYNNVFDLHELYAKEKVRMDMDEMLRWACRKNYNYLTIYYCCVALGAD
INQAMFHSIQFYNIGNIFFCIDLGANAFEEGKTLAHQKDNSFIASMLSLNC
YSMNDSLSLKETDPEVIKRMLKDYHSKNLSIAHKHYINDGFNDI translation of 360-10L
SEQ ID No. 2
MVPSLQSFAKKVLASQHVSIDYHVILERCGLWWYKAPISLDCKHMLIKLPN
FADGLDLNTALMLATKENNYQLIKMFTDWGADINYGLICANTPPIREFCWE
LGAKYQVDKKKIMHIFFKLIHPNTTSNNIILCLKFFNDNPFSAYVIIREIK
SCHIHWKLKNLAEDTNVLSNISDGDMLTIYCFIVALQDNLREAISYVYQHF
KYLNTWWLTCALCYNKLFDLHNLYEKEKIRMDMDEMMRIACTKDNNFLTIY
YCFILGANINLAMIASIRFYNMDNLFFCIDLGADAFEEAKALAEQQNYYLI
SHRLSLDIYSPDSSLLTLKEADPNKIYRLLKNYKSKSMLAYLNYDINDTSL translation of 360-11L
SEQ ID No. 3
MLPSLQSLTKKVLAGQCVSVDHYHILKCCGLWWHNGPIMLHIRRNKLFIRS
TCFSQGIELNIGLMKAVKENNHDLIKLFTEWGADINYGMICALTENTRDLC
KELGAKEYLEREYILKIFFDTTRDKTSSNIIFCHEVFSNNPNLRIIDNLDL
RGEIMWELRGLMEITFMLDHDDSFSTVLTKYWYAIAVDYDLKDAIRYFYQK
YPRLHRWRLMCALFYNNVFDLHELYEIERVRMDIDEMMHIACIQDYSYSAI
YYCFIMGANINQAMLVSIQNYNLGNLFFCIDLGANAFEEGKALAEQKENYL
IAHALSLKHYNPVISLLSNVMDPEKINYMLKNYHSINMGIFLDYEQR translation of 360-12L
SEQ ID No. 4
MLPSLQSLTKKVLAGQCVPTNQHYLLKYYDLWWYNAPITFDHNL
RLIKSSGIKEGLDLNTALVKAVRENNYSLIKLFTEWGADINYGLVSVNTEH
TRDLCELGAKEILNEEEILQIFIDLKFHKISSNIILCHEVFSNNPILQKVN
NLKLRIEIFWELRELIEKTDLLNNEFLLSTLLLKYWYAIAVRYSLKEAIQY
FYQKYTHMNTWRLTCALCFNNVFDLHEAYEKDKIHMDIEEMMRIACIKDHN
LSTMYYCYMLGANINQAMLTSIQYYNIENMFFCMDLGADVFEEGTTALGEG
YELIKNILSLKIYSPTTIPLPKSTDPEIIDHALKNYFSKNMMIFLSYDLR translation of 360-13L
SEQ ID No 5
MSLPLSLQTLVKKTVASQCLSIDEHCILKYCGLWWHDAPLKLCMDRGRIQI
KSGFLGEDIDLRVALIIAVKENNYSLIKLFTEWGANINYSLLSINTKHIRE
LCRQLGAKETLEDNDIFRIFTRIMHNKTSGSIILCHEIFMNNPMLENKFVI
QLRGLIYKRLWGLIEIKETDELNDLLVKYWYAKAVQYVCKNAICFLDEKYT
DLNEWRLKCLLYYNKIYELHEMYHKKKVQIDVHDMICLACAKDNNLLTIYY
CYALGGNINQAMLTSVQYYNVGNIFFCIDLGGNAFEEGRAIAEQKGYNFLS
HSLTLDIYSSDASLPLNLKDPEKISSLLKDYKSKNLSIIWEYSHNIL translation of 360-14L
SEQ ID No. 6
MLSLQTLAKKVVACNYLSSDYDYTLQRFGLWWDLGPIHLCNNCK
QVFSYKHLQCFSEDDLCLEAALVKAVKSDNLELIRLFVDWGANPEYGLIRV
PAVYLKRLCAELGGLTPVSEPRLLEILKEVANLKSCAGVLLGYDMFCHNPL
LETVTRTTLDTVTYTCSNIPLTGDTAHLLLTKFWFALALRHNFTKAIHYFY
KRHKNQLYWRVACSLYFNNIFDIHELCREKEICISPNLMMKFACLREKNYA
AIYYCHRLGASLDYGMNLSIYNNNTLNMFFCIDLGAADFDRAQLIAHKAYM
YNLSNIFLVKQLFSRDVTLVLDVTEPQEIYDMLKTYTSKNMKRAEEYLTAH
PEIIVID translation of 505-1R SEQ ID No. 7

MFSLQNLCRKTLPDCKLPEFFDDYILQLLGLYWENHGTIQRAGNNCVLIQQ

HTLIPVNEALRIAASEENYEIVGLLLAWEGNLYYAIIGALEGNRYNLIRKY

DDQIKDHHDILPFIDDPIIFHKCHIMRRCFFDCILYQAVKYSKFRVLLYFK

YTLEDDLPLVHLLIEKACEDHNYEVIKWIYENLHVCHIIDTFDCAIAHKDL

RLYCLGYTFIYNRIVPYKYHHLDILILSSLQLLHKVAAKGYLDFILETLKY

DHNIDNLDVILTQAATYNHRKILTYFIPQSTYAQIEQCLFVAIKTKSSKKT

LNLLLSHLNLSIKLIQKISQYVATFNSTNIIGILSMKRKKKIYLDIILTKF

VKNAIFNKFVVRCMERFSINPERIVKMAARINKMMLVKKISEHVWKNHAAR

LKHLKHAVHTMKHKDGKNRLMNFIYEHCYYHMQGEEIFSLARFYAIHHAPK

LFDVFYNCCILDTIRFKSLLLDCSHIIGKNAHDATNINIVNKYIGNLFAMG

VLSKKEILQDYPSIYSKHYMP translation of 505-2R

SEQ ID No. 8

MFSLQDLCRKHLFILPDVFGEHVLQRLGLYWRCHGSLQRIGDDHILIRRDL

ILSTNEALRMAGEEGNNEVVKLLLLWKGNLHYAVIGALQGDQYDLIHKYEN

QIGDFHFILPLIQDANTFEKCHALERFCGVSCLLKHATKYNNALPILQKYQ

EELSMRAYLHETLFELACLWQRYDVLKWIEQTMHVYDLKIMFNIAISKRDL

TMYSLGYIFLFDRGNTEATLLTQHLEKTAAKGLLHFVLETLKYGGNIDTVL

TQAVKYNHRKLLDYFLRQLPRKHIEKLLLLAVQEKASKKTLNLLLSHLNYS

VKIRIKKLLRYVIEYESTLVIKILLKKRVNLIDAMLEKMVRYFSATKVRTI

MDELSISPERVIKMAIQKMRTDIVIHTSYVWEDDLERLTRLKNMVYTIKYE

HGKKMLIKVMHGIYKNLLYGEREKVMFHLAKLYVAQNAATQFRDICKDCYK

LDVARFKPRFKQLILDCLEIVTKKSCYSILEILEKHIISLFTMKVMTEEEK

NLCLEILYKVIHYKTIQC translation of 505-3R

SEQ ID No. 9

MSSSLQELCRKKLPDCILPEFFDDYVLQLLGLHWQDHGSLQRIE

KNQILVQQEPIHINEALKVAASEGNYEIVELLLSWEADPRYAVVGALESKY

YDLVYKYYDLVKDCHDILPLIQNPETFEKCHELNNPCSLKCLFKHAVIHDM

LPILQKYTYFLDGWEYCNQMLFELACSKKKYEMVVWIEGVLGIGKVTSLFT

IAISNRDLHLYSLGHLIILERMQSCGQDPTFLLNHFLRDVSIKGLLPFVLK

TIEYGGSKEIAITLAKKYQHKILKYFETGKC translation of 505-4R

SEQ ID No. 10

MFSLQDICRKYLFQLPDSFDEYTLQVLGLYWEKHGSLQRIRKDA

VFVQRNLIISINEALRIAASEGNGRVVKLLLSWEGNFHYVIIGALEGDHYD

LIHKYGSQIEDYHMILSSIHNANTFEKCHELSNCDMWCLIQNAIKYNMLPI

LQKHRNILTHEGENQELFEMACEEQKYDIVLWIGQTLMLNEPEFIFDIAFE

RIDFSLLTMGYSLLFNNKMSSIDIHDEEDLISLLTEHLEKAATKGCFFFML

ETLKHGGNVNMAVLSKAVEYNHRKILDYFIRQKCLSRKDIEKLLLVAISNS

ASKKTLNLLLSYLNHSVKNIIGKIVQSVLKNGDFTIIIFLKKKKINLVEPA

LIGFINYYYSYCFLEQFIHEFDIRPEKMIKMAARKGKLNMIIEFLNEKYVH

KDDLGAIFKFLKNLVCTMIKHKKGKETLIVLIHKIYQVIQLETKEKFKLLR

FYVMHDATIQFISMYKDCFNLAGFKPFLLECLDIAIKKNYPDMIRNIETLL

KCE

The complete genome for the African swine fever virus Benin 97/1 pathogenic isolate is given in Genbank Locus: AM712239.1

From the study described by Chapman et al (2008—as above) it was determined that the complete BA71 isolate genome encodes 151 open reading frames (ORFs), the Benin 97/1 isolate encodes 157 ORFs and the OURT88/3 isolate encodes 151 ORFs.

According to another embodiment of the invention, there is provided an attenuated ASFV which lacks a functional version of gene DP148R.

The DP148R mutation may be made on its own, or in combination with mutations of the multigene-family 360 genes 9L, 10L, 11L, 12L, 13L and 14L. and multigene-family 505 genes 1R, 2R, 3R and 4R as described herein. This combination of gene mutations may result in a better safety profile for the attenuated virus.

DP148R is located at genome position 177915 to 178679 on the Benin 97/1 genome. The protein sequence is:

Benin 97/1 177915-178679

SEQ ID No. 11

MQNKIPNFNLFFFFLYRMLEIVLATLLGDLQRLRVLTPQQRAVAFFRANTK

ELEDFLRSDGQSEEILSGPLLNRLLEPSCPLDILTGYHLFRQNPKAGQLRG

LEVKMLERLYDANIYNILSRLRPKKVRNKAIELYWVFRAIHICHAPLVLDI

VRYEEPDFAELAFICAAYFGEPQVMYLLYKYMPLTRAVLTDAIQISLESNN

QVGICYAYLMGGSLKGLVSAPLRKRLRAKLRSQRKKKDVLSPHDFLLLLQ.

Orthologous DP148R sequences from other genomes share between 74 and 99% amino acid identity. The orthologous DP148R genes from other ASFV isolates are located in positions:

Warthog: 181103 to 181549

SEQ ID No. 12

MLERLYDANIYNILSRLRPEKVRNKAVELYWVFRAINMCHAPLVLDIVRYE

EPDFAELAFICAAYFGEPQVMYLLYKYMPLTRAVLTDAIQISLESNSQVGI

CYAYLMGGSLKGLVRAPLRKRLRAKLRSQRKKKDVLPPHDFLLLLQ

Kenya: 189417 to 189872

SEQ ID No. 13

MLERLYDANIYNMLARLRPELVRDKAIELYWLFRAILMCHSPLVLEIVRHE

TMDFAETAFICAAYFSEPQVMYALYKFIPISRAVLADAIQMCLESNSEAGI

CYAYLMGGSLKGKVPGSLRKRLRASPLRQERKKKNVLPPHEFLLMLHGI

Malawi LIL20/1: 183687 to 184346

SEQ ID No. 14

MQRAVAFFRVNTKELEDFLYPDGQSEELLPGLLLNRLLEPSGPIDILTGYH

LFRENPKAGRLRGLEVKLLERLYDANIYNMLAQIRPELVRIKAIELYWLFR

AILMCHSPLVLEIVRHETMDFAELAFICAAYFSEPQVMYALYKFIPISRAV

LADAIEMSLESNSETGICYAYLMGGSLKGKVPGPLRKRLRASPLRQERKKK

NVLPPHEFLLMLHGI

-continued

Mkuzi: 185751 to 186515
SEQ ID No. 15
MQNKIPNFNLFFFFLYRMLEIVLATLLGDLQRLRVLTPQQRAVAFFRANTK

ELEDFLCSDGQSEEILSGPLLNRLLEPSGPLDILTGYHLFRQNPKAGQLRG

LEVKMLERLYDANIYNILSRLRPEKVRNKAIELYWVFRAIHICHAPLVLDI

VRYEEPDFAELAFICAAYFGEPQVMYLLYKYMPLTRAVLTDAIRISLESNN

QVGICYAYLMGGSLKGLVSAPLRKRLCAKLRSQRKKKDVLSPHDFLLLLQ

Pretoriskup: 185416 to 185862
SEQ ID No. 16
MLERLYDANIYNILSRLRPEKVRNKAVELYWVFRAINMCHAPLVLDIVRYE

EPDFAELAFICAAYFGEPQVMYLLYKYMPLSRAVLTDAIQISLESNSQVGI

CYAYLMGGSLKGLVRAPLRKRLRAKLRSQRKKKDVLPPHDFLLLLQ

Tengani: 180112 to 180558
SEQ ID No. 17
MLERLYDANIYNILSRLRPEKVRNKAVELYWVFRAINMCHAPLVLDIVRNE

ELDFAELAFICAAYFGEPQVMYLLYKYMPLTRAVLTDAIQISLESNSQVGI

CYAYLMGGSLKGLVRAPLRKRLRAKLRSQRKKKDVLPPHDFLLLLQ

Warmbaths: 184606 to 185052
SEQ ID No. 18
MLERLYDANIYNILSRLRPEKVRNKAIELYWVFRAIHICHAPLVLDIVRYE

EPDFAELAFICAAYFGEPQVMYLLYKYMPLTRAVLTDAIRISLESNNQVGI

CYAYLMGGSLKGLVSAPLRKRLRAKLRSQRKKKDVLSPHDFLLLLQ

OURT88/3: 169146 to 169592
SEQ ID No, 19
MLERLYDANIYNILSRLRPEKVRNKAIELYWVFRAIHICHAPLVLDIVRYE

EPDFAELAFICAAYFGEPQVMYLLYKYMPLTRAVLTDAIQISLESNNQVGI

CYAYLMGGSLKGLVSAPLRKRLRAKLRSQRKKKDVLSPHDFLLLLQ

ASF Virus Isolates

The attenuated ASF virus of the present invention may be derivable from a wild-type ASF virus isolate, but includes mutations in its genome such that the following genes are completely or partially deleted or otherwise made non-functional: MGF 360 genes 9L, 10L, 11L, 12L, 13L and 14L and MGF 505 genes 1R, 2R, 3R and 4R; and/or DP148R gene.

The term "wild-type" indicates that the virus existed (at some point) in the field, and was isolated from a natural host, such as a domestic pig, tick or wart hog. Table 2 below lists known ASF virus isolates.

The genome structure of ASFVs is known in the art, as detailed in Chapman et al (2008) J. Gen. Virol. 89:397-408.

The term "corresponds to" means that the remainder of the genome is the same, or substantially the same, as the wild type strain. Thus the genome of the attenuated virus of the present invention may include the genes of the wild type strain, other than MGF 360 genes 9L, 10L, 11L, 12L, 13L and 14L and MGF 505 genes 1R, 2R, 3R and 4R; and/or DP148R gene.

The genome of the attenuated virus may comprise the ORFs conserved in all 10 genome sequences available and completely or partially deleted or otherwise made non-functional: MGF 360 genes 9L, 10L, 11L, 12L, 13L and 14L and MGF 505 genes 1R, 2R, 3R and 4R; and/or DP148R gene.

The genome of the attenuated recombinant ASF virus of the invention may correspond to that of a virulent ASF virus strain (with the exception of the MGF 360 genes 9L, 10L, 11L, 12L, 13L and 14L and MGF 505 genes 1R, 2R, 3R and 4R; and/or DP148R gene).

African swine fever virus isolates described to date are summarised in Table 2, together with their Genbank Accession numbers.

Known virulent ASF virus strains include: Georgia 2007/1, Benin 97/i, Kenyan, Malawi Li120/1, Pretorisuskop/96/4 and Tengani 62.

TABLE 2

| Isolate | Country | Host | Year | Virulence | GenBank accession No |
|---|---|---|---|---|---|
| Georgia 2007/1 | Georgia | Domestic pig | 2007 | High | FR862468 |
| BA71qqV | Spain | Domestic pig | 1971 | Tissue culture adapted | U18466 |
| Benin 97/1 | Spain | Domestic pig | 1997 | High | AM712239 |
| OURT88/3 | Portugal | Tick | 1988 | Low | AM712240 |
| Kenya | Kenya | Domestic pig | 1950 | High | AY261360 |
| Malawi Lil20/1 | Malawi | Tick | 1983 | High | AY261361 |
| Mkuzi | Zululand | Tick | 1978 | Unknown | AY261362 |
| Pretorisuskop/96/4 | South Africa | Tick | 1996 | High | AY261363 |
| Tangani 62 | Malawi | Domestic pig | 1962 | High | AY261364 |
| Warmbaths | South Africa | Tick | 1987 | Unknown | AY261365 |
| Warthog | Namibia | Warthog | 1980 | Unknown | AY261366 |

The genome of the attenuated recombinant ASF virus of the invention (with the exception of the MGF 360 genes 9L, 10L, 11L, 12L, 13L and 14L and MGF 505 genes 1R, 2R, 3R and 4R; and/or DP148R gene) may correspond to that of the Benin 97/1 isolate.

The genome of the attenuated recombinant ASF virus of the invention (with the exception of the MGF 360 genes 9L, 10L, 11L, 12L, 13L and 14L and MGF 505 genes 1R, 2R, 3R and 4R, and/or DP148R) may correspond to that of an ASF virus strain whose virulence is currently unknown, for example: Mkuzi, Warmbaths and Warthog.

The present invention also provides a vaccine composition which comprises a plurality of attenuated ASF viruses. The plurality of attenuated ASF viruses may correspond to a plurality of different isolates, for example, different isolates of high or unknown virulence.

Such a vaccine composition may elicit a cross-protective immune response to several or substantially all ASF viruses.

Deletions

The attenuated African Swine Fever (ASF) virus of one embodiment of the present invention lacks a functional version of the following genes:
multigene-family 360 genes 9L, 10L, 11L, 12L, 13L and 14L; and
multigene-family 505 genes 1R, 2R, 3R and 4R.

The genes may, for example, be wholly or partially deleted.

In particular, the following genes may be at least partially deleted:
multigene-family 360 genes 10L, 11L, 12L, 13L and 14L; and
multigene-family 505 genes 1R, 2R and 3R.

In another embodiment, the present invention provides an attenuated ASFV which lacks a functional version of DP148R. The gene may be wholly or partially deleted.

The deletion may be continuous, or may comprise a plurality of sections of sequence. The deletion should remove a sufficient amount of nucleotide sequence such that the gene no longer encodes a functional protein. The deletion may, for example, remove at least 50, 60, 70, 80 or 90% of the coding portion of the gene.

The deletion may be total, in which case 100% of the coding portion of the gene is absent, when compared to the corresponding genome of the wild-type isolate.

Interruptions

In the attenuated African Swine Fever (ASF) virus of one embodiment of the present invention one or more of the following genes may be interrupted:

multigene-family 360 genes 9L, 10L, 11L, 12L, 13L and 14L; and multigene-family 505 genes 1R, 2R, 3R and 4R In particular, the following genes may be interrupted:

multigene-family 360 gene 9L; and multigene-family 505 gene 4R

In another embodiment, the present invention provides an attenuated ASF virus wherein the DP148R gene is interrupted.

The gene may be interrupted, for example, by deleting or otherwise modifying the ATG start codon of the gene.

The genome may comprise one or more nucleotide change(s) that ablate expression of the gene. For example, expression of the gene may be ablated by a frame shift or introduction of one or more stop codons in the open reading frame of the gene or a modification of a translational start site.

The interruption may cause the gene to not be transcribed and/or translated.

Functional Genes

As mentioned above, the complete genome sequence of the attenuated ASFV strain OURT88/3 has been determined and compared with that of virulent viruses (Chapman et al., 2008 as above). In addition to the deletions mentioned above, the OURT88/3 strain also has interruptions in 3 other genes: EP402R, EP153R and DP148R (previously referred to as MGF360 18R).

EP402R codes for CD2v protein which is incorporated in the external layer of the virus and may have a role in virus entry or spread. It may also be a target for antibodies that inhibit infection. EP153R is a C-type lectin. DP148R inhibits type I interferon.

The genome of the attenuated virus of the present invention may comprise complete, uninterrupted and functional versions of one or more of the genes EP402R and EP 153R. In the attenuated virus of the present invention, both of these genes may be complete, uninterrupted and functional.

Vaccine/Pharmaceutical Composition

The present invention also provides a vaccine comprising an attenuated ASF virus of the invention.

The term 'vaccine' as used herein refers to a preparation which, when administered to a subject, induces or stimulates a protective immune response. A vaccine can render an organism immune to a particular disease, in the present case ASF. The vaccine of the present invention thus induces an immune response in a subject which is protective against subsequent ASF virus challenge.

The vaccine may comprise a plurality of attenuated ASF viruses of different genotypes. Such a vaccine may be capable of inducing a cross-protective immune response against a plurality of ASF virus genotypes.

The vaccine may be useful in preventing African Swine Fever.

The present invention also provides a pharmaceutical composition which comprises one or more attenuated ASF virus(es) of the invention. The pharmaceutical composition may be used for treating African Swine Fever.

The vaccine or pharmaceutical composition may comprise one or more attenuated ASF virus(es) of the invention and optionally one or more adjuvants, excipients, carriers and diluents.

Immunisation with OURT88/3 induces a high IFNγ response, suggesting that it is mediated by T cells. The attenuated virus of the present invention appears to induce a reduced T cell mediated response (see FIGS. 7 and 13). The attenuated virus of the present invention therefore appears to induce a more "useful" (i.e. more protective) cellular immune response than OURT88/3.

The attenuated virus of the present invention may induce a reduced T-cell mediated response compared to OURT88/3. Methods for analysing and comparing T-cell mediated responses are known in the art, for example by assaying T-cell proliferation in response to antigen (e.g. cell counts, thymidine incorporation or BrdU incorporation), assaying cytokine secretion and/or expression in response to antigen (e.g. ELISA, ELISPOT, flow cytometry) or determination of lymphocyte subpopulations present following inoculation of a subject with the virus (e.g. using flow cytometry).

The attenuated virus of the present invention may induce an immune response comprising a reduced percentage of circulating gamma delta/CD8+ cells and/or a reduced percentage of CD8+/CD4-/γδTCR– (CD8 only cells) and or a reduced percentage of CD8+/CD3– (NK) cells compared to OURT88/3.

Methods of Prevention/Treatment

The present invention also provides a method of preventing and/or treating ASF in a subject by administration of an effective amount of an attenuated virus, vaccine, or pharmaceutical composition of the invention.

The term 'preventing' is intended to refer to averting, delaying, impeding or hindering the contraction of ASF. The vaccine may, for example, prevent or reduce the likelihood of an infectious ASFV entering a cell.

The term "treating" is intended to refer to reducing or alleviating at least one symptom of an existing ASF infection.

The subject may be any animal which is susceptible to ASF infection. ASF susceptible animals include domestic pigs, warthogs, bush pigs and ticks.

The subject vaccinated according to the present invention may be a domestic pig.

Administration

The vaccine of the invention may be administered by any convenient route, such as by intramuscular injection. Other suitable routes of administration include intranasal, oral, subcutaneous, transdermal and vaginal (e.g. during artificial insemination). In one embodiment, oral administration comprises adding the vaccine to animal feed or drinking water. In another embodiment, the vaccine may be added to a bait for a wild animal, for example a bait suitable for wild boar, wild pigs, bushpigs or warthogs.

The present inventors have found the attenuated virus BeninΔMGF of the invention is effective at a lower dose compared to OURT88/3. For example, in Example 3, pigs received $10^2$ HAD of BeninΔMGF which was compared with a dose of $10^4$ TCID$_{50}$ of the virus OURT88/3.

The dose for pig immunisation may therefore be less than 10 HAD$_{50}$ or TCID$_{50}$ per pig. For example the dose may be between $10^2$-$10^3$ HAD$_{50}$ or TCID$_{50}$. The dose may be about $10^2$ HAD$_{50}$ or TCID$_{50}$ per pig.

The vaccine may be administered following a prime-boost regime. For example, after the first inoculation, the subjects may receive a second boosting administration some time (such as about 7, 14, 21 or 28 days) later. Typically the boosting administration is at a higher dose than the priming administration. The boosting dose may be about $10^2$, $10^3$ or $10^4$ $HAD_{50}$ or $TCID_{50}$ of the recombinant attenuated virus per pig.

Method for Preparing Attenuated Virus

The present invention also provides a method of attenuating an African Swine Fever (ASF) virus, which comprises the step of at least partially deleting, or interrupting, the expression of the following genes:

multigene-family 360 genes 9L, 10L, 11L, 12L, 13L and 14L; and
multigene-family 505 genes 1R, 2R, 3R and 4R.

The following genes may be partially or completely deleted:

multigene-family 360 genes 10L, 11L, 12L, 13L and 14L; and
multigene-family 505 genes 1R, 2R and 3R.

The following genes may be interrupted:
multigene-family 360 gene 9L; and
multigene-family 505 gene 4R.

The present invention further provides a method of attenuating an African Swine Fever (ASF) virus, which comprises the step of partially or completely deleting, or interrupting, the expression of the DP148R gene.

The DP148R mutation may also be made in combination with mutations of the multigene-family 360 genes 9L, 10L, 11L, 12L, 13L and 14L and multigene-family 505 genes 1R, 2R, 3R and 4R as described herein.

Methods for deletion of viral genes are known in the art. For example, homologous recombination may be used, in which a transfer vector is created in which the relevant gene(s) are missing and used to transfect virus-infected cells. Recombinant viruses expressing the new portion of sequence may then be selected. Similar procedures may be used in order to interrupt gene expression, for example by deletion of the ATG start codon.

Intranasal Administration

The present inventors have surprisingly found that intranasal administration of an attenuated African Swine Fever (ASF) virus results in improved protection and fewer side effects compared to administration via the intramuscular route, and may require a lower dose to obtain protection. In particular, intranasal administration of attenuated strain OURT88/3 demonstrated complete protection (100%) against challenge with parental ASFV virulent virus, which represents a significant improvement over survival rates using the same attenuated virus via the intramuscular route.

Accordingly, in one embodiment the invention provides an attenuated ASF virus for use in the treatment and/or prevention of African Swine Fever, wherein the attenuated virus is administered intranasally.

The invention further provides a method for treating and/or preventing African Swine Fever in a subject which comprises the step of administering an effective amount of an attenuated ASF virus to the subject by the intranasal route.

The invention also relates to a vaccine comprising an attenuated ASF virus, wherein the vaccine is formulated for intranasal administration.

Further provided is a kit for delivery of an intranasal vaccine formulation comprising:
a) an attenuated ASF virus vaccine; and
b) an intranasal delivery device.

The invention also provides an intranasal delivery device comprising an attenuated ASF virus vaccine. Suitable devices for intranasal administration of vaccine are well known in the art, for example, a syringe or dropper, an aerosol device (e.g. Omron, Philips respironics InnoSpire Deluxe, Devilbiss mask/nebuliser and compressor BreathEazy), a mucosal atomisation device (e.g. LMA MAD Nasal™, Teleflex VaxlNator™), a single or multidose spray pump, a unit dose powder dispenser or a bidose powder dispenser.

The attenuated ASF virus may be any suitable attenuated ASF virus. In one embodiment, the attenuated ASF virus may be one which is not considered suitable for use in the prevention or treatment of African Swine Fever when administered by a different route of administration, such as the intramuscular route, for example due to an unacceptable safety profile or low efficacy. In particular, the attenuated ASF virus may be OURT88/3. The attenuated ASF virus may alternatively be an attenuated ASF virus which lacks a functional version of the multigene-family 360 genes 9L, 10L, 11L, 12L, 13L and 14L and multigene-family 505 genes 1R, 2R, 3R and 4R, and/or lacks a functional version of DP148R. The attenuated ASF virus may be any suitable attenuated ASF virus as described herein, such as BeninΔMGF or BeninΔDP148R.

Intranasal administration according to the invention may be in a droplet, spray or dry powder form, or may be a nebulised or aerosolised vaccine formulation. The dose is typically 2 ml, administered as 1 ml per nostril.

The present inventors have found that intranasal administration of attenuated ASF virus is effective at a lower dose compared to intramuscular administration. For example, in Example 6, pigs immunised intranasally with $10^3$ or $10^4$ of the OURT883 had complete (100%) protection against lethal challenge, compared to much lower survival rates in pigs immunised with the same doses via the intramuscular route.

The dose for intranasal immunisation may therefore be $10^4$ $HAD_{50}$ or $TCID_{50}$ or less per pig. For example the dose may be between $10^2$-$10^3$ $HAD_{50}$ or $TCID_{50}$ The dose may be about $10^2$ $HAD_{50}$ or $TCID_{50}$ per pig.

The vaccine may be administered following a prime-boost regime. For example, after the first inoculation, the subjects may receive a second boosting administration some time (such as about 7, 14, 21 or 28 days) later. Typically the boosting administration is at a higher dose than the priming administration. The boosting dose may be about $10^2$, $10^3$ or $10^4$ $HAD_{50}$ or $TCID_{50}$ of the recombinant attenuated virus per pig.

The invention will now be further described by way of Examples, which are meant to serve to assist one of ordinary skill in the art in carrying out the invention and are not intended in any way to limit the scope of the invention.

EXAMPLES

Example 1—Isolation of Recombinant Virus BeninΔMGF

The MGF 360 genes 10L, 11L, 12L, 13L, 14L and MGF 505 genes 1R, 2R, 3R were deleted from the ASFV Benin 97/1 isolate. In addition the ATG codons of MGF 360 9L and of MGF 505 4R were deleted to interrupt expression of these genes. The genes deleted were replaced with the GUS gene under control of the ASFV p72 promoter.

Figure 1:
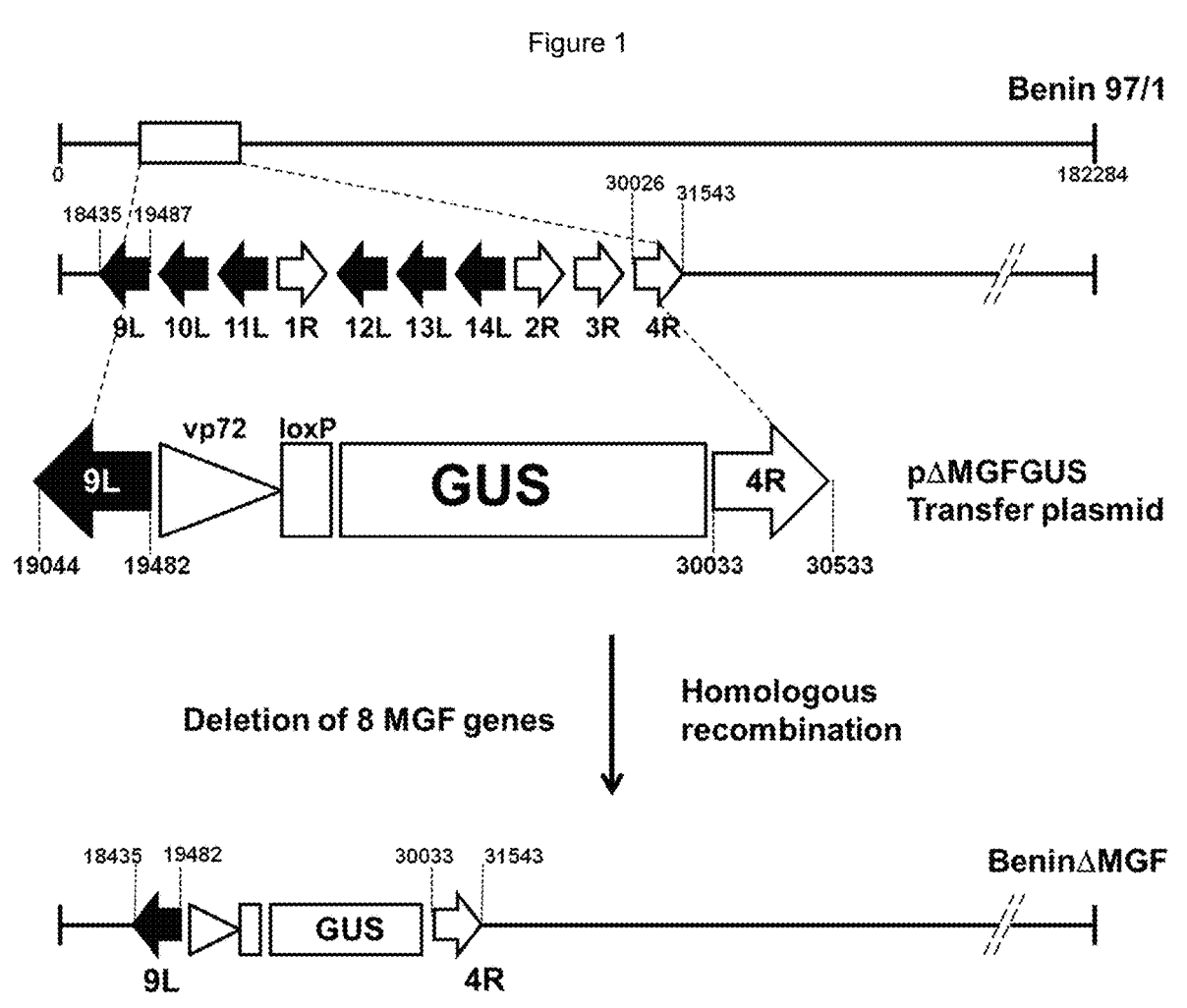

This was achieved by homologous recombination between plasmid pΔMGFGUS and the virus genome (see Materials and Methods and FIG. 1). Recombinant viruses were identified by expression of the GUS gene and purified by infection at limiting dilution. Two independent viruses BeninΔMGFA2 and BeninΔMGFA1 were isolated using this method to reduce the possibility that the phenotype of the gene deletion was associated with mutations which may have occurred elsewhere on the genome.

Recombinant virus BeninΔMGFA2, was further characterised. Genomic DNA was isolated from wild type Benin 97/1 and BeninΔMGFA2 and analysed by PCR to test for the insertion of the GUS marker gene and deletion of the eight MGF genes (FIG. 2). Primers BeninD8F and BeninD8R were designed to anneal within the MGF 360 9L gene, and the MGF360 4R gene, that flank the insertion site. PCR using these primers amplified a 2046 bp fragment using recombinant virus BeninΔMGFA2 gDNA as template (FIG. 2 lane 1).

The size of this band is consistent with that of a PCR product in which the eight MGF genes have been deleted and have been replaced by the GUS marker gene under the control of the ASFV vp72 promoter. To confirm that recombinant virus BeninΔMGFA2 contains the GUS gene, a PCR was carried out using an internal GUS gene primer, RGUS, and primer BeninΔ8F. This PCR amplified a fragment consistent with the expected 1552 bp size (FIG. 2 lane 2) when DNA from BeninΔMGFA2 was used as template. As expected, no PCR fragment was detected using these primers with wild type Benin 97/1 gDNA as template (FIG. 2 lane 3). To confirm that the recombinant virus BeninΔMGFA2 did not contain the MGF 360 10L gene, PCR reactions were carried out using primers BeninΔ8INTF and BeninΔ8INTR located at positions 19613 and 20110 within the MGF 360 10L gene. No PCR fragment was isolated using the recombinant virus BeninΔMGFA2 gDNA as template (FIG. 2 lane 3), but as expected a 498 bp fragment was isolated using wild type Benin 97/1 gDNA as template (FIG. 2 lane 4). Taken together, the PCR data showed that recombinant virus BeninΔMGFA2 contains the GUS gene in place of the eight MGF genes. To additionally confirm that the eight MGF genes had been deleted, gDNA from virus BeninΔMGFA2 was isolated and the junction at the site of deletion/insertion was sequenced using the primers X and Y. Analysis of the sequence revealed that the eight MGF genes had been deleted and the GUS marker gene had been inserted (FIG. 3). The first five bp of the flanking gene MGF 360 9L and the first seven bp of the MGF 505 4R flanking gene had also been deleted. Because the additional deleted sequences each contained the ATG start codon, it can be concluded that the MGF 360 9L and MGF 505 4R genes are not expressed by the recombinant virus BeninΔMGFA2.

Example 2—Growth Characteristics of Recombinant Virus BeninΔMGFA2

To investigate whether deletion of the eight MGF genes affected virus replication, the growth of BeninΔMGFA2 was compared to parental Benin 97/1 virus in primary porcine bone marrow macrophages. Cells were infected at high (10 HAD50/cell) multiplicity of infection (m.o.i.) and total virus was harvested from supernatants at different times post-infection. FIG. 4 shows that there were no significant differences between the titres of wild type Benin 97/1 and those of BeninΔMGFA2 viruses recovered at any of the time points measured. This shows that deletion of the eight MGF genes did not significantly affect the replication of BeninΔMGFA2 in primary porcine bone marrow macrophages.

Example 3—Inoculation of Pigs with Recombinant Virus BeninΔMGF and Attenuated Virus OURT88/3

Figure 5:
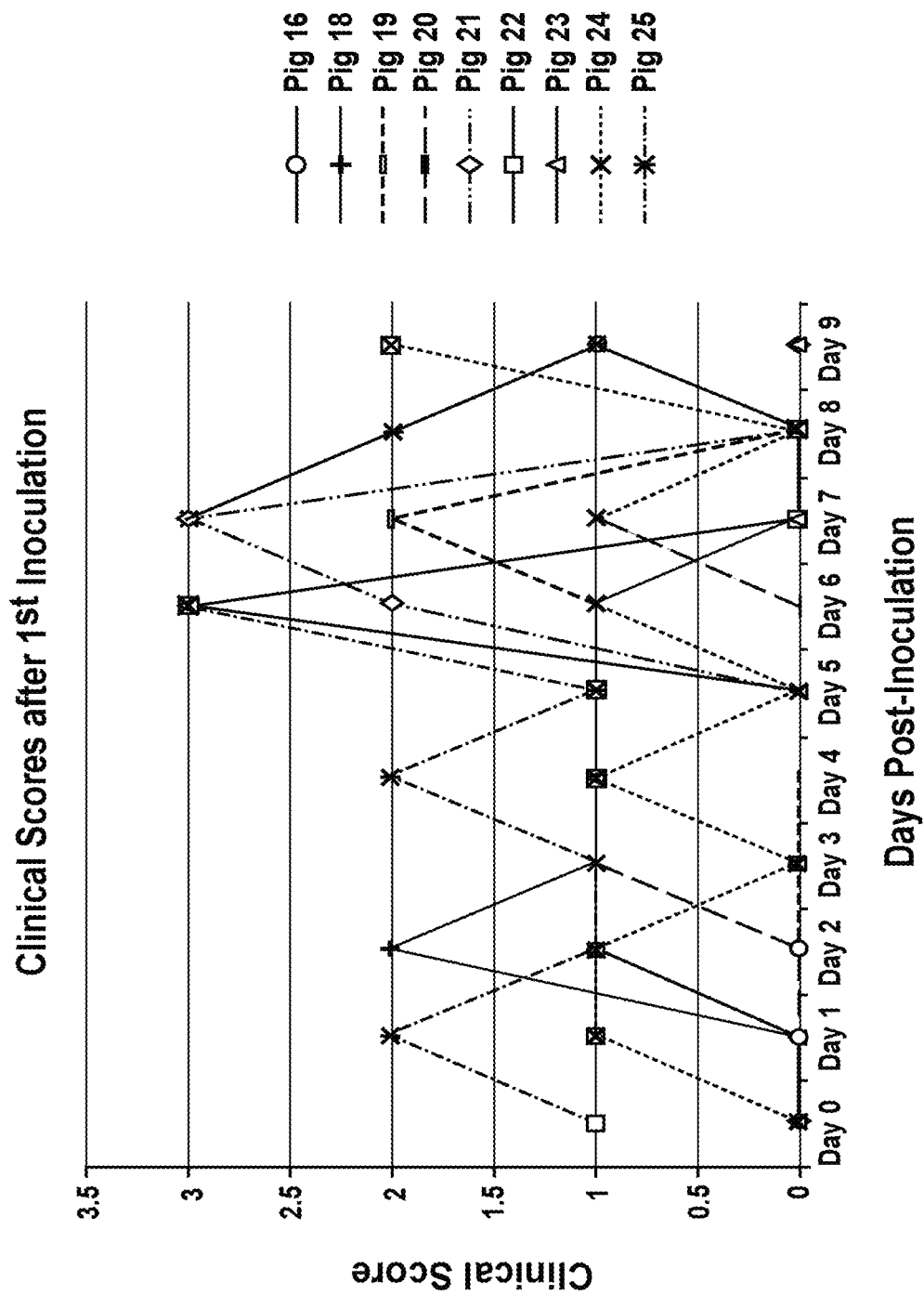
FIG. 5—Clinical scores post first inoculation. Clinical scores (y-axis) of individual pigs at different days (x-axis) post inoculation. Pigs 16, 18, 19 and 20 inoculated with $10^4$ $TCID_{50}$ OURT88/3 virus. Pigs 21, 22, 23 inoculated with $10^2$ $HAD_{50}$ BeninΔMGFA2 virus. Pigs 24 and 25 inoculated with $10^2$ $HAD_{50}$ BeninΔMGFA1 virus. Clinical scoring system as designed by King et al 2011.
Figure 6:
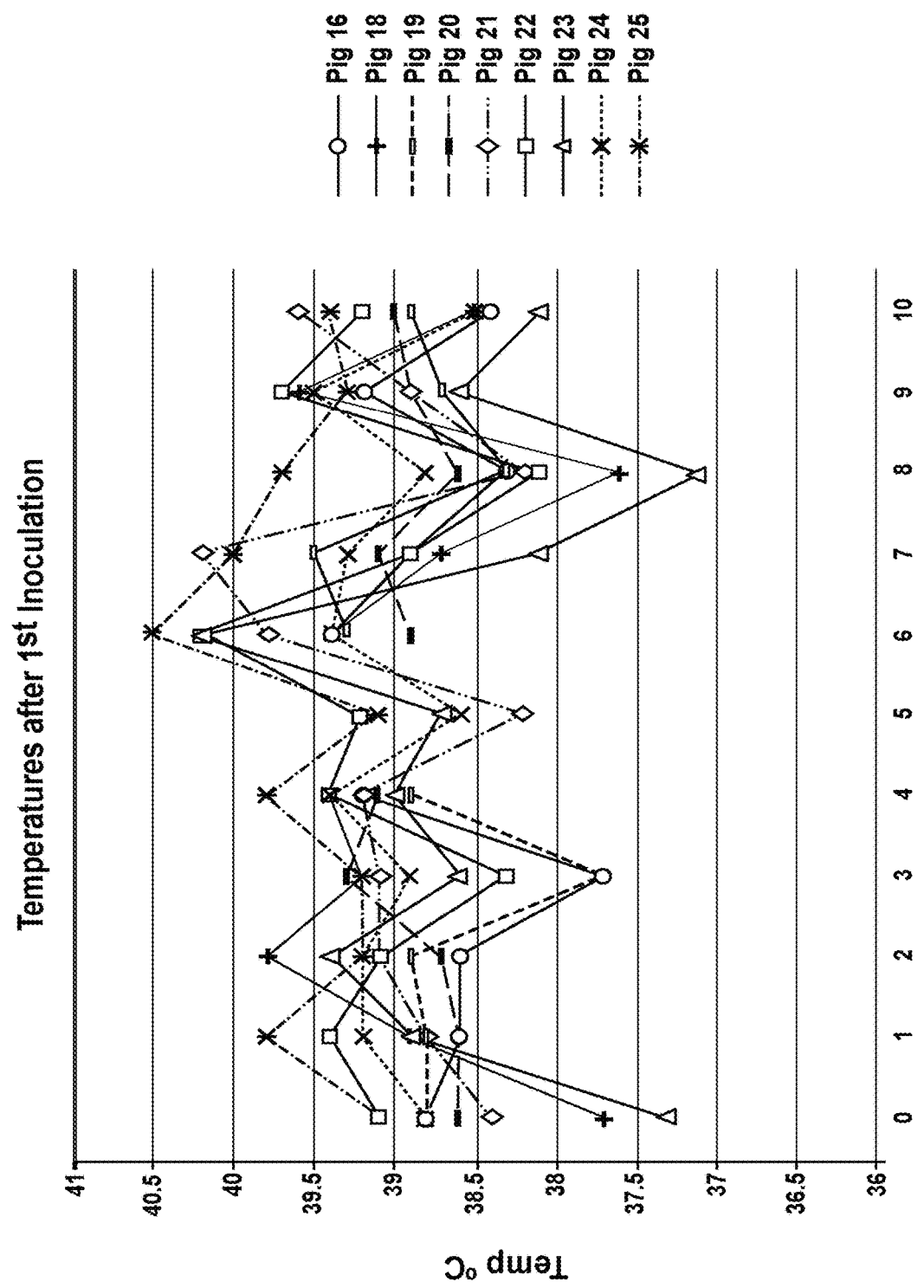
FIG. 6—Temperatures post first inoculation. Temperatures (y-axis) of individual pigs at different days (x-axis) post inoculation. Pigs 16, 18, 19 and 20 inoculated with OURT88/3 virus. Pigs 21, 22, 23 inoculated with BeninΔMGFA2 virus. Pigs 24 and 25 inoculated with BeninΔMGFA1 virus.

One group of three pigs (Group 1) were immunised intramuscularly with $10^2$ HAD of deletion virus BeninΔMGFA2, a second group of two pigs (Group 2) were inoculated with $10^2$ HAD of deletion virus BeninΔMGFA1 and a third group of four pigs (Group 3) were inoculated with $10^4$ TCID$_{50}$ of attenuated virus OURT88/3. Clinical scores and temperatures for each pig were recorded every day and blood samples were taken every seven days. The results of these recordings are shown in FIG. 5 and FIG. 6 and show that none of the pigs had a clinical score above 3 on any day post-inoculation. Four pigs (Group 1 pigs 21 and 22, Group 2 pigs 23 and 25) had a temperature above 40° C. but this was for one or two days only.

Figure 8:
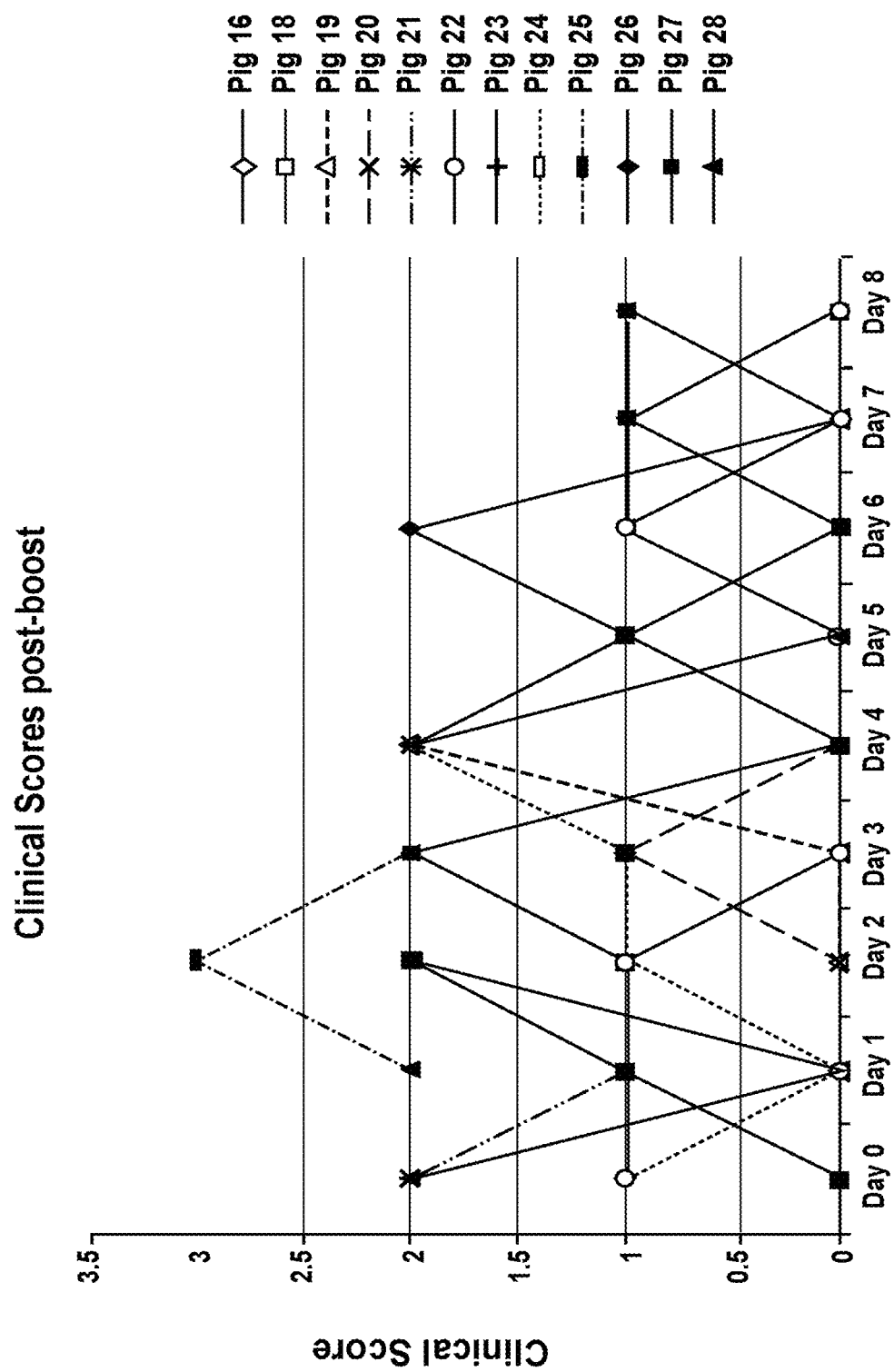
FIG. 8—Clinical scores post boost inoculation. Clinical scores (y-axis) of individual pigs at different days (x-axis) post boost inoculation. Pigs 16, 18, 19 and 20 boost inoculated with $10^4 TCID_{50}$ OURT88/3 virus. Pigs 21, 22, 23 boost inoculated with 10$ $HAD_{50}$ BeninΔMGFA2 virus. Pigs 24 and 25 boost inoculated with $10^4$ $TCID_{50}$ BeninΔMGFA1 virus.
Figure 9:
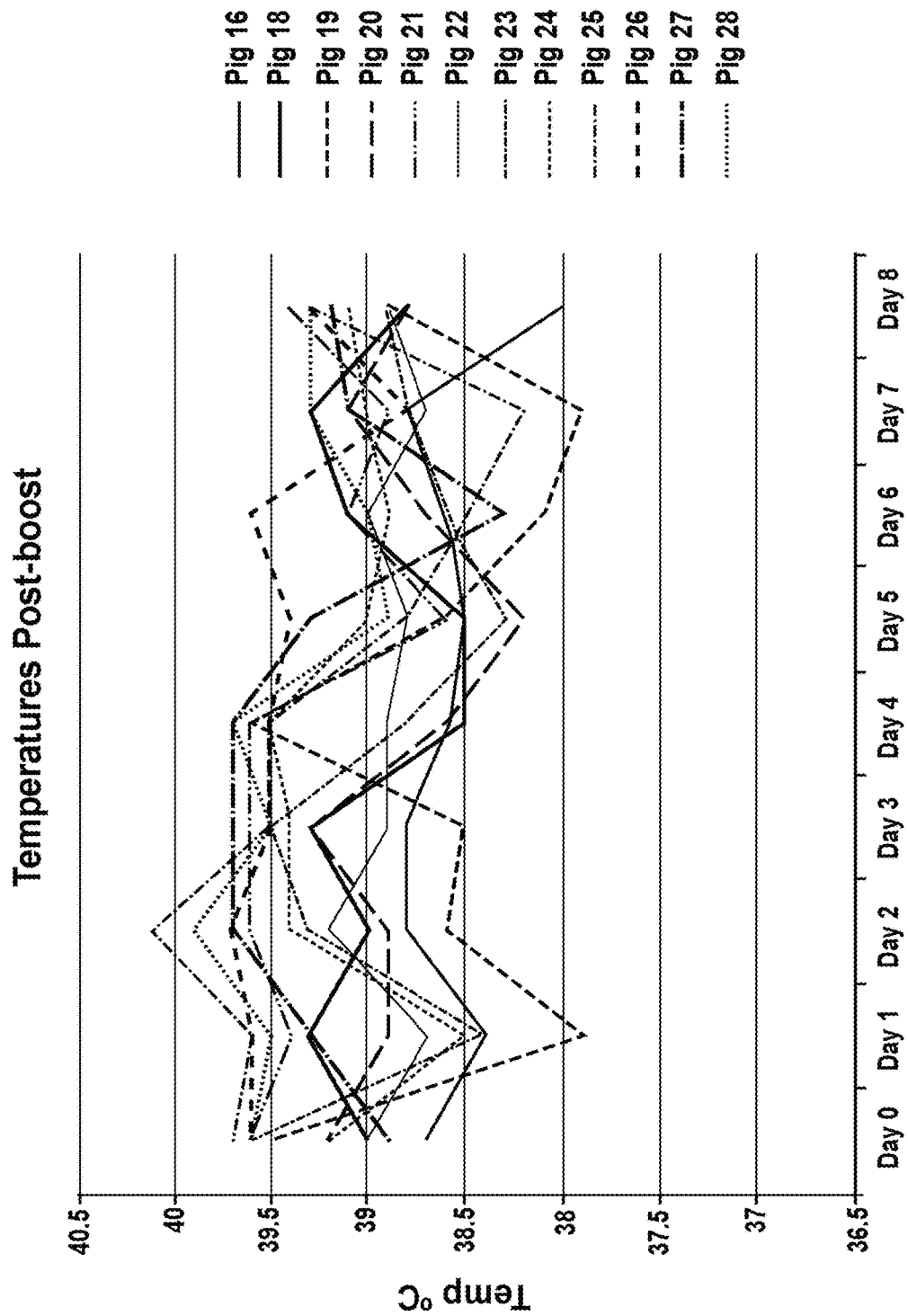
FIG. 9—Temperatures post boost inoculation. Temperatures (y-axis) of individual pigs at different days (x-axis) post inoculation. Pigs 16, 18, 19 and 20 inoculated with $10^4$ $TCID_{50}$ OURT88/3 virus. Pigs 21, 22, 23 inoculated with $10^4$ $HAD_{50}$ BeninΔMGFA2 virus. Pigs 24 and 25 inoculated with $10^4$ $HAD_{50}$ BeninΔMGFA1 virus.

On day 20 post-inoculation, 20 ml of blood was taken from each pig, PBMCs were purified and Group 1 and 2 pig cells were stimulated with BeninΔMGFA2 and BeninΔMGFA1 viruses respectively. PBMCs isolated from Group 3 pigs were stimulated with OURT88/3 virus isolate and the numbers of IFNg producing cells from all three Groups were measured by ELIspot. The results show that three out of four pigs from Group 3 had a high IFNg response to OURT88/3, whereas none of the pigs from Groups 1 and 2 had a high IFNg response to BeninΔMGF or OURT88/3 (FIG. 7). At 21 days after the first inoculation, pigs in Groups 1 and 2 were boosted intramuscularly with $10^4$ HAD of viruses BeninΔMGFA2 and BeninΔMGFA1 respectively and pigs in Group 3 with $10^4$ TCID$_{50}$ of OURT88/3. Clinical observations showed that only one pig (Group 3, pig 19) had a clinical score above score 2 (FIG. 8) and that only one pig (Group 3 pig 19) had a temperature above 40° C. for 1 day (FIG. 9).

Example 4—Challenge of all Pigs with Virulent Benin 97/1

Figure 10:
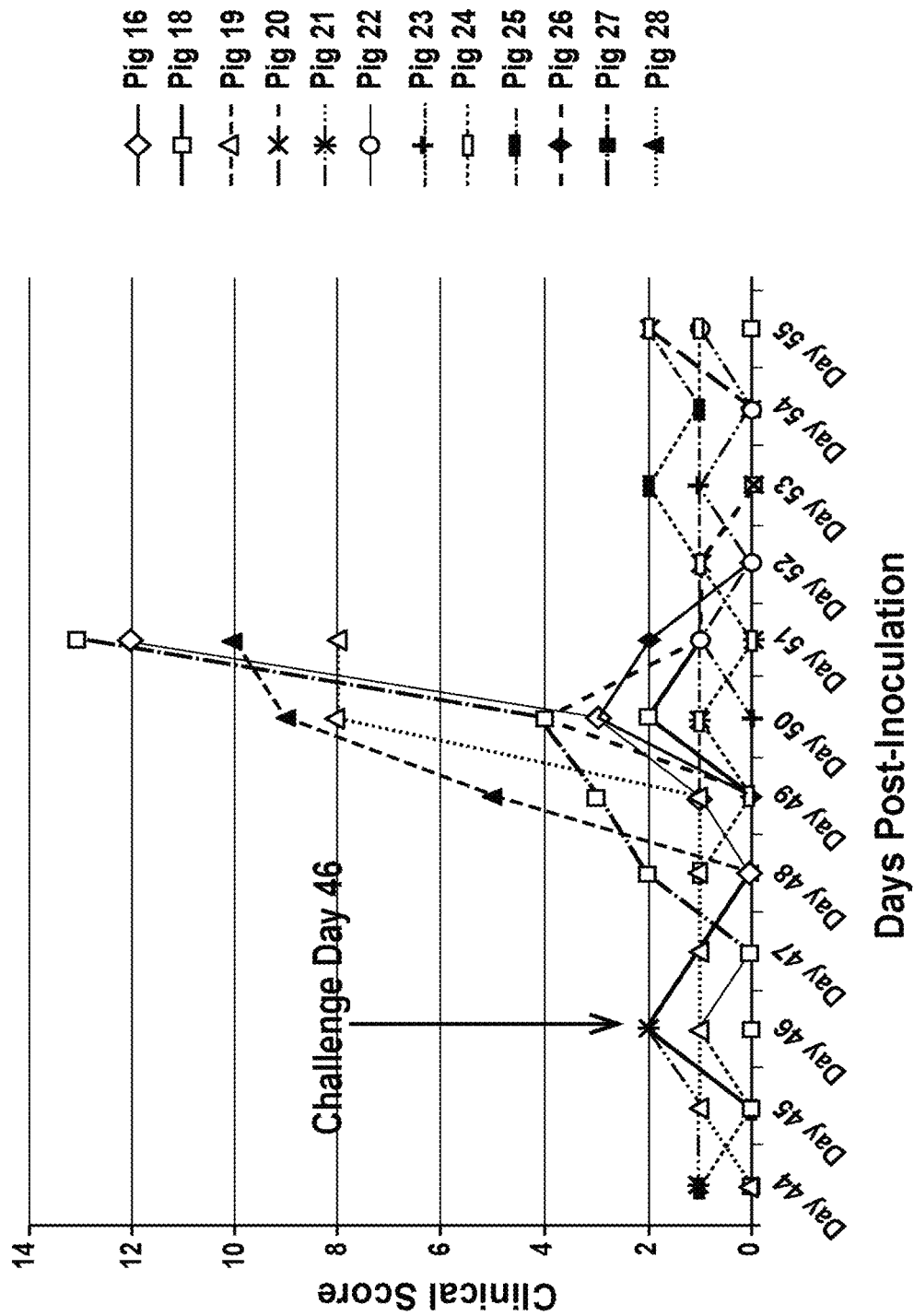
FIG. 10—Clinical scores of pigs after challenge with Benin 97/1. Pigs from Groups 1 (pigs 21, 22, 23), Group 2 (pigs 24, 25), Group 3 (pigs 16, 18, 19, 20) and an unvaccinated Group 4 (pigs 26, 27, 28) were challenged with $10^4$ $HAD_{50}$ Benin 97/1 virus and the clinical scores (y-axis) recorded at different days (x-axis) post challenge.
Figure 11:
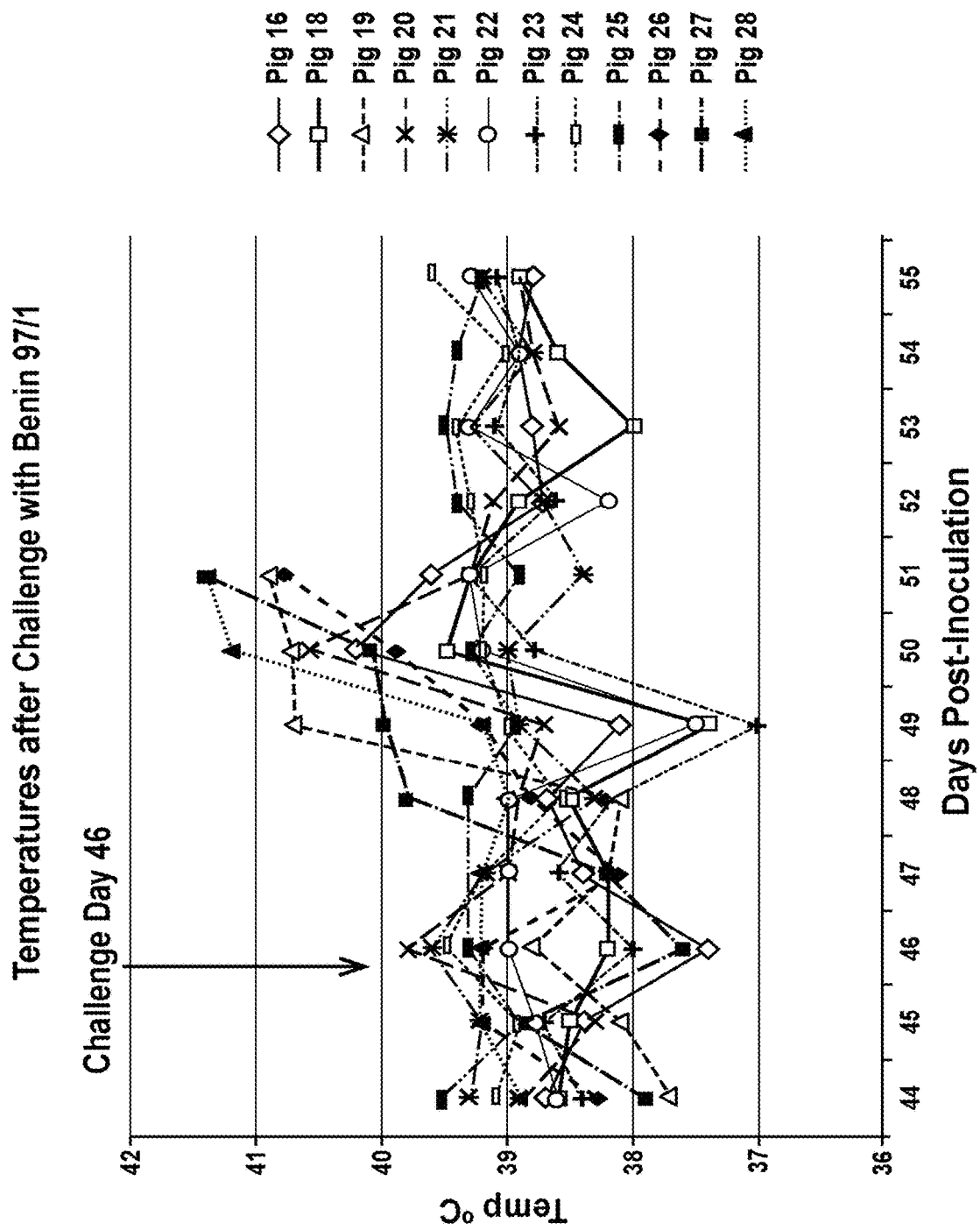
FIG. 11—Temperatures of pigs after challenge with Benin 97/1. Pigs from Groups 1 (pigs 21, 22, 23), Group 2 (pigs 24, 25), Group 3 (pigs 16, 18, 19, 20) and an unvaccinated Group 4 (pigs 26, 27, 28) were challenged with $10^4$ $HAD_{50}$ Benin 97/1 virus and the temperatures (y-axis) recorded at different days (x-axis) post challenge.
Figure 12:
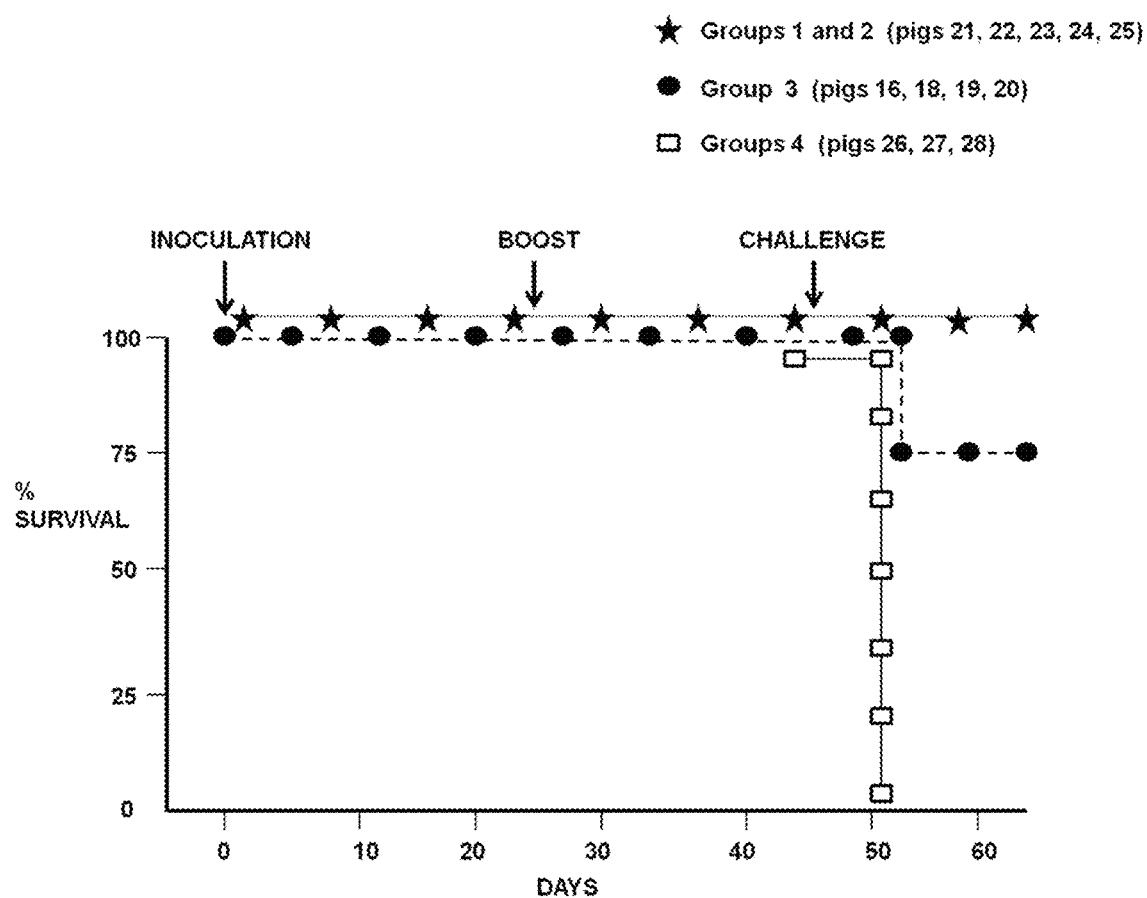
FIG. 12—Results of survival rates for all four groups of pigs. The y-axis shows the percentage of pigs which survived following initial inoculation (Day 0), boost inoculation (Day 25) and challenge (Day 46) with virulent virus Benin 97/1. Groups 1 and 2 ★, Group 3 ●, Group 4 □

On day 46 post initial inoculation (21 days post-boost) all three groups of pigs (Groups 1, 2 and 3) were challenged intramuscularly with $10^4$ HAD of virulent virus Benin 97/1. In addition, a control group of three un-inoculated pigs (Group 4) were also challenged with $10^4$ HAD of virulent virus Benin 97/1. All three pigs from Group 4 and one pig (pig 19) from Group 3 developed high temperatures and high clinical scores (above score 4) and were terminated at five days post-challenge because the humane end-point on the animal license had been reached (FIGS. 10 and 11). All five pigs from Groups 1 and 2 and the remaining three pigs from Group 3 were protected against challenge with virulent virus Benin 97/1 and continued to be healthy up to day 63 when the experiment was terminated (FIG. 12).

Figure 13:
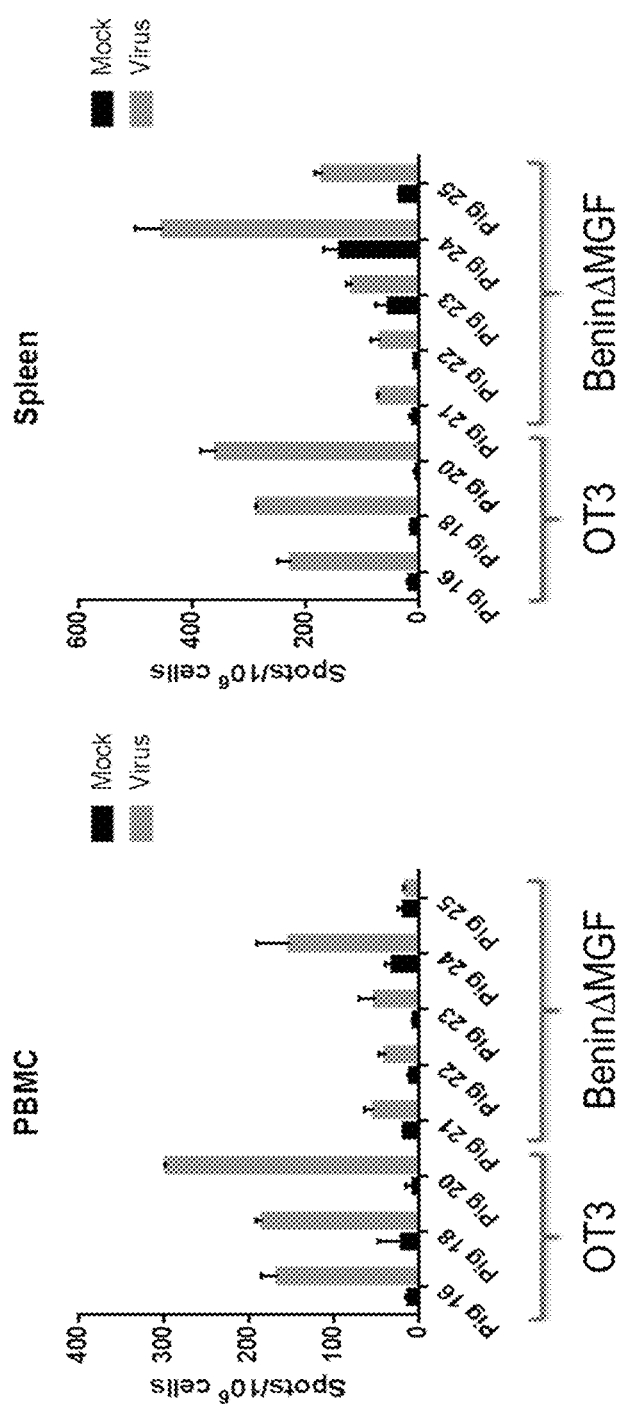
FIG. 13—IFN-γ ELISPOT assays. Peripheral blood mononuclear cells or spleen homogenate cells isolated on day 63 post first inoculation were stimulated ex vivo with either medium alone or Benin 97/1 virus. Results are shown as IFN-γ production per $10^6$ lymphocytes (y-axis) and pig number (x-axis).
Figure 15:
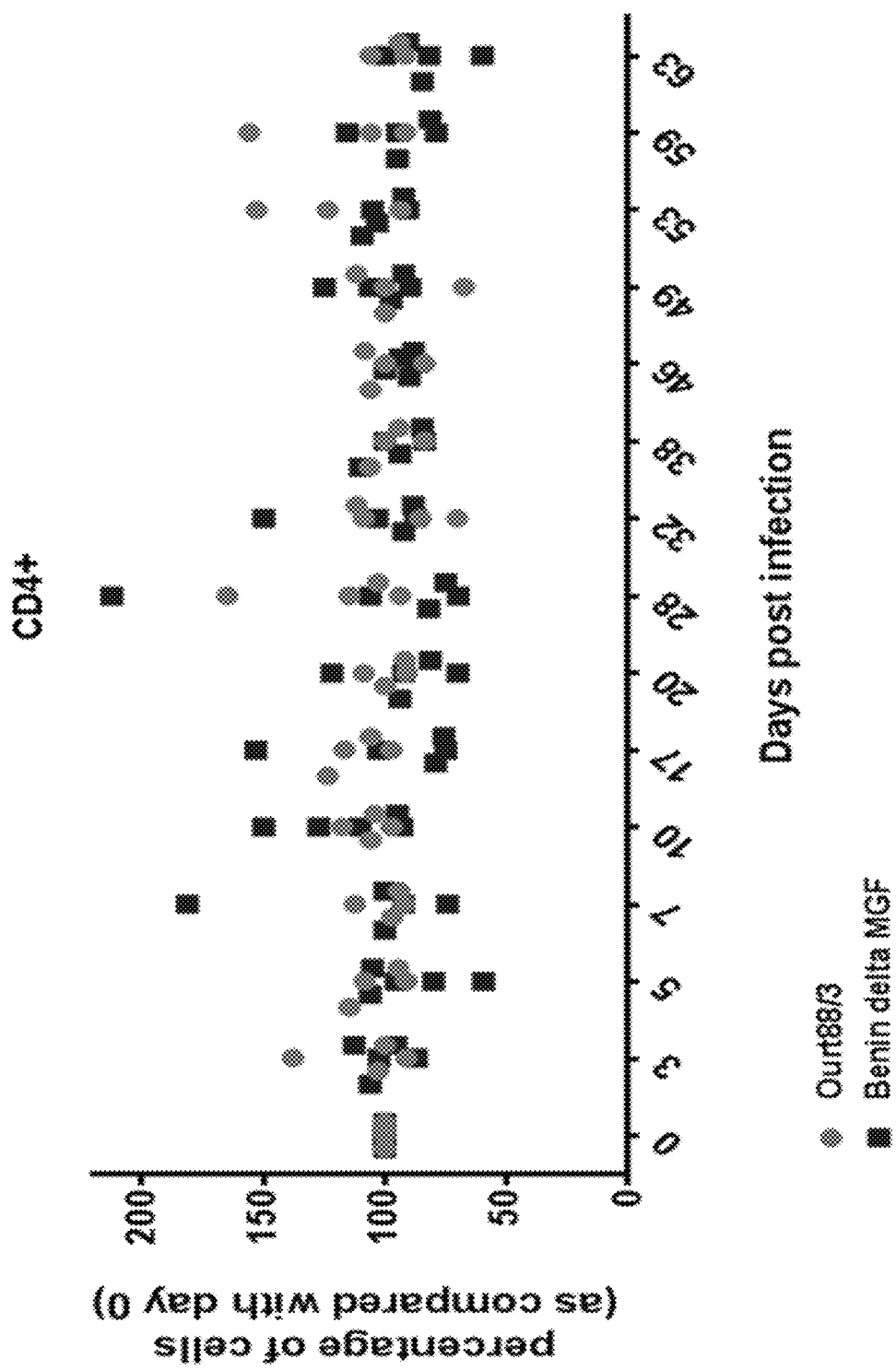
FIG. 15—Percentage of circulating CD4+ cells in peripheral blood samples (as compared with day 0) collected at different days post infection (x-axis) from pigs infected with OURT88/3 (pigs 16 to 20) or BeninΔMGF (pigs 21 to 25).
Figure 16:
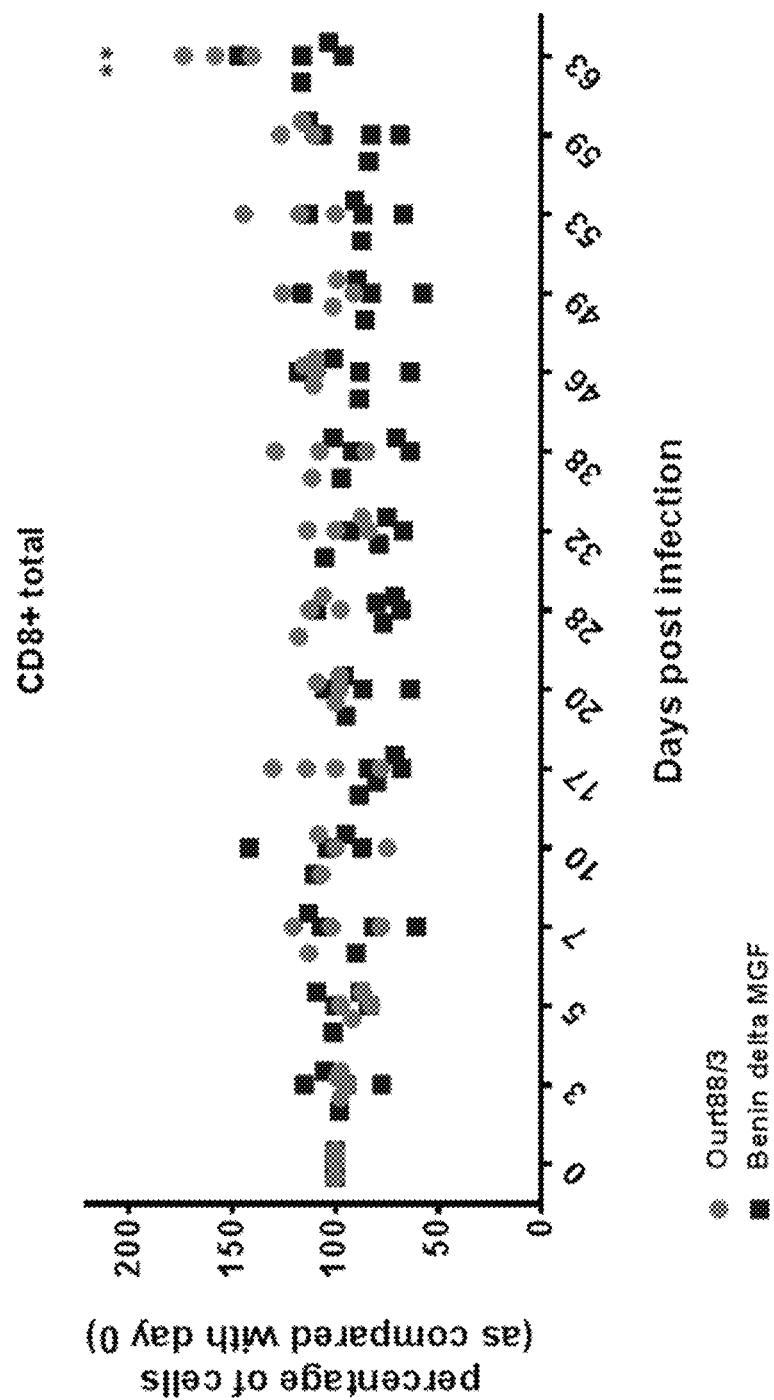
FIG. 16—Percentage of circulating CD8+ total cells in peripheral blood samples (as compared with day 0) collected at different days post infection (x-axis) from pigs infected with OURT88/3 (pigs 16 to 20) or BeninΔMGF (pigs 21 to 25).
Figure 17:
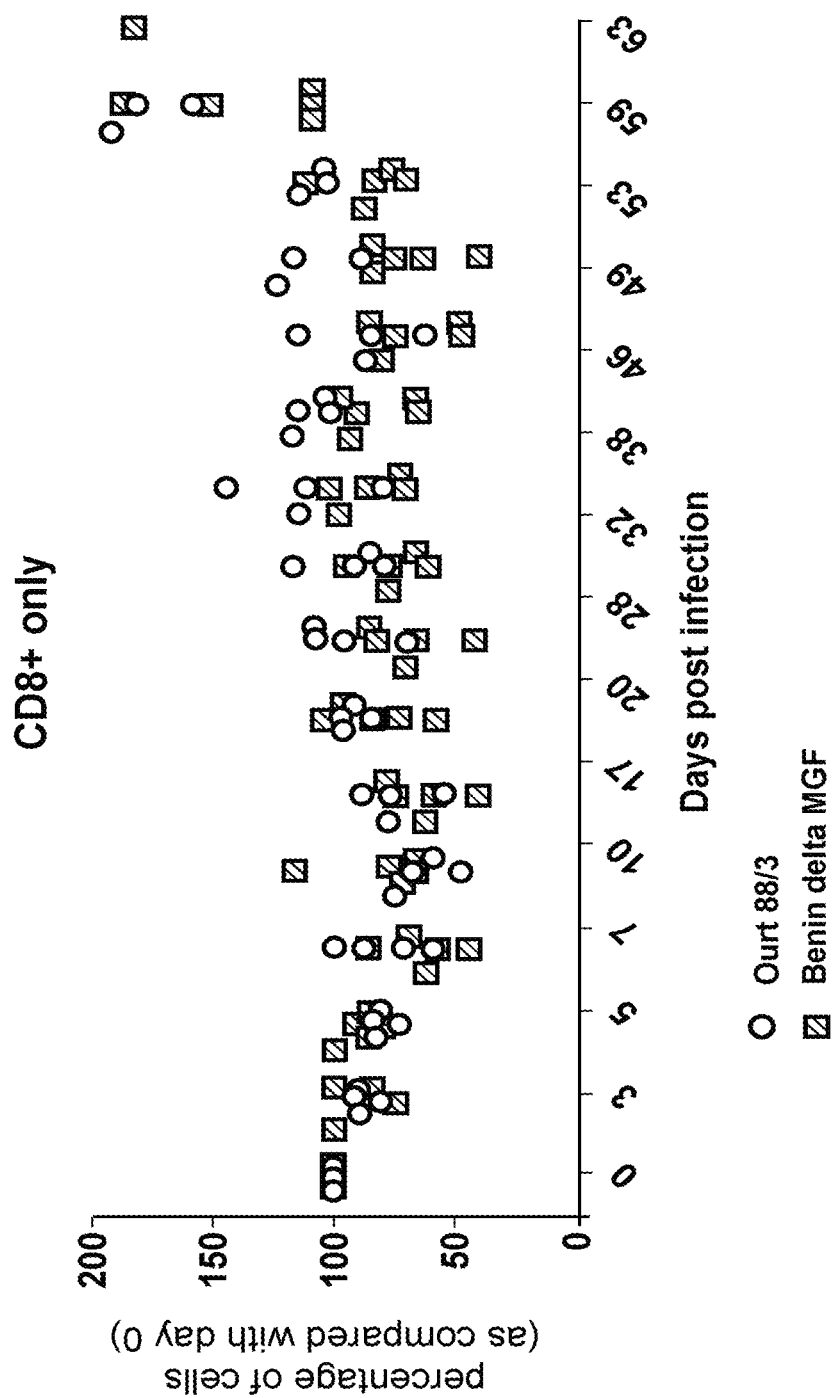
FIG. 17—Percentage of circulating CD8+CD4-γδTCR- (CD8 only) cells in peripheral blood samples (as compared with day 0) collected at different days post infection (x-axis) from pigs infected with OURT88/3 (pigs 16 to 20) or BeninΔMGF (pigs 21 to 25).
Figure 18:
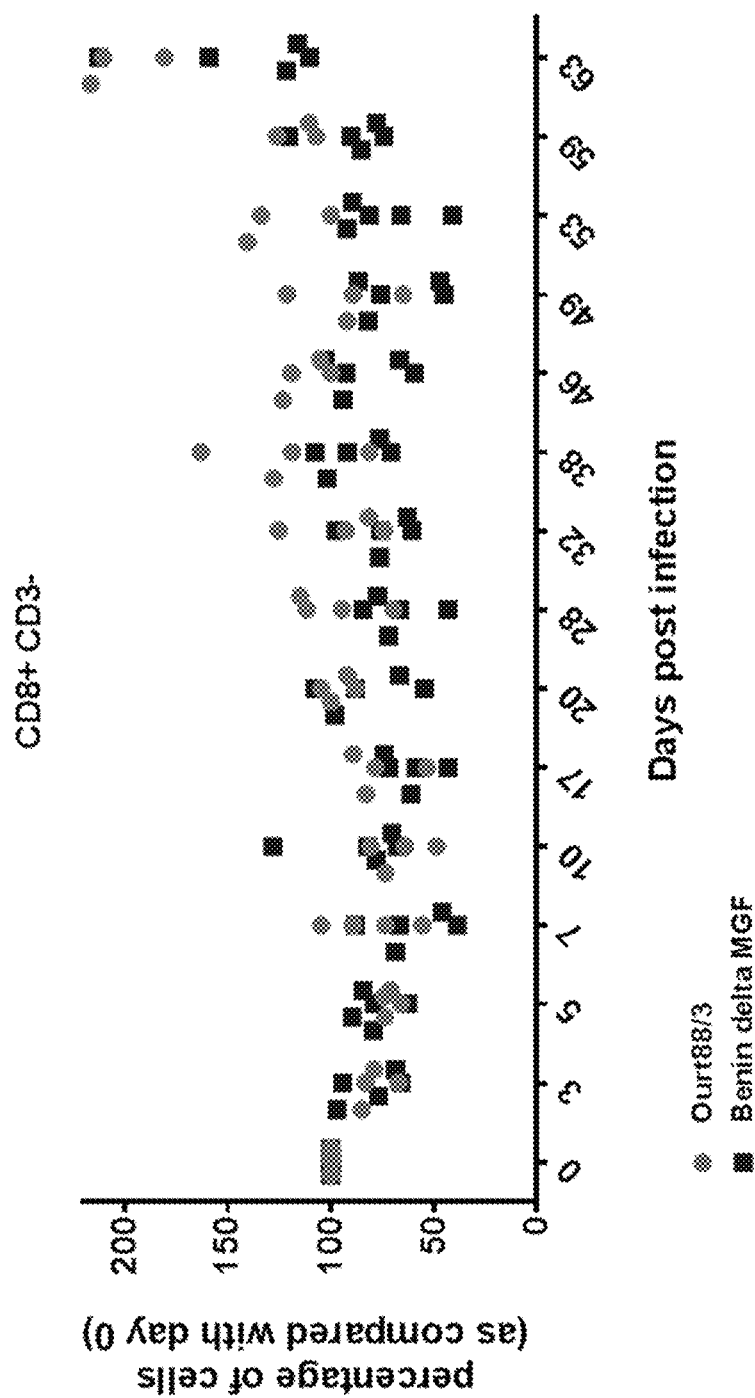
FIG. 18—Percentage of circulating CD8+/CD3- cells in peripheral blood samples (as compared with day 0) collected at different days post infection (x-axis) from pigs infected with OURT88/3 (pigs 16 to 20) or BeninΔMGF (pigs 21 to 25).
Figure 20:
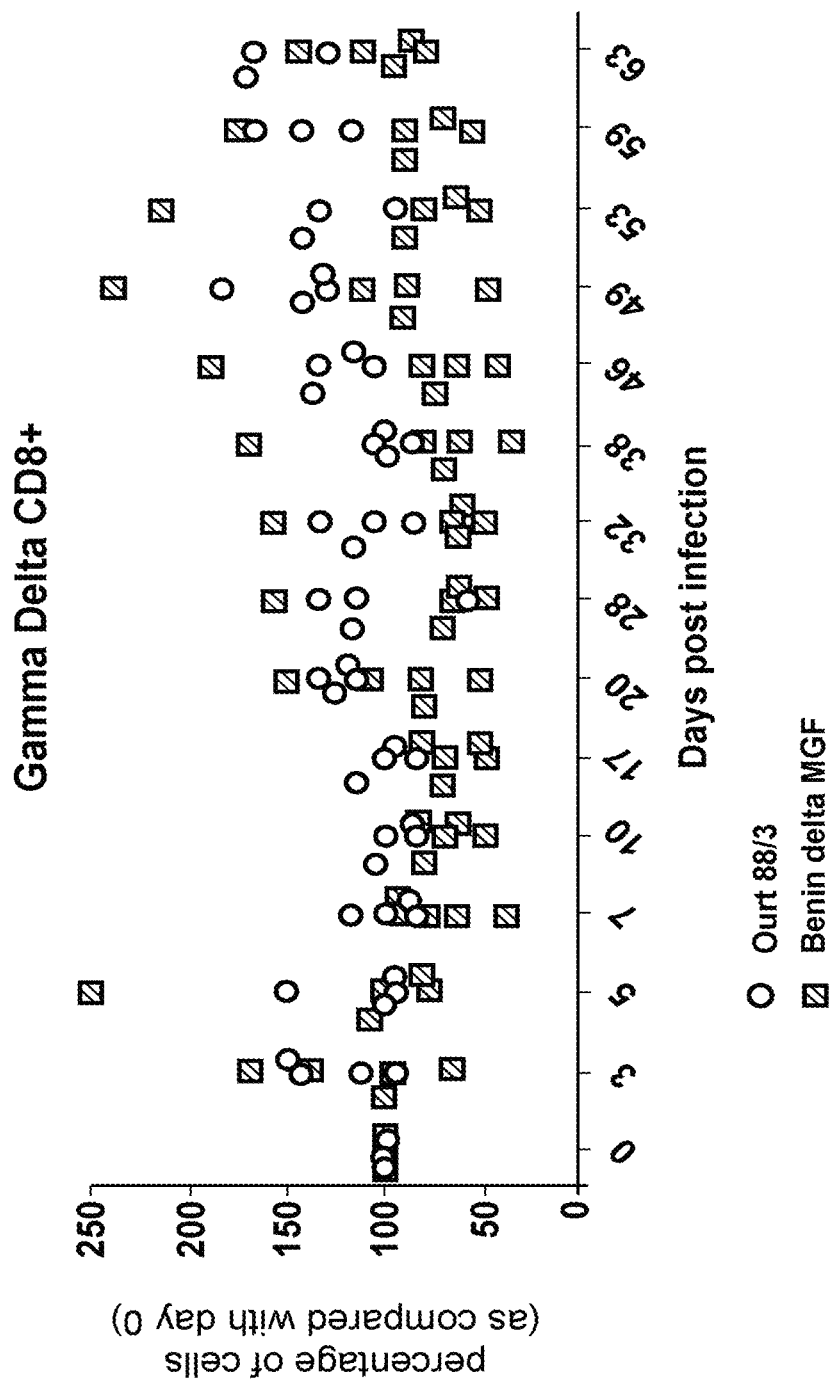
FIG. 20—Percentage of circulating gamma delta/CD8+ cells in peripheral blood samples (as compared with day 0) collected at different days post infection (x-axis) from pigs infected with OURT88/3 (pigs 16 to 20) or BeninΔMGF (pigs 21 to 25).
Figure 21C:
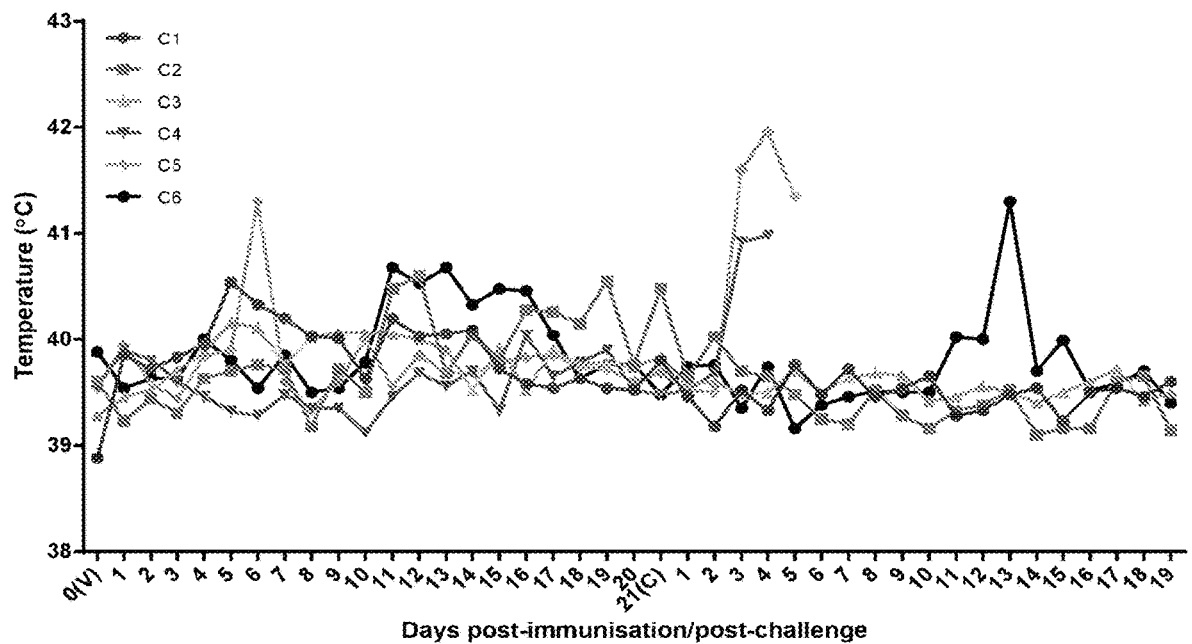
Figure 21D:
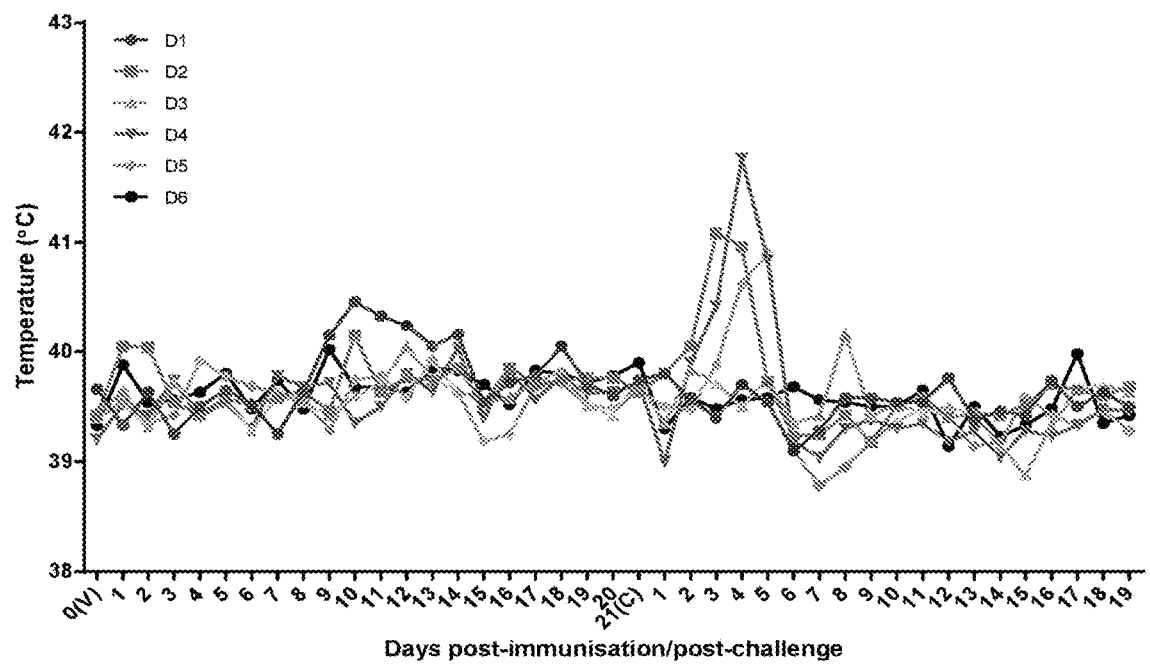
Figure 21E:
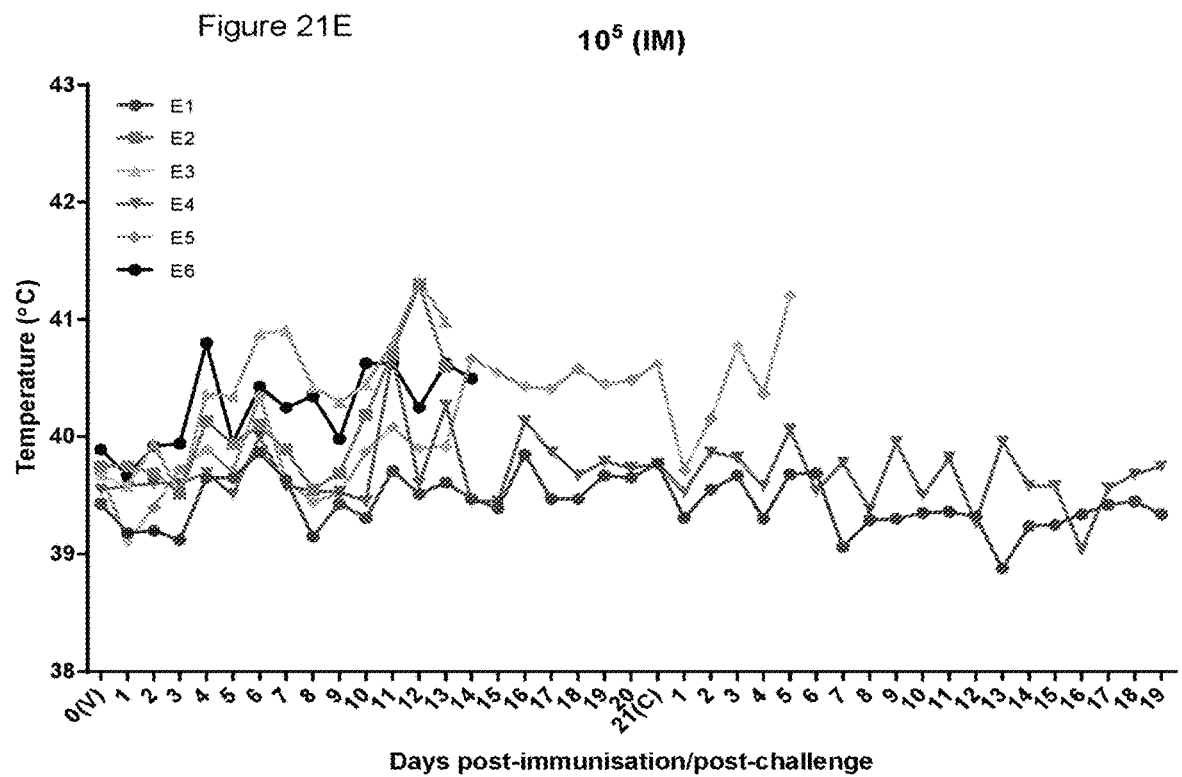
Figure 21F:
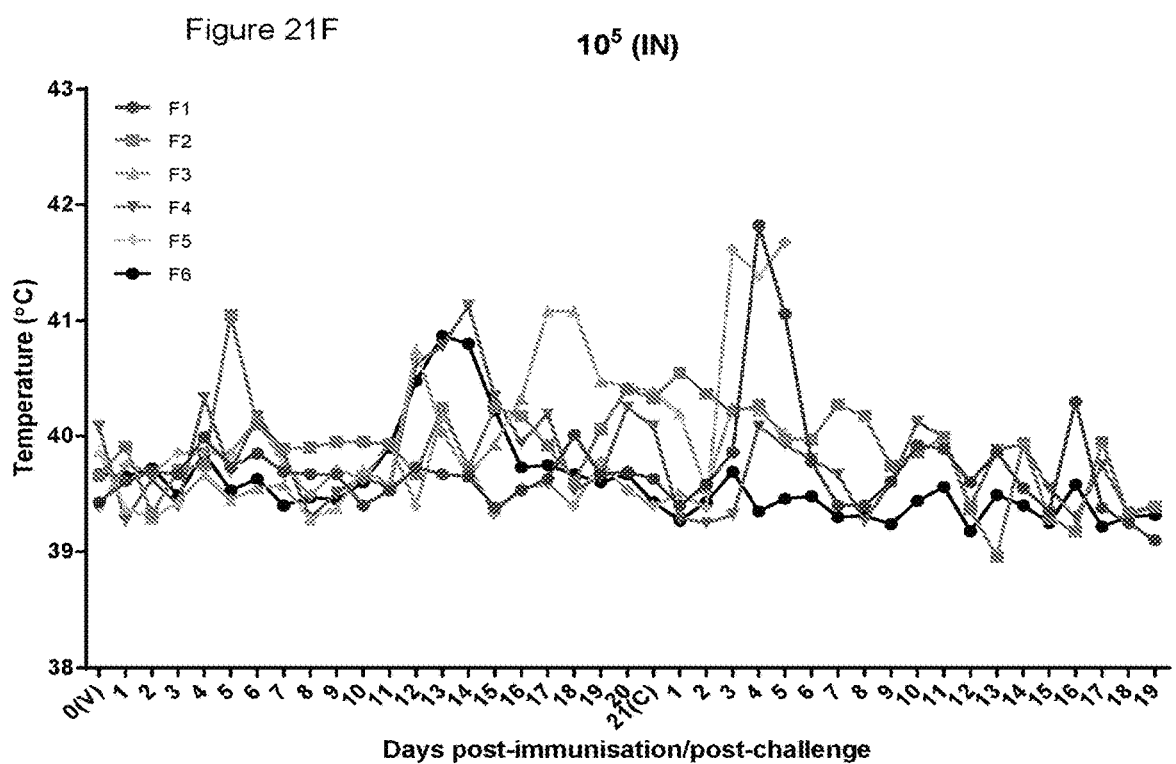
Figure 21G:
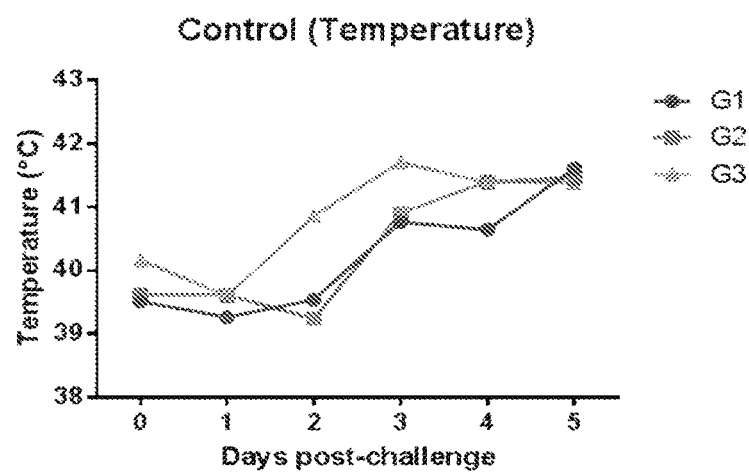
Figure 21H:
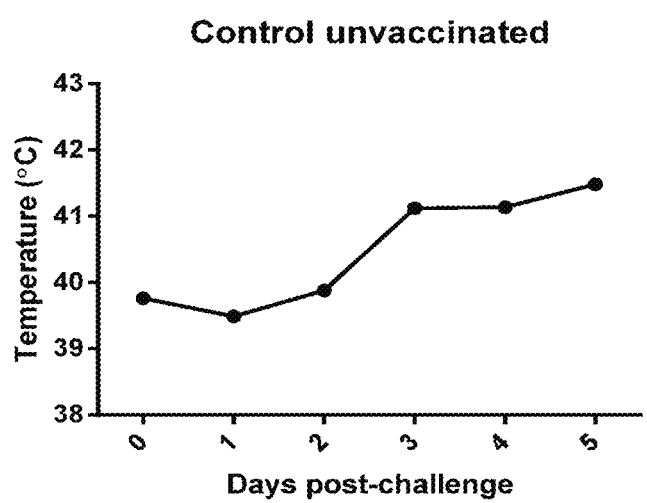

At day 63 post initial inoculation, PBMCs were isolated from blood and cells isolated from spleen and these were stimulated with virus strains and numbers of IFNγ producing cells detected by ELIspot assay. Results showed that all three pigs from Group 3 showed high IFNg responses in cells from both blood and spleen, whereas only one pig (pig 24, Group 2) from Groups 1 and 2 showed high IFNγ responses in blood and spleen (FIG. 13).

Example 5—Characterisation of the Immune Response Generated by BeninΔMGF

Infection with BeninΔMGF was shown to decrease the number of circulating gamma delta CD8+ T cells as early as day 10 post infection. Higher numbers of circulating CD8+ CD4− γδTCR− (CD8 only) and CD8+CD3− (NK cells) cells were observed in pigs infected with OURT88/3 at late days post infection (days 53 and 63). No other significant differences between OURT88/3 and BeninΔMGF infected animals were observed for the other cell populations studied (total CD4+, CD4+CD8+ and total gamma delta T cells) (see FIGS. 14 to 20).

CONCLUSIONS

Inoculation of Pigs with BeninΔMGF Demonstrates the Viruses are Attenuated

Group 1 and 2 pigs were inoculated with $10^2$ HAD of the independently isolated recombinant viruses BeninΔMGFA2 and BeninΔMGFA1. None of the pigs showed a clinical score above score 3 and no pigs showed a temperature above 40.5° C. This showed that deletion viruses BeninΔMGFA2 and BeninΔMGFA1 were attenuated and short transient fever (1 or 2 days) was detected in 4 of the 5 pigs but no other clinical signs associated with ASFV infection.

Pigs in Groups 1 and 2 were boosted intramuscularly with $10^4$ HAD of viruses BeninΔMGFA2 and BeninΔMGFA1. None of the pigs showed a clinical score above score 2 and no pigs showed a temperature above 40.1° C. Similar results were observed following boost of the pigs in Group 3 with the attenuated strain OURT88/3.

Challenge of Pigs Immunised with BeninΔMGF with a Lethal Dose of Benin 97/1 Demonstrates 100% are Protected Pigs from Groups 1, 2 and 3 and three un-inoculated control pigs were challenged with $10^4$ HAD of virulent virus isolate Benin 97/1. All five pigs (100%) from Groups 1 and 2 (BeninΔMGFA2 and BeninΔMGFA1) were protected against virulent virus challenge. 75% of pigs in Group 3 and 0% of pigs in Group 4 were protected against virulent Benin 97/1 (FIG. 12). After challenge with Benin 97/1 no pigs in Groups 1 and 2 showed a temperature above 39.6° C. and no pigs had a clinical score above 2. In contrast all pigs in Group 4 showed temperatures above 40.8° C. and had clinical scores above 8.

The deletion viruses BeninΔMGFA2 and BeninΔMGFA1 showed a better level of protection (100%) compared to the attenuated strain OURT88/3 (75%) against challenge with virulent Benin 97/1.

Materials and Methods
Cells and Viruses

Non-virulent, non-heamabsorbing ASFV isolate OUR T88/3 was obtained from Ourique in Portgual. Virulent, haemabsorbing isolate Benin 97/1 has been previously described. Both OUR T88/3 and Benin 97/1 are p72 genotype I viruses were grown in primary macrophage cultures derived from bone marrow. Titres of virus were determined as the amount of virus causing haemadsorption (for HAD isolates) or cytopathic effects (for non-HAD isolates) in 50% of infected cultures ($HAD_{50}$/ml or $TCID_{50}$/ml).

Construction of Plasmid Transfer Vector pDMGFGUS

The plasmid vector pΔMGFGUS was constructed to facilitate deletion of the eight MGF genes (MGF 360 10L, 11L, 12L, 13L, 14L and MGF 505 1R, 2R, 3R) from the genome of Benin 97/1. Using Benin 97/1 genomic DNA as template a 479 bp fragment (Flank L) located at the 3′ terminus of the MGF 360 9L gene at position 19004-19482 immediately upstream of the MGF 360 10L gene was amplified using the primers FlankLF (ACGTTGCAAAGCTTCCATTAATCCCTCCAGTT-GTTC) (SEQ ID NO: 20) and FlankLR (ACGTTGCAGGTACCCCTCTCTGCAGACTCTCACC) (SEQ ID NO: 21). Using Benin 97/1 genomic DNA as template, a 501 bp fragment (Flank R) located at the 5′ terminus of the MGF 505 4R gene at position 30033-30533 immediately downstream of the MGF 505 3R gene was amplified using the primer FlankRF (ACGTTGCAGCGGCCGCCTCTCCAAGA-CATCTGTCGG) (SEQ ID NO: 22) and primer FlankRR (ACGTACGTCTCGAGCCTCACATGCCATCT-CAAACAATTCC) (SEQ ID NO: 23). The FlankL fragment was digested with HindIII and KpnI and ligated into vector pP72loxPGUS which was also digested with HindIII and KpnI to create plasmid pFlankL-GUS. The FlankR fragment was digested with NotI and XhoI enzymes and ligated into the vector pFlankL-GUS digested with the same enzymes to create the transfer vector pDMGFGUS. The plasmid pDMGFGUS contains a GUS marker gene flanked on the left hand side by the 3′ terminal section of the MGF 360 9L gene, an ASFV vp72 promoter sequence and a loxP sequence. To the right side of the GUS gene is located the 5′ terminal sequence of the MGF 505 4R gene. (FIG. 1).

Construction and Isolation of Recombinant Virus BeninΔMGF

Primary porcine alveolar macrophages (35 mm dish, $10^6$ cells) were infected with Benin 97/3 at a multiplicity of infection (m.o.i). of 10 and incubated at 37° C. for 5 hours, and then washed with Earle's saline (10% porcine serum, penicillin/streptomycin 10,000 u mg-1 ml-1). A transfection mixture containing 250 μl OPTIM-MEM™ (Gibco-Life Technologies), 5 μg pΔMGFGUS and 7.5 μl TRANS-IT LT-1 (Mirus) transfection reagent was incubated at 20° C. for 20 minutes before adding it to the infected cells. Incubation was continued at 37° C. for 4 hours before the addition of 1 ml Earle's saline and continued incubation at 37° C. Virus was harvested from the infected and transfected cells 72 hours post-infection and cell debris removed by centrifugation. Aliquots of virus containing supernatant were used to infect bone marrow macrophages on 96 well plates. At 90 hours post-infection Earle's saline containing 100 μg/ml 5-Bromo-4-chloro-1H-indol-3-yl β-D-glucopyranosiduronic acid (X-Gluc) was added and wells appearing 'blue' containing recombinant GUS expressing viruses were harvested. Infections at limiting dilution were further carried out on pig bone marrow macrophages containing X-Gluc until only one blue well per 96 well plate was observed to indicate infection with the recombinant deletion virus. No evidence of virus infection (cytopathic effect (cpe)) was observed in the other 95 wells. Two independent recombinant viruses (BeninΔMGFA2 and BeninΔMGFA1) were isolated using this method. High titre stocks of recombinant viruses BeninΔMGFA2 and BeninΔMGFA1 were grown up on porcine bone marrow macrophages.

Growth Characteristics of Recombinant Virus BeninΔMGFA2

The growth of BeninΔMGFA2 was compared to parental Benin 97/1 virus in primary porcine bone marrow macrophages. Cells were infected at high (10 $HAD_{50}$/cell) multiplicity of infection (m.o.i.) and total virus was harvested from supernatants at different times post-infection.

Purification of Viral Genomic DNA and PCR

Viral genomic DNA from BeninΔMGF and Benin 97/1 virus harvests were purified from 300 ul of supernatant from infected pig bone marrow macrophage infected cells using a GE Healthcare Illustra Genomic Prep Mini Spin kit. Analysis of viral genomic DNA was carried out by PCR using the specific DNA primers BeninD8F (GGT-GAGAGTCTGCAGAGAGAGG) (SEQ ID NO: 24), BeninD8R (GCCCTAGCACTTGTAACG) (SEQ ID NO: 25), RGUS (CCTTCTCTGCCGTTTCCAAATCGCCGC) (SEQ ID NO: 26), BeninD8INTF (CGATGTATCATT-GATGTC) (SEQ ID NO: 27), Benin D8INTR (GGA-TAATCTTAGGGAGGCC) (SEQ ID NO: 28).

Sequencing of Recombinant Virus BeninΔMGFA2

Viral gDNA was isolated from the harvest of BeninDMGF infected cells and sequenced using the following primers 9LF (ATGACGCATTAAACCGGCG) (SEQ ID NO: 29) and 4RR (CAGTATAGCCCTAGCACTTG) (SEQ ID NO: 30).

ELIspot

IFN-g ELIspot was carried out as previously described (Gerner et al 2006 Virus Res>121:223-228).

Pig Inoculation and Challenge Pigs used were cross-bred, large white×Landrace, of average weight 15 kg at the first inoculation. All pigs were maintained in high security SAPO4 facilities throughout and the experiment performed under Home Office license PPL 70/7198-. One group of three pigs (Group 1, pigs 21, 22 and 23) were inoculated intramuscularly with $10^2 HAD_{50}$ of recombinant virus BeninDMGFA2. A second group of two pigs (Group 2, pigs 24 and 25) were inoculated intramuscularly with $10^2 HAD_{50}$ of recombinant virus BeninΔMGFA1. A third group of four pigs (Group 3, pigs 16, 18, 19 and 20) were inoculated with $10^4$ $TCID_{50}$ of attenuated strain OURT88/3. The inventors had previously determined that a dose of $10^4$ $TCID_{50}$ of OURT88/3 was needed to induce protection and that $10^3$ was less effective.

Three weeks later to boost the ASFV specific adaptive immune responses, pigs in Groups 1 and 2 were inoculated with $10^4 HAD_{50}$ of recombinant viruses BeninDMGFA2 and BeninDMGFA1 respectively and Group 3 pigs were immunised with $10^4 TCID_{50}$ of OURT88/3. Three weeks post-boost Groups 1, 2, 3 and a fourth group of three pigs (Group 4, pigs 26, 27 and 28) containing three non-immunised pigs, were challenged intramuscularly with $10^4$ $HAD_{50}$ of virulent ASFV isolate Benin 97/1. ASFV-inoculated and challenged pigs were monitored daily for body temperature and clinical signs and these were scored as reported by King et al., 2011. All pigs were examined by post-mortem at termination and spleen and lymph tissues were collected.

Characterisation of T Cell Subpopulations

Blood samples were collected from the infected pigs at different times post infection and the different T cell populations were identified by using the following Zenon (Invitrogen) labelled antibodies: mouse IgG1 anti-porcine CD3 (Alexa Fluor 405), mouse IgG2b anti-porcine CD4 (Alexa Fluor 647), mouse IgG2a anti-porcine CD8αα (R-PE) and mouse IgG2b anti-porcine gamma delta TCR (Alexa Fluor 488). Briefly, 100 μl of whole blood was incubated with 5 μl of each conjugated antibody for 20 minutes at room temperature. Red blood cells were lysed by adding 4 ml of 1×BD FACS lysing solution (BD Biosciences) and vortexing. Cells were pelleted by centrifugation at 1200 rpm for 7 minutes and the supernatant was discarded. The cells were then fixed with 4% paraformaldehyde for 30 minutes, washed twice with PBS and finally analysed by flow cytometry (MACSQuant, Miltenyi Biotec). Lymphocyte subsets were gated based on cell surface markers staining using FCS express software.

Example 6—Immunisation with OUR T88/3 Via Different Routes

The experiments were carried out in level-3 biocontainment facilities (BSL-3) of Centre de Recerca en Sanitat Animal (CReSA, Barcelona, Spain). All animal experiments were carried out under UK Home Office License number 70/7198 with the approval of the Ethics Committees for Animal Experiments of the Autonomy University of Barcelona (No. 1189R5) and the Regional Government of Catalonia, Spain (No. 5796), and complied fully with the regulated procedures from the Animals (Scientific Procedures) Act 1986.

Materials and Methods 7-week-old Large White and Pietrain crossbred male piglets in good health, vaccinated against Porcine Circovirus type 2 and Mycoplasma hyopneumoniae, average weight 15 kg, from a high health herd tested negative for Porcine Respiratory and Reproductive syndrome (PRRS) and Aujeszky's disease were used. After a 5-day acclimatisation period, three groups of six pigs each were immunised intramuscularly (IM) with 1 ml containing $10^3$ (group A), $10^4$ (group C) and $10^5$ (group E) $TCID_{50}$/ml of low virulent ASFV isolate OUR T88/3 respectively. An additional three groups of six pigs each were immunised intranasally (IN), using a mucosal atomization device, with 1 ml per nostril containing $10^3$ (group B), $10^4$ (group D) and $10^5$ (group F) $TCID_{50}$/ml of low virulent isolate OUR T88/3. Three weeks later all immunised groups, together with a control group (group G) containing three non-immunised pigs, were challenged intramuscularly with 1 ml containing $10^4$ $TCID_{50}$/ml of the closely related virulent ASFV isolate OUR T88/1. This control group was housed separately (room 4), while pigs immunised with the same ASFV titre, but by different inoculation routes (IN or IM), were allocated in the same isolation room separated by 1 m high partition as follows: experiment 1 (groups A and B), experiment 2 (groups C and D), experiment 3 (groups E and F).

Sampling, Clinical and Post-Mortem Examination

Immunisation day was defined as day 0 (0 dpi). Rectal temperatures and clinical signs were monitored daily prior to immunisation and throughout the study, following a clinical score previously reported (King et al., 2011). EDTA blood and serum samples were collected from all pigs prior to virus immunisation (0 dpi), after immunisation (at 3, 5, 7, 14 and 21 dpi) and after challenge (at 3, 5, 7, 14 and 19 dpc).

A post-mortem examination also was carried out in order to evaluate gross lesions of dead pigs or pigs euthanized during the experiment upon reaching a predetermined humane endpoint, as well as at the end of the experiment at 19 days post-challenge (dpc). Macroscopic lesions were evaluated in accordance with the standardized pathological framework of ASFV infections (Galindo-Cardiel et al., 2013). The humane end point was determined in accordance with the welfare regulations specified in the UK Home Office License, so that pigs with a rectal temperature over 40.5° C. for three consecutive days, or showing three or more clinical signs of disease combined on a single day, were euthanized. Euthanasia was conducted by intravenous injection of pentobarbital sodium.

ASFV Detection and Immune Response Evaluation.

After collection, EDTA blood samples were frozen at −80° C. until ASFV detection by quantitative PCR (qPCR) as described previously (King et al., 2003). Frozen tissues samples (spleen, tonsil, lung, submandibular, retropharyngeal and gastrohepatic lymph nodes) were also analysed for the presence of ASFV by qPCR. Serum samples were also frozen at −80° C. until assayed by commercially available ELISA kits for detection of antibodies against Vp72 structural protein of ASFV (INGEZIM PPA Compac, Ingenasa Madrid, Spain). In addition, serum samples were used to evaluate, by commercially available ELISA kits (R&D Systems, Abingdon, UK), porcine cytokines with inflammatory and immunological functions during humoral and cell mediated immunity in pigs (IL-1β, TNFα, IFNγ, IL-4 and IL-10). Cytokine concentrations were presented as pg/ml.

Statistical Analyses

Data were analysed using the statistical analysis program GraphPad Prism Version 6.0 (GraphPad Software). The values of rectal temperature, clinical signs, macroscopic lesions, viraemia, ASFV antibodies and cytokine levels were assessed to calculate means±standard deviations (SD). For analysis of temperature and clinical signs, differences between baseline values (day 0) and the values obtained at each time-point in the un-inoculated control group and inoculated groups were analysed using One-way ANOVA with Bonferroni post-test. Furthermore, differences between the un-inoculated control group and infected groups as well as differences between both infected groups at the same time-point were analysed using a two-way ANOVA with Bonferroni post-test. For all comparisons, differences were considered significant at P<0.05.

Results from Control Non-Immune Pigs

From 3 dpc, pigs in control Group G (non-immune) displayed non-specific symptoms such as fever (40.8-41.7° C.) and apathy (see FIG. 21 G). These clinical signs increased progressively until 5 dpc, with rectal temperatures between 41.4-41.6° C., recumbence and the presence of skin erythema and cyanotic areas on tip of ears, being euthanized for ethical reasons. After euthanasia of pigs at 5 dpc, necropsies revealed the presence of gross lesions characteristic of acute forms of ASF such as hemorrhagic lymphadenitis (gastrohepatic and renal lymph nodes being the most severely affected), hyperemic splenomegaly, non-collapsed lungs with interstitial and alveolar edema as well as foam in trachea, petechiae in kidneys (cortex and medulla) and lungs, retroperitoneal edema and moderate hepatic congestion.

Results from Groups Immunised by Intranasal Route

Of those pigs immunised with OURT88/3 by the intranasal route 100% (n=6) of those in groups B ($10^3$ $TCID_{50}$) and D ($10^4$ $TCID_{50}$) survived challenge. Some of the pigs that survived displayed a transient moderate joint swelling before and after challenge. Two pigs from group B (B3 and B4) and 3 from group D (D2, D4 and D5) showed other short transient clinical signs post-challenge (temperature, inappetence, apathy). In group F ($10^5$ $TCID_{50}$) 66% survived challenge. The two pigs which did not survive (F3 and F5) were euthanized at day 5 post-challenge showing gross lesions characteristic of ASF and other some other clinical signs (elbow swelling and erosion of skin on the nose). Three surviving pigs (F1, F2 and F4) also showed clinical signs and lesions including severe joint swelling, laboured breathing, erythema on ears, conjunctivitis as well as skin erosions/ulcers in nose, flanks and limbs that lasted until the end of the experiment.

Results from Groups Immunised by the Intramuscular Route

Of the pigs immunised by the intramuscular route, 3 (E2, E3 and E6) from group E ($10^5$ $TCID_{50}$) were euthanized or found dead between 13 and 14 dpi and before challenge showing signs typical of ASF. Of those pigs challenged 50% (3/6) from Group A ($10^3$ $TCID_{50}$), 66% (4/6) from group C ($10^4$ $TCID_{50}$) and 33% (2/6) from Group E ($10^5$ $TCID_{50}$) survived challenge.

Statistical Analysis of Results

Figure 22A:
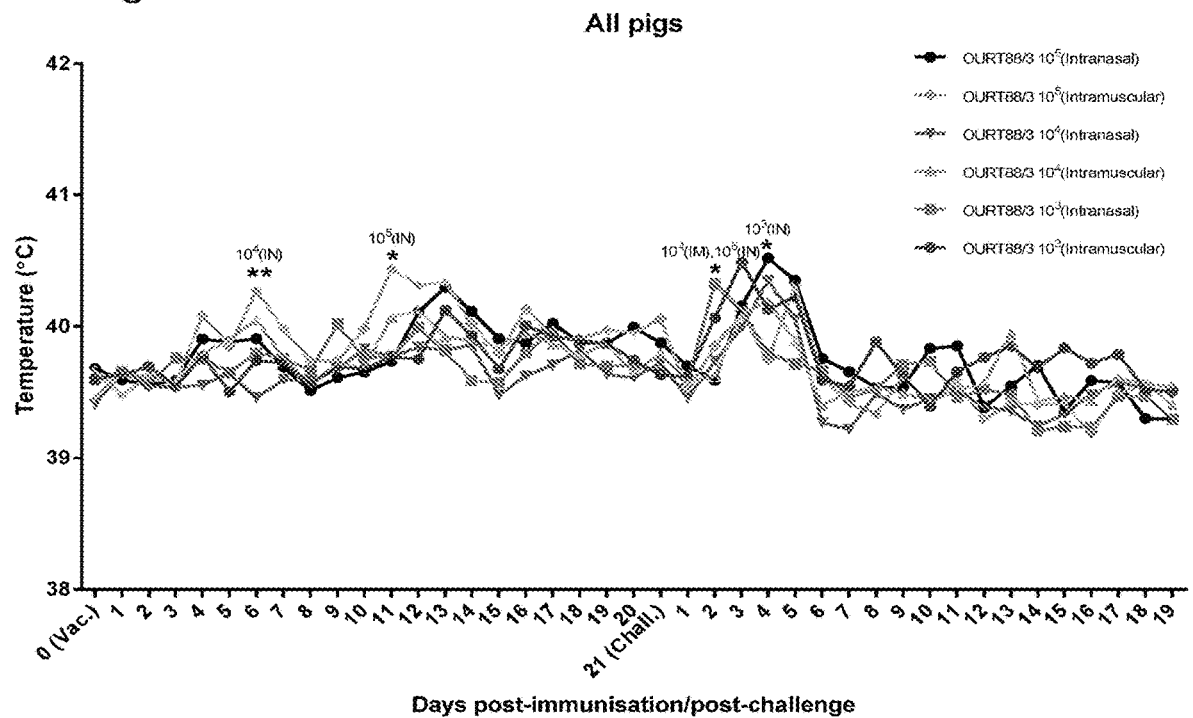
Figure 22B:
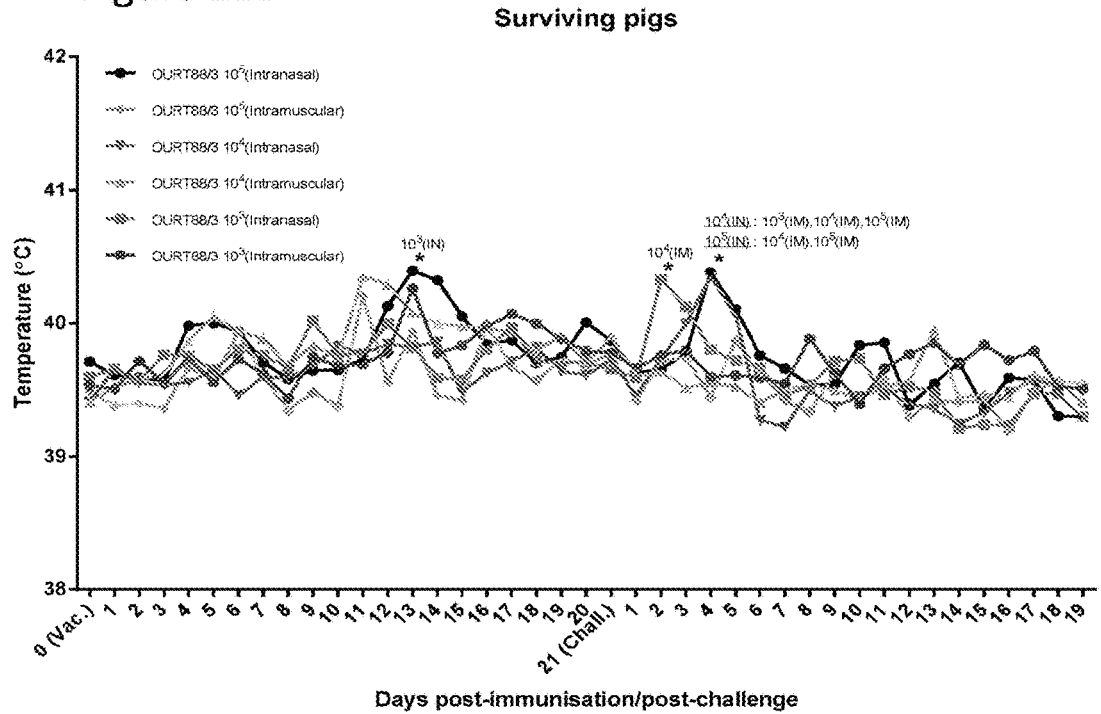
Figure 22C:
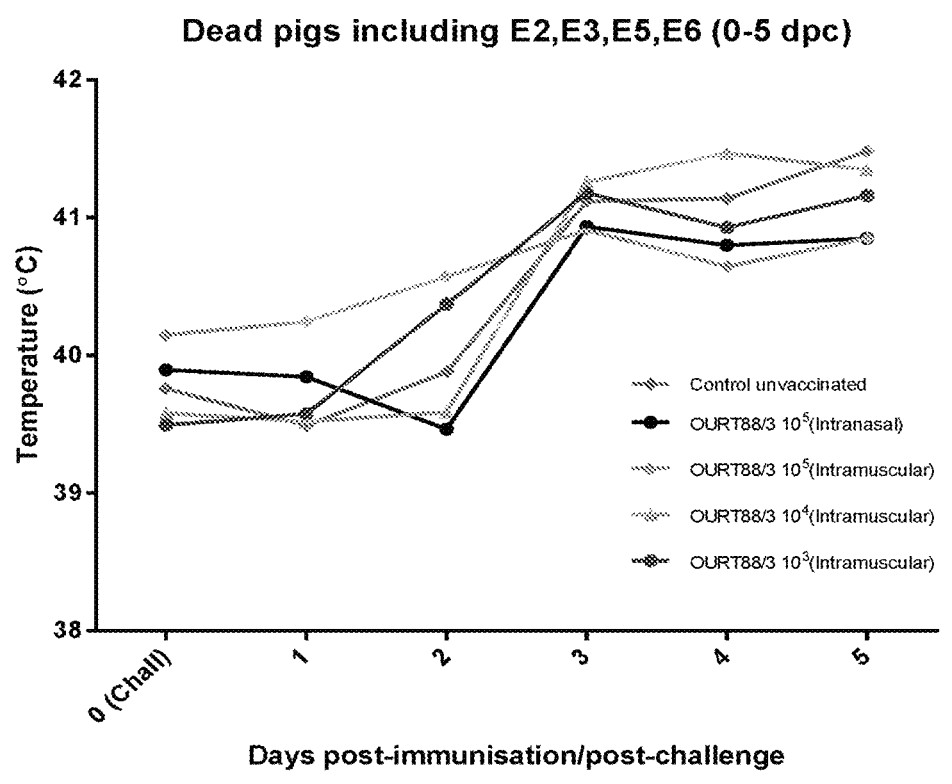
Figure 23A:
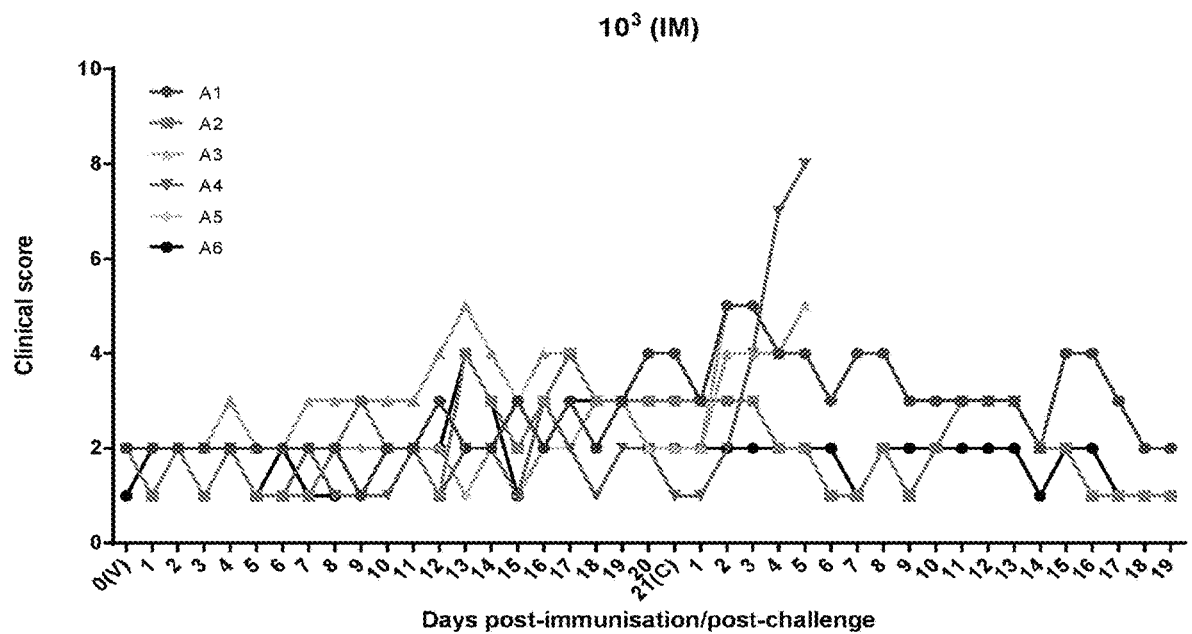
Figure 23B:
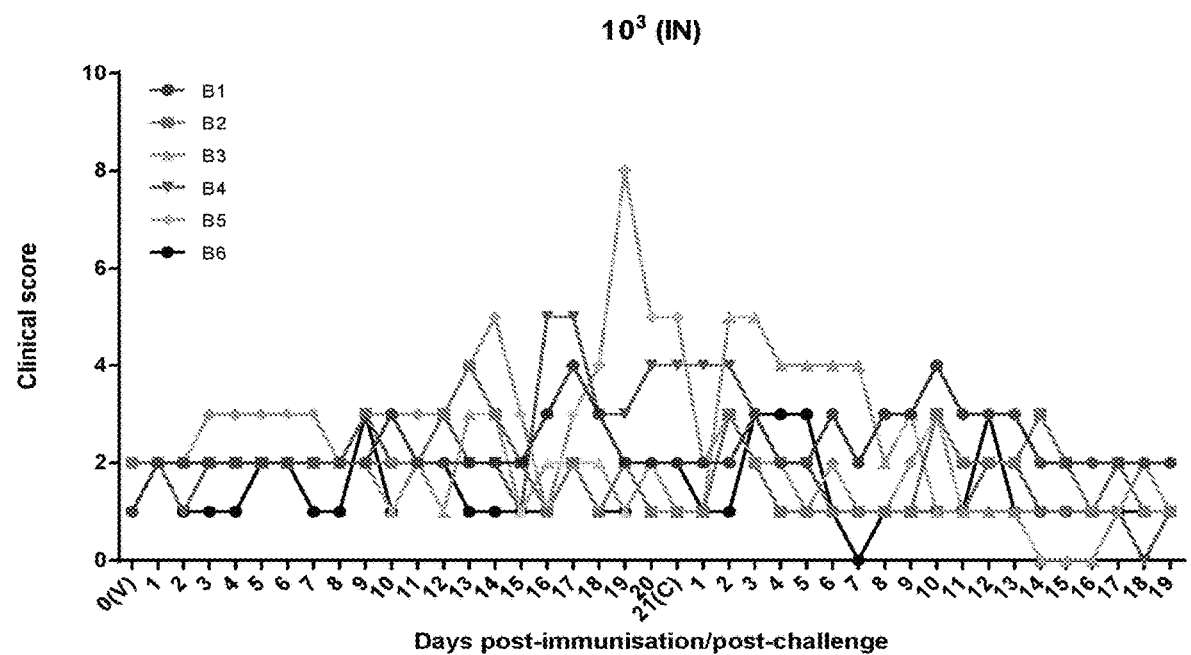
Figure 23E:
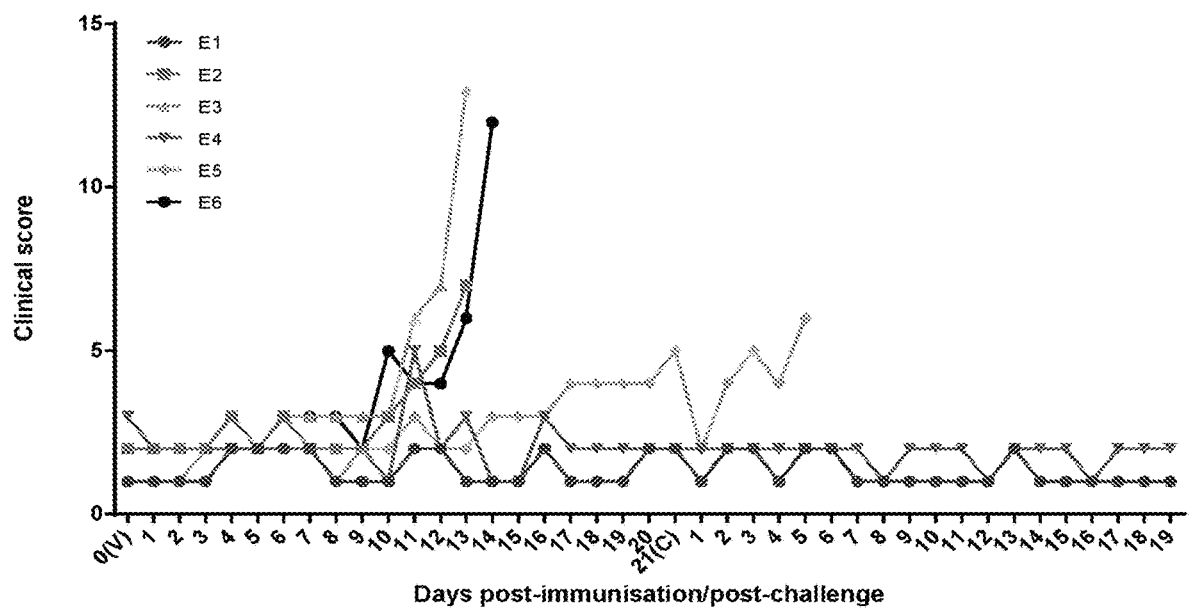
Figure 23F:
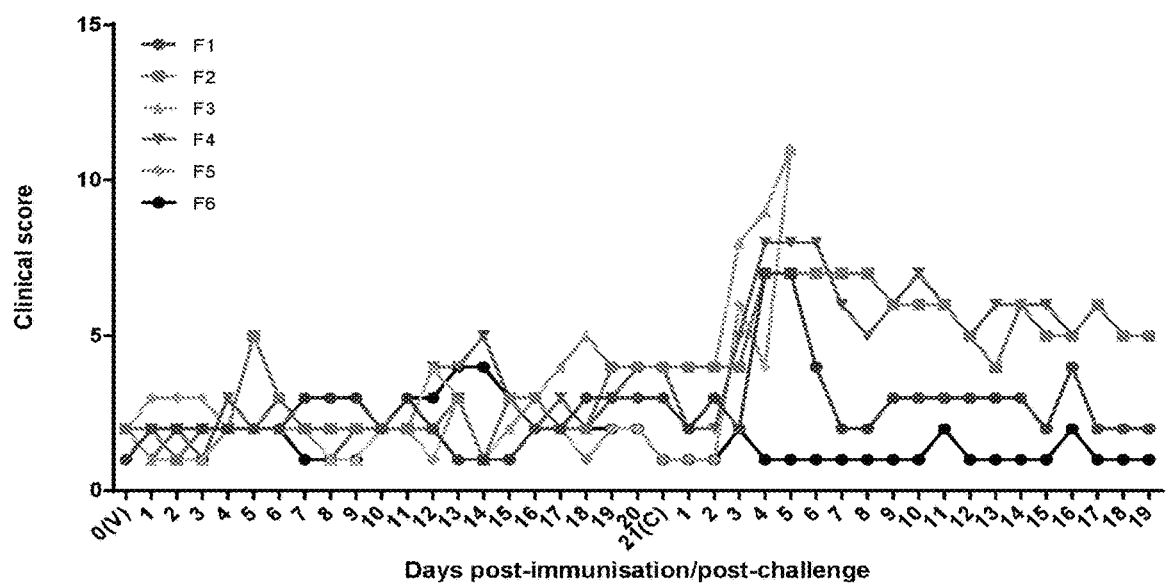
Figure 23G:
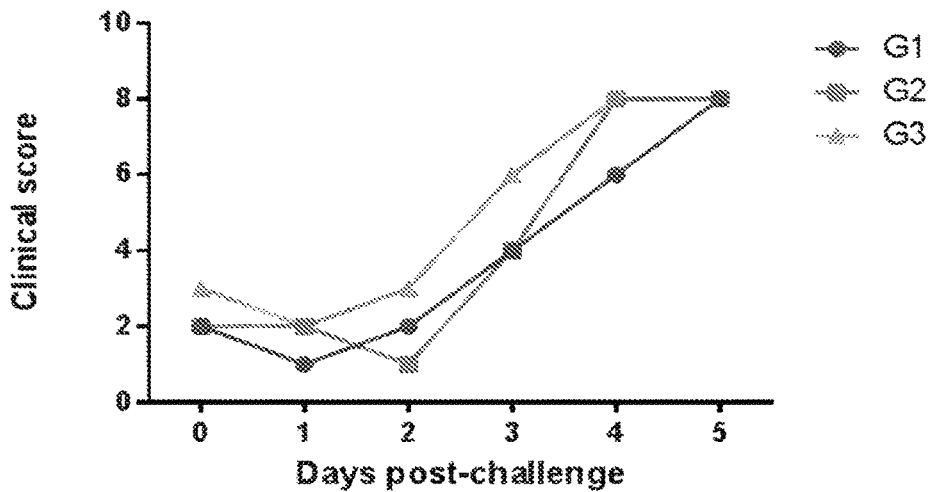
Figure 23H:
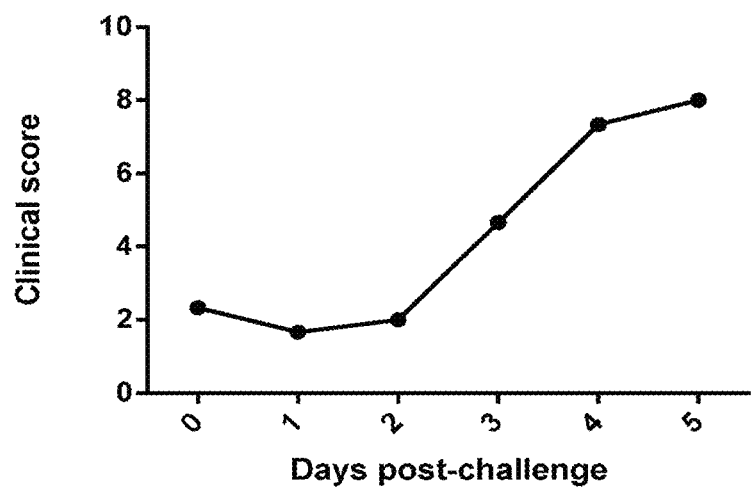
FIG. 23H control unvaccinated group.
Figure 24A:
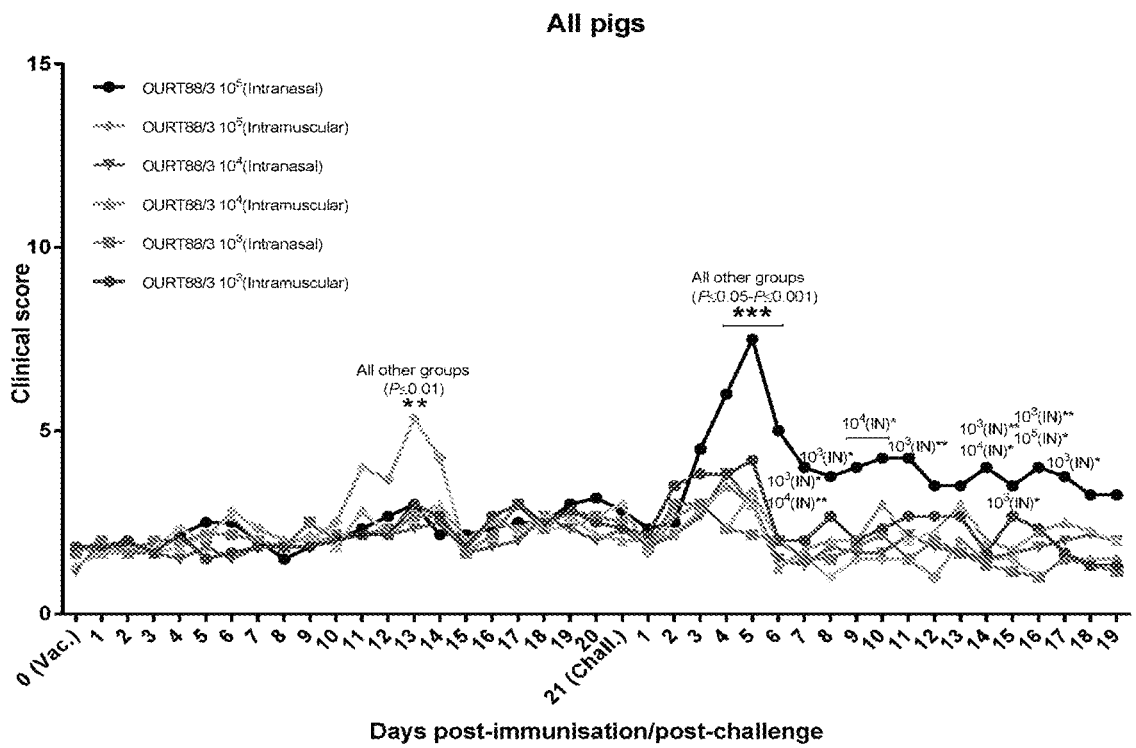
FIG. 24A-C—Mean clinical scores of all pigs in Example 6 groups A to F after immunisation and challenge are shown in panel A (FIG. 24A). Panel B (FIG. 24B) shows mean temperatures of surviving pigs in groups A to F and panel C (FIG. 24C) temperatures of non-survivors.
Figure 24B:
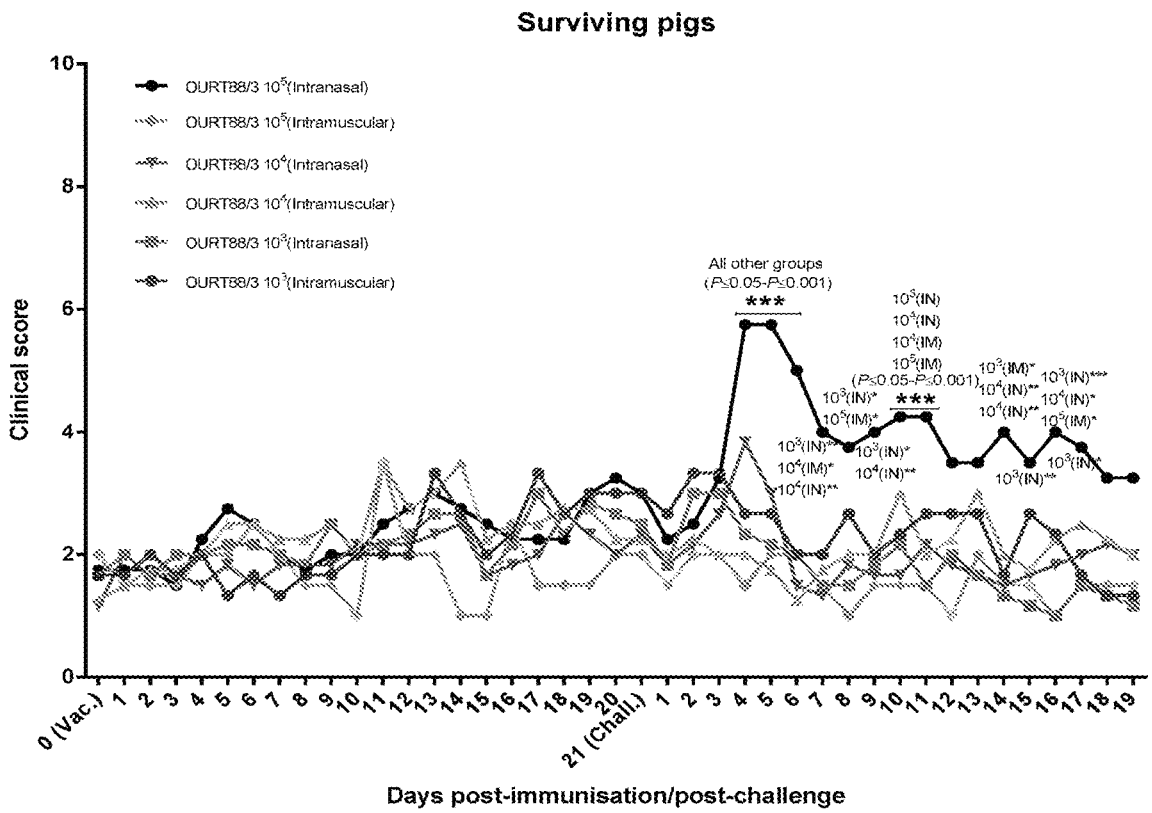
Figure 24C:
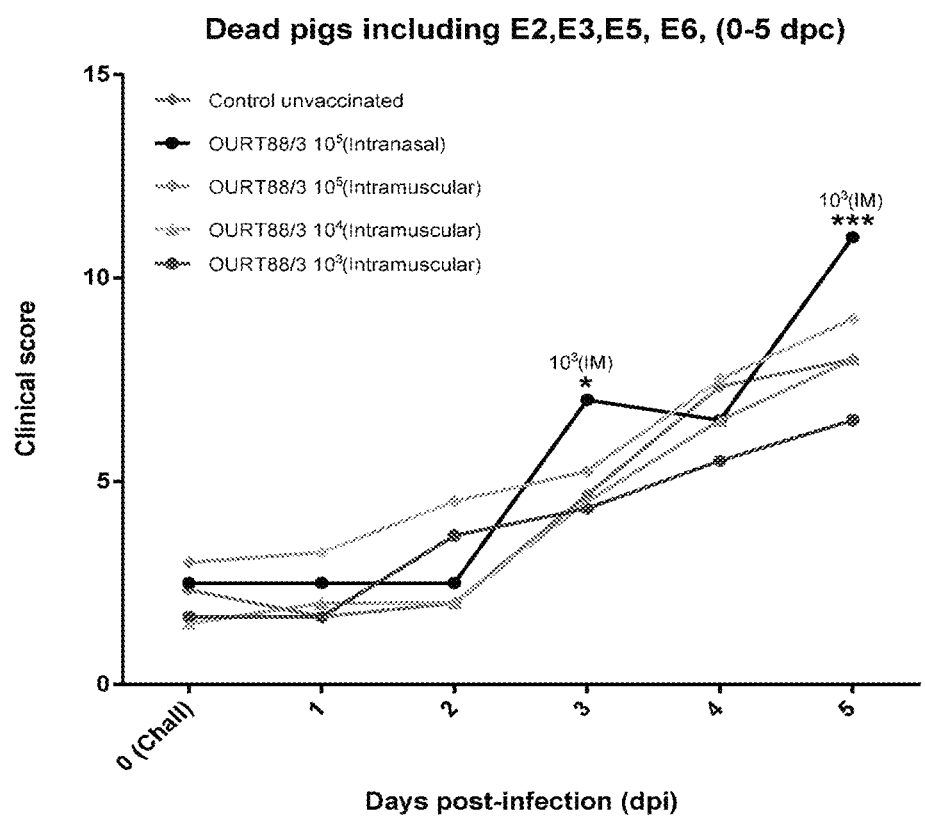

Comparative statistical analysis of clinical scores (5 days before death) developed by pigs that died or were euthanized inside each experimental group (including pigs dead before challenge in group E and non-immunised control pigs), revealed similar kinetics as well as non-significant differences in reached temperatures among groups (FIG. 22). In addition, kinetics of clinical scores was similar, significant differences appeared just between pigs dead in group F (IN, $10^5$) and group A (IM, $10^3$) (FIG. 24). On the other hand, statistical analysis of clinical scores in pigs that survived revealed that after challenge, surviving pigs in group F (IN, $10^5$) showed significant differences in clinical scores with respect to surviving pigs including in other groups until the end of the study (FIG. 24).

Figure 25A:
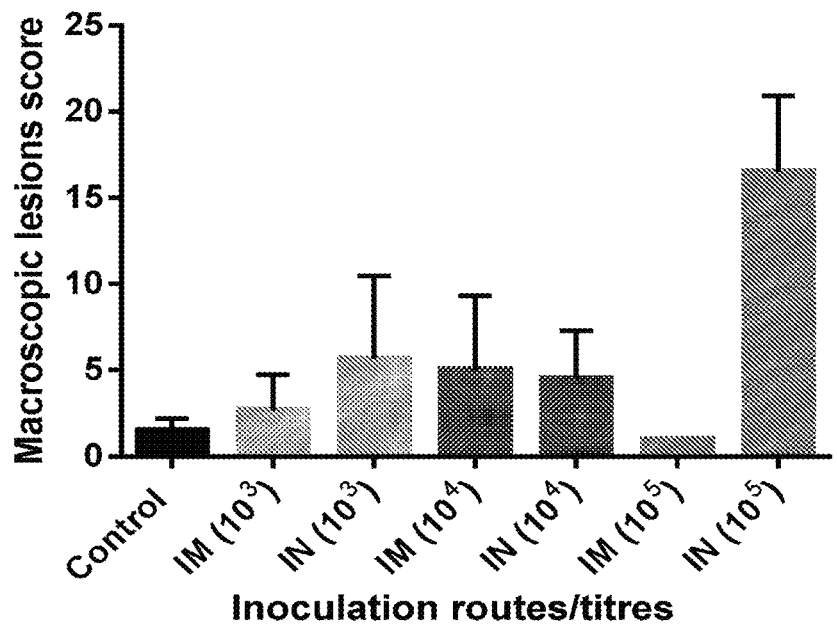
FIG. 25A-C —Scoring of lesions observed at necroscopy for different groups of pigs in Example 6. Mean scores for numbers of lesions observed in different groups from A to F are shown. Panel A (FIG. 25A) shows scores of macroscopic lesions, Panel B (FIG. 25B) of pulmonary lesions and Panel C (FIG. 25C) of skin and musculoskeletal lesions FIG. 26—IFN-β mRNA induction by different ASFV isolates in primary porcine alveolar macrophages.
Figure 25B:
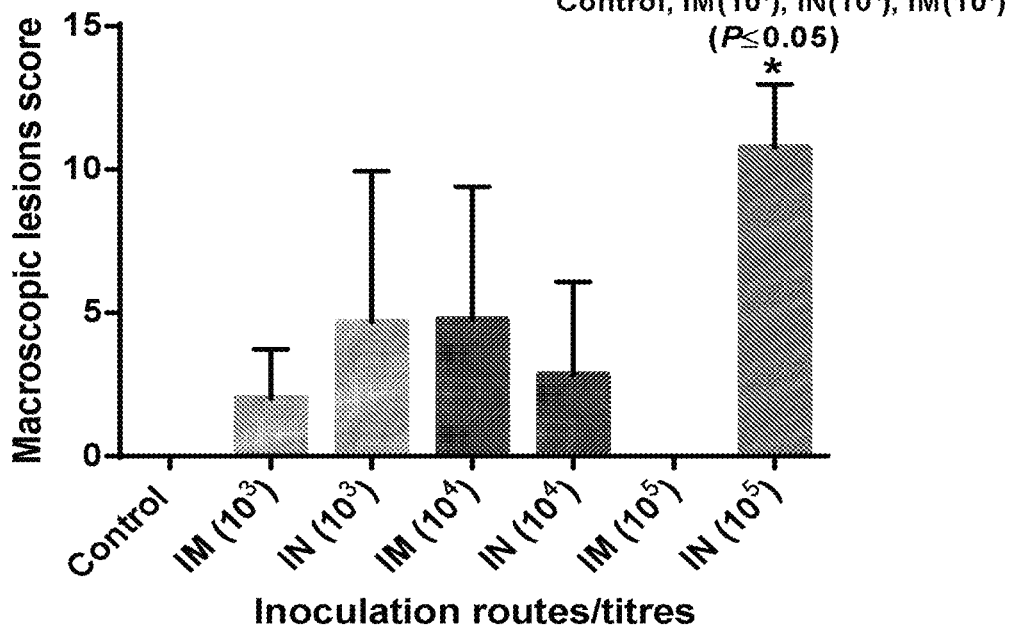
Figure 25C:
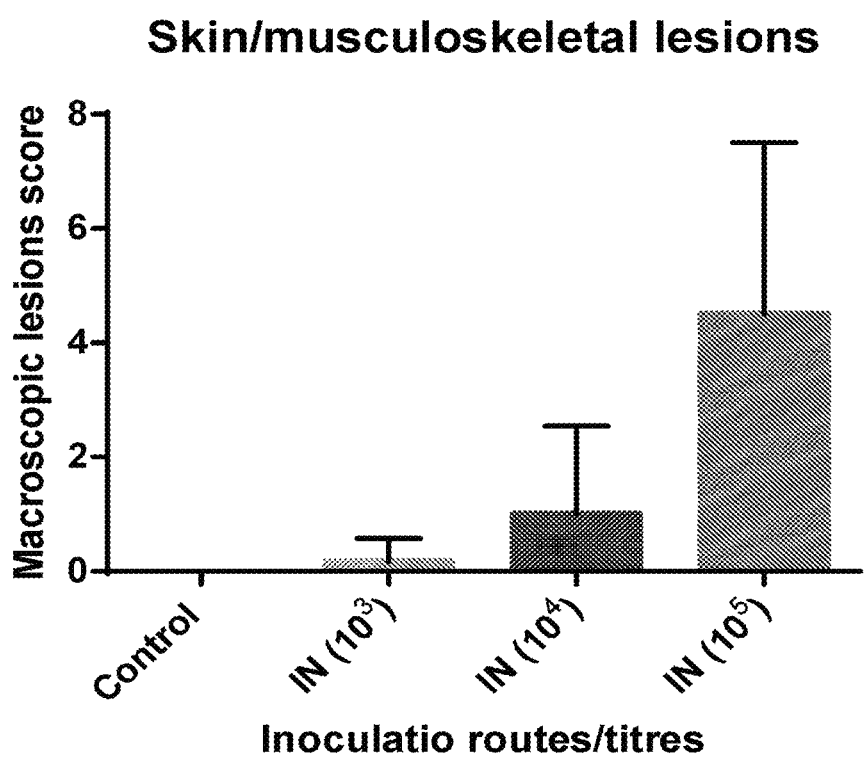
Figure 29A:
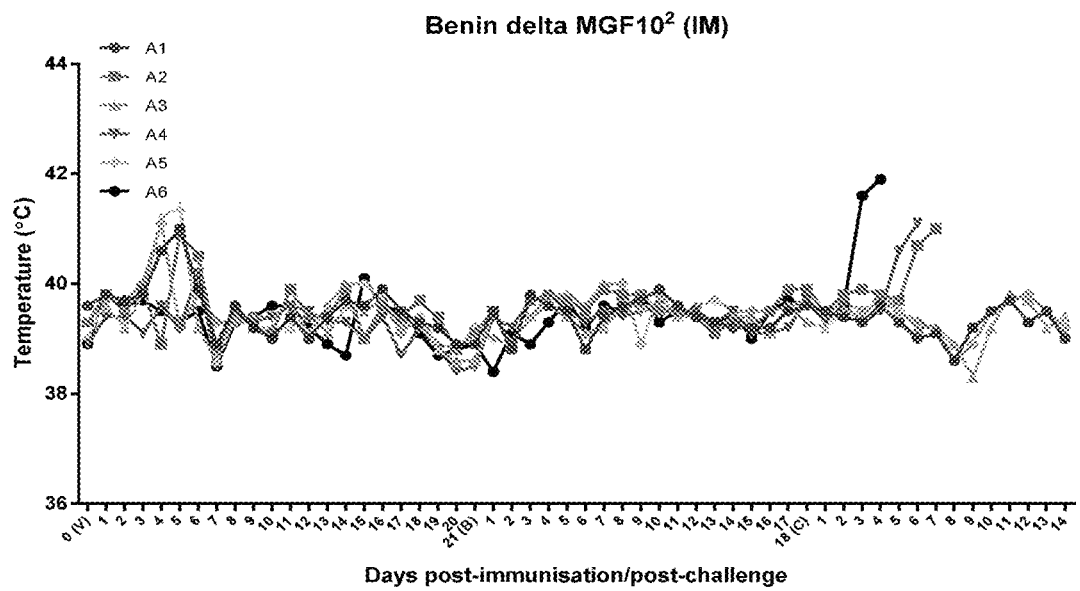
FIG. 29—Temperatures of pigs immunised with BeninΔMGF at $HAD_{50}$ doses of $10^2$ (FIG. 29A), $10^3$ (FIG. 29B) and $10^4$ (FIG. 29C) using the IM route, $10^3$ $HAD_{50}$ using the intranasal route (FIG. 29D) and BeninΔDP148R at 10 $HAD_{50}$ using IM route (FIG. 29E), on different days post-immunisation and challenge and of control group (FIG. 29F) after challenge.
Figure 29B:
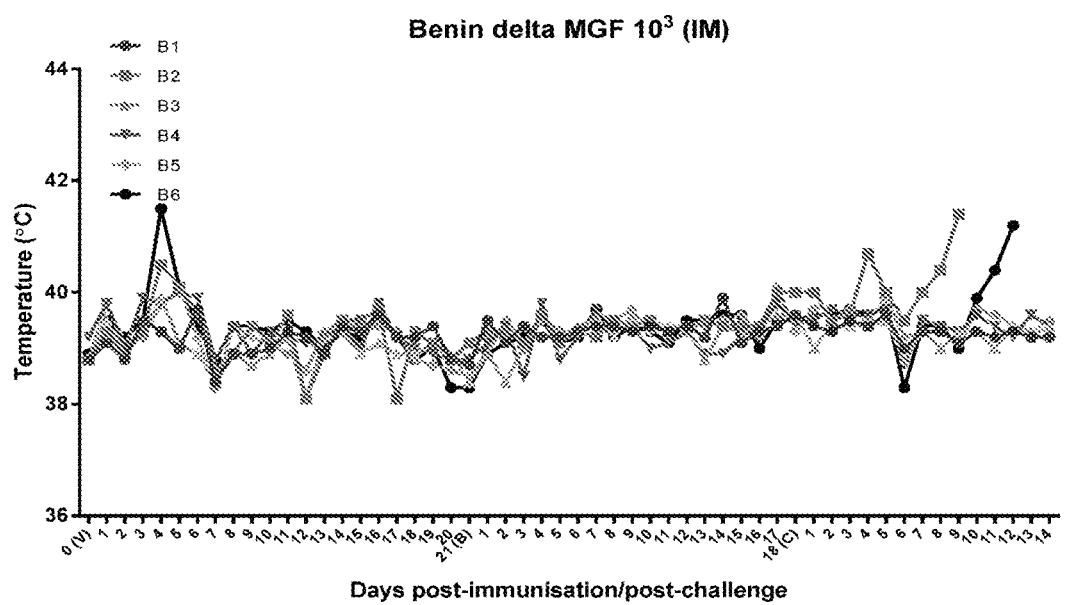
Figure 29E:
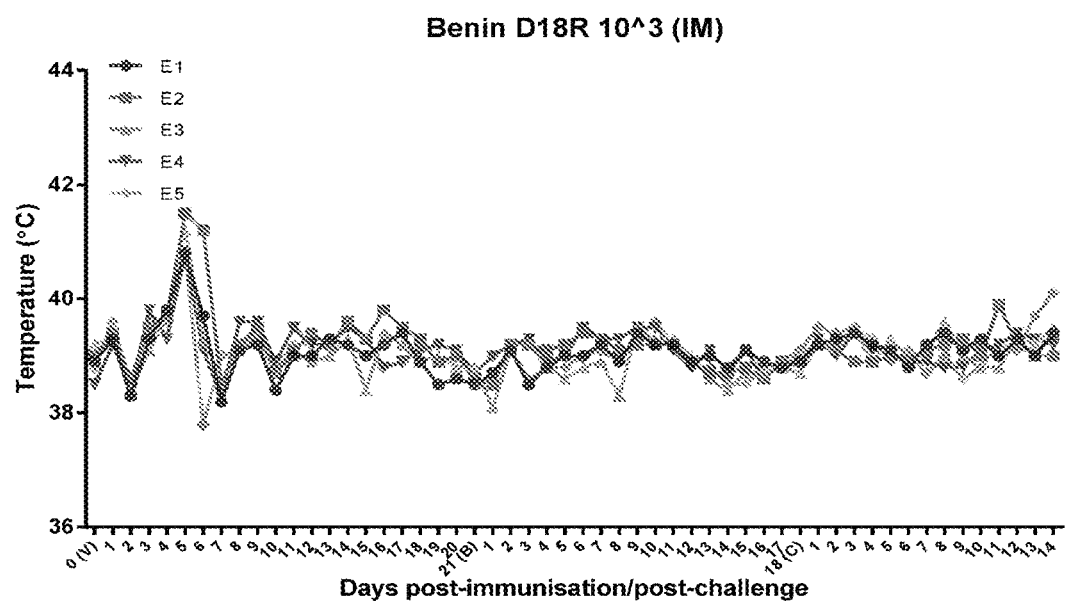
Figure 29F:
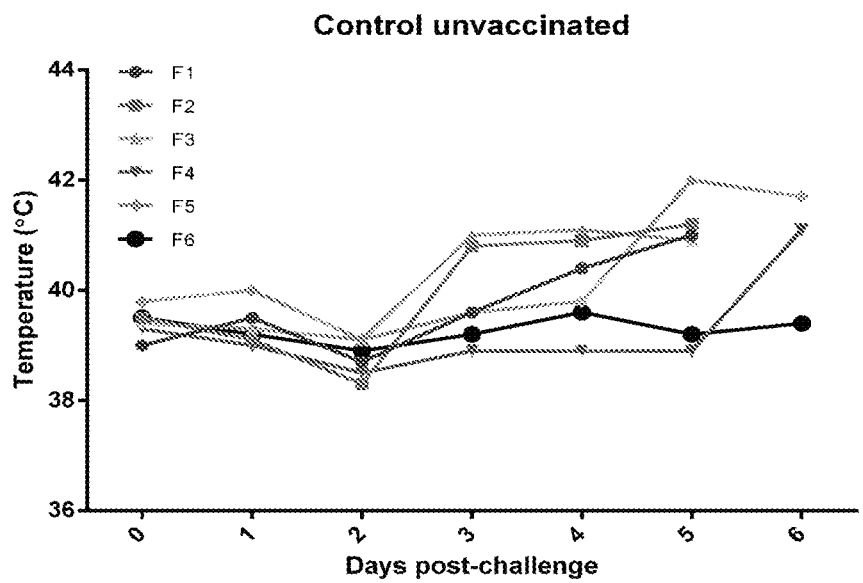
Figure 30A:
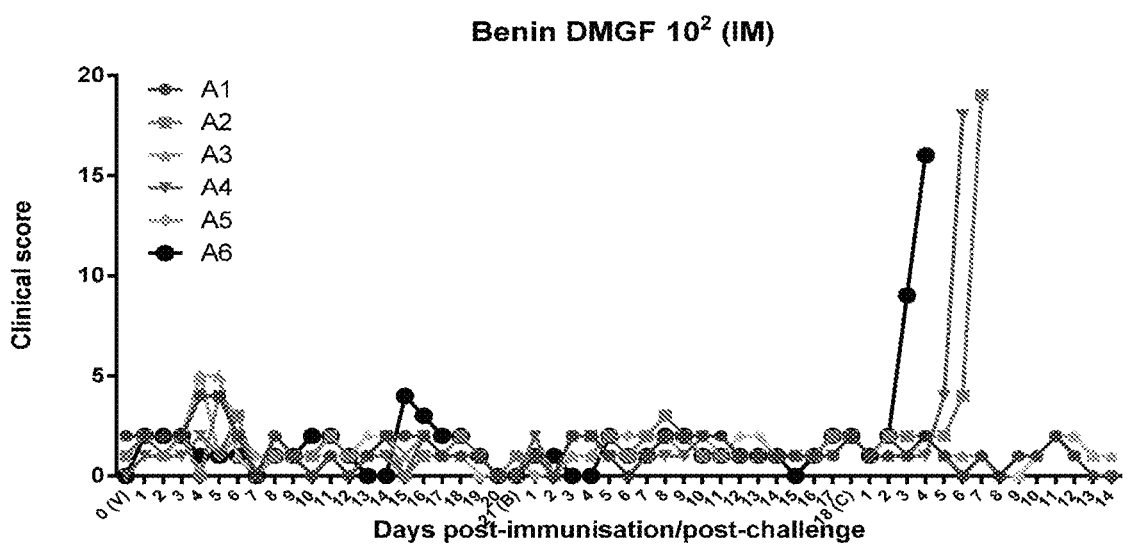
Figure 30B:
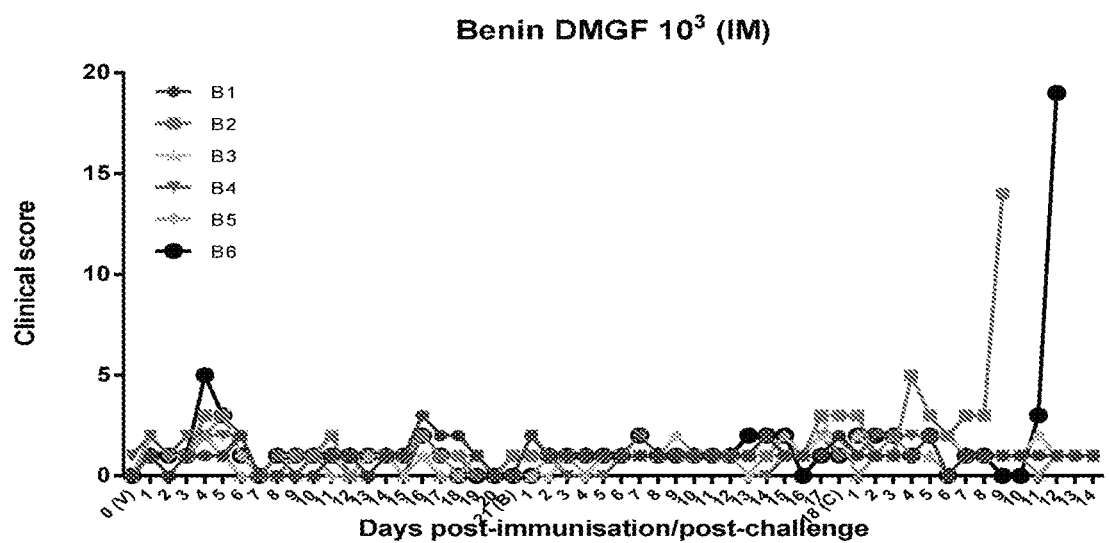
Figure 30C:
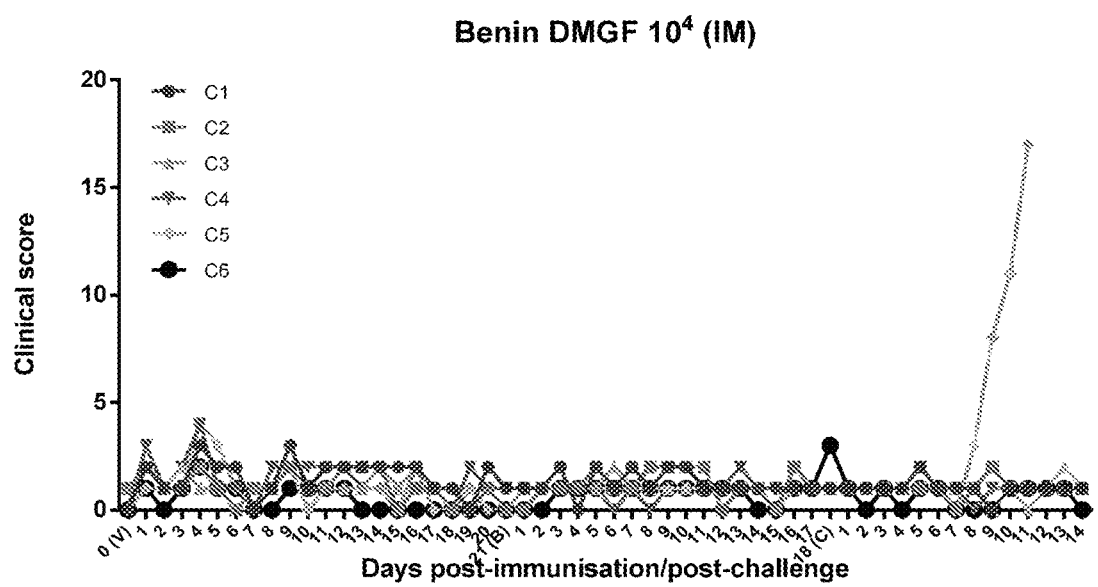
Figure 30D:
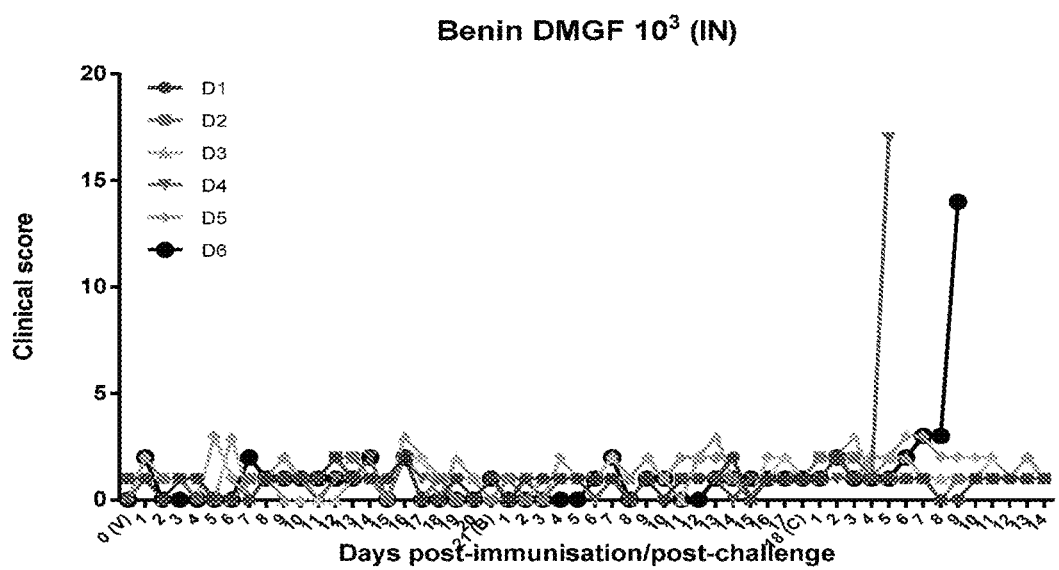
Figure 30E:
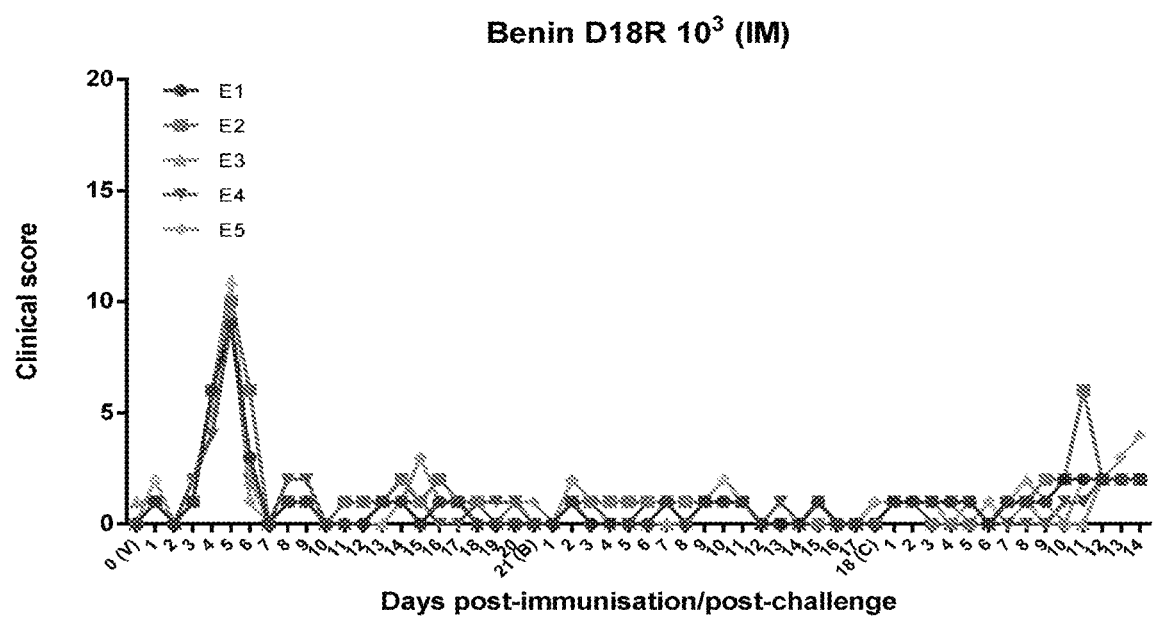

During macroscopic evaluation of surviving pigs, lesions were mainly observed in cardiorespiratory system, skin and musculoskeletal system. In general, surviving pigs immunised intramuscularly (9 pigs in all) displayed no lesions or minimal pulmonary lesions (6/9 pigs), while surviving pigs immunised intranasally (16 pigs in all) showed cardiorespiratory lesions (12/16 pigs) as well as injuries in skin and joints (7/16 pigs). In this sense, while lesions were moderate in surviving pigs immunised intranasally with $10^3$ and $10^4$ (groups B and D), surviving pigs inoculated intranasally with $10^5$ (group F) displayed the most intense cardiorespiratory and musculoskeletal injuries (fibrinous pleuritis, fibrinonecrotic pleuropneumonia, fibrinous pericarditis and serofibrinous/purulent periarthritis), cardiorespiratory lesions being compatible with the presence of secondary bacterial infections. Statistical analysis of macroscopic lesion scores confirmed the significant differences among surviving pigs in group F (IN, $10^5$) and the other groups of surviving animals (FIG. 25).

DISCUSSION

These results have demonstrated a complete protection (100%) in pigs immunised intranasally with $10^3$ and $10^4$ $TCID_{50}$/ml of low virulent ASFV isolate OUR T88/3. Pigs displayed minimal and transient adverse clinical reactions before and after challenge with the virulent ASFV isolate OUR T88/1 as well as mild lesions in lungs, associated to secondary bacterial infections, and joints mainly. We predict from our results that a lower dose (eg $10^2$ $TCID_{50}$) may also induce high levels of protection against lethal challenge.

However, in both the group of pigs immunised intranasally with $10^5$ $TCID_{50}$/ml and in all groups immunised intramuscularly, the rate of protection conferred was lower. The lowest survival rates were observed in pigs immunised intramuscularly with $10^5$ $TCID_{50}$/ml, where 3 of the 6 immunised pigs (E2, E3 and E6) died before challenge. The results show that intranasal immunisation of pigs with live attenuated ASFV vaccines is an alternative to the previously reported intramuscular route. Intranasal immunisation induced fewer clinical signs before challenge compared to the intramuscular route and a higher percentage of pigs were protected.

Example 7—Immunisation with BeninΔMGF by Different Routes

This involved testing delivery of the gene deleted attenuated ASFV BeninΔMGF at three different doses using the IM route ($10^2$, $10^3$, $10^4$ $HAD_{50}$) and by one dose ($10^3$ $HAD_{50}$) using the intranasal route and challenge with parental virulent virus.

Materials and Methods

The experiments were carried out in SAPO-4 biocontainment facilities at The Pirbright Institute. All animal experiments were carried out under UK Home Office License number 70/7198 and complied fully with the regulated procedures from the Animals (Scientific Procedures) Act 1986.

Large White Landrace crossbred female piglets in good health, average weight 15-20 kg, from a high health herd were used. After a 5-day acclimatisation period, three groups of six pigs each were immunised intramuscularly (IM) with 1 ml containing $10^2$ (group A), $10^3$ (group B) and $10^4$ (group C) $HAD_{50}$ of attenuated ASFV gene deleted BeninΔMGF strain respectively. An additional group of six pigs were immunised intranasal (IN), using a mucosal atomization device, with 1 ml per nostril containing $10^3$ BeninΔMGF (group D). Three weeks later all immunised groups were boosted with the same dose of virus by the same route. After a further 19 days pigs in groups A to D, together with a control group (group F) containing six non-immunised pigs, were challenged intramuscularly with 1 ml containing $10^4$ $TCID_{50}$/ml of the parental virulent ASFV isolate Benin 97/1. This control group was housed separately, while the other pigs were allocated in the same isolation room separated by 1 m high partition as follows: room 1 (groups A and B), room 2 (groups C and D).

Sampling, Clinical and Post-Mortem Examination.

Immunisation day was defined as day 0 (0 dpi). Rectal temperatures and clinical signs were monitored daily prior to immunisation and throughout the study, following a clinical score previously reported (King et al., 2011). EDTA blood and serum samples were collected from all pigs prior to virus immunisation (0 dpi), after immunisation (at 2, 4, 7, 10, 14 and 21 dpi) boost and after challenge (at 3, 5, 7, 14 and 19 dpc).

A post-mortem examination also was carried out in order to evaluate gross lesions of dead pigs or euthanized during the experiment upon reaching a predetermined humane endpoint, as well as at the end of the experiment. Macroscopic lesions were evaluated in accordance with the standardized pathological framework of ASFV infections (Galindo-Cardiel et al., 2013). The humane end point was determined in accordance with the welfare regulations specified in the UK Home Office License, so that pigs with a rectal temperature over 40.5° C. for three consecutive days, or showing three or more clinical signs of disease combined on a single day, were euthanized. Euthanasia was conducted by intravenous injection of pentobarbital sodium.

Results

Pigs were immunised and observed daily for clinical signs including temperatures. Results are shown in FIG. 29. Of the pigs in groups A ($10^2$) and B ($10^3$) 4/6 developed a transient low fever for 1 or 2 days from day 4 or 5 post-immunisation. In group C (IM $10^4$) 3/6 pigs developed a transient low fever for 1 or 2 days. In group D (IN $10^3$) 1/6 pigs developed a low transient fever at day 5 post-immunisation. No other clinical signs were observed.

The results confirm that increasing the dose of BeninΔMGF does not increase clinical signs post-immunisation by the IM route. FIG. 29 shows that minimal clinical signs were observed in these and remaining pigs following the boost and until after challenge. Following challenge several pigs were euthanized because they reached moderate severity end-point (3 days fever above 40.5 or 2 days without eating). These included 3 of the 6 pigs from the group immunised with $10^2$ IM, 2 pigs immunised with $10^3$ IM, 1 pig immunised with $10^4$ IM and 2 pigs immunised with $10^2$ IN. At post-mortem, lesions were not observed in any group except for 1 pig from group BeninΔMGF $10^2$ IM which had a single lung lesion.

Figure 31:
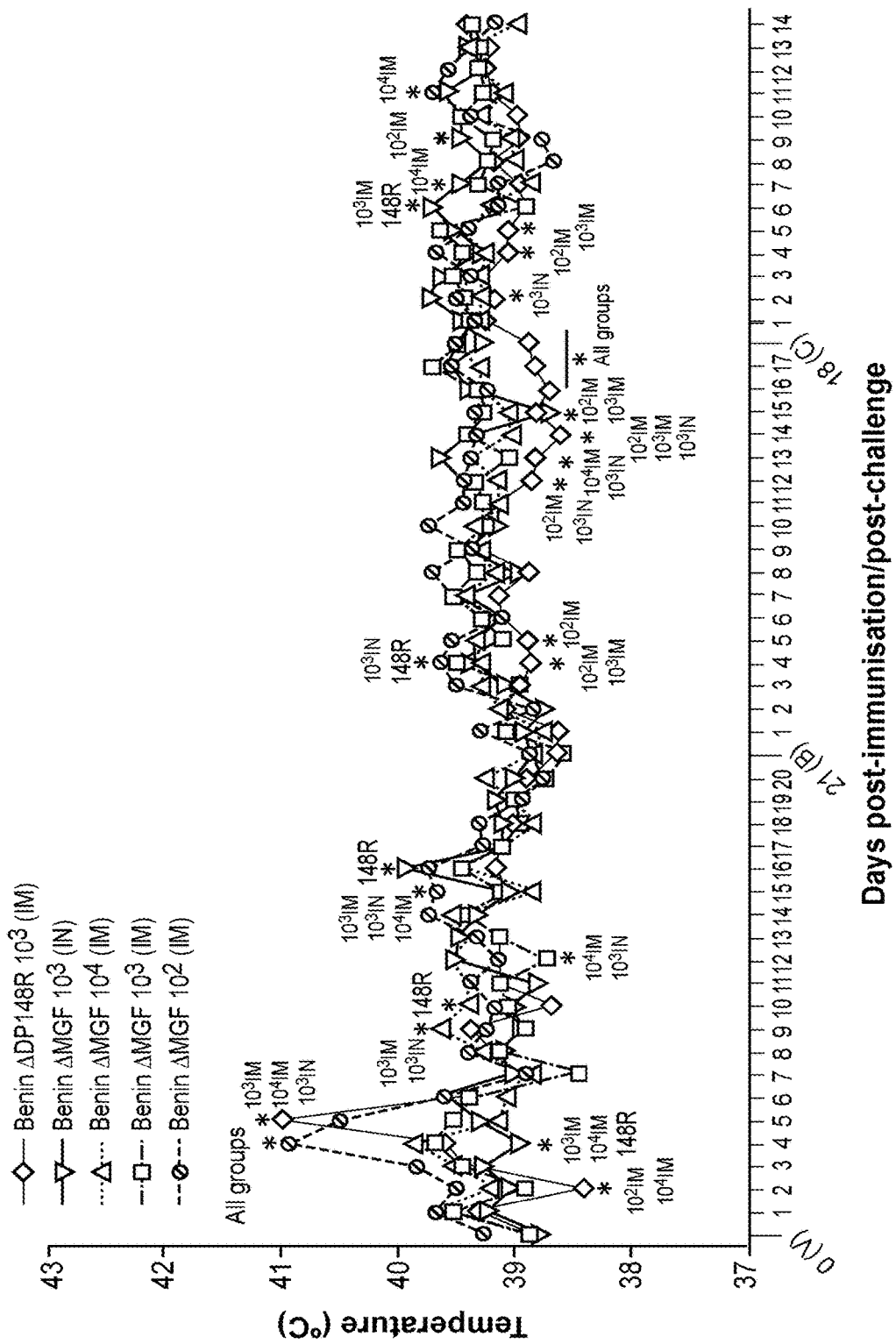
FIG. 31—Mean temperatures of all pigs in groups A to E as described for FIG. 29 after immunisation and challenge.

A comparison of mean temperatures of the different groups (FIG. 31) showed statistically significant differences between the group immunised with BeninΔMGF $10^2$ IM and other groups post-immunisation at day 4 (higher compared to all other groups), day 15 (higher compared to BeninΔMGF $10^3$ IM, $10^3$ IN and $10^4$ IM). Post-boost statistically significant differences were observed between BeninΔMGF $10^2$ IM (higher compared to BeninΔMGF $10^3$ IN and BeninΔDP148R). At day 12 post-challenge pigs immunised with BeninΔMGF $10^2$ IM had a significantly higher temperature compared to pigs immunised with BeninΔMGF $10^4$ IM.

Pigs immunised with BeninΔMGF $10^3$ IN had significantly different temperatures at days post-immunisation 4 (lower compared to BeninΔMGF $10^3$ IM, $10^4$ IM and BeninΔDP148R), post-immunisation day 6 (higher compared to BeninΔDP148R), day 11 post-challenge (higher compared to BeninΔMGF $10^4$ IM). Pigs immunised with BeninΔMGF $10^4$ IM had statistically significant temperatures at day 8 post-immunisation (higher compared to BeninΔMGF $10^3$ IM, $10^2$ IN) and day 9 post-immunisation (higher compared to BeninΔDP148R). Pigs immunised with BeninΔMGF $10^3$ IM had significantly different temperatures at day 12 post-immunisation (lower compared to BeninΔMGF $10^4$ IM and $10^3$ IN).

Figure 32:
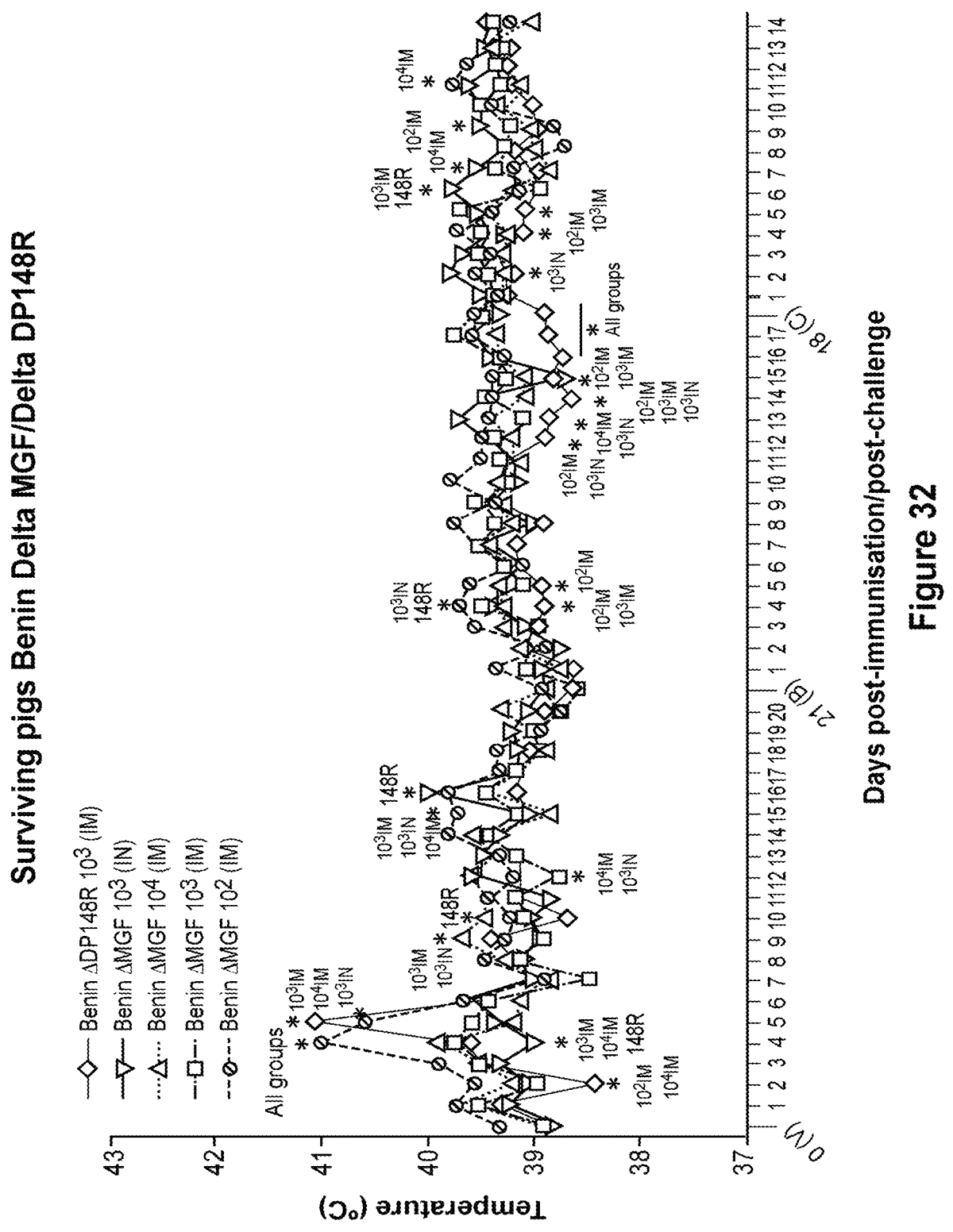

A comparison of mean clinical scores of the different groups (FIG. 32) showed statistically significant differences between the group immunised with BeninΔMGF$10^2$ IM and other groups post-immunisation at day 2 (higher than BeninΔMGF $10^3$ IM, $10^3$ IN, BeninΔDP148R), day 4 (higher than BeninΔMGF $10^3$ IM, $10^4$ IM, $10^3$ IN) and day 5 (lower than BeninΔDP148R, higher than BeninΔMGF $10^3$ IM, $10^3$ IN).

In conclusion, BeninΔMGF $10^2$ IM showed significantly higher clinical scores and lower temperatures than other groups post-immunisation.

Example 8—IFN-β mRNA Induction by Different ASFV Isolates

Porcine alveolar macrophages were infected with ASFV isolates indicated at multiplicity of infection 3 (Benin 97/1, BeninΔMGF, OURT88/3) or were mock-infected. At different times post-infection (2, 4, 6, 8, 10, 12, 16, 20 hours) RNA was harvested from infected cells and levels of mRNA for IFN-β RNA, GAPDH and ASFV B646L gene (VP72) were measured by quantitative reverse transcriptase PCR. FIG. 26 panel A shows levels of IFN-β compared to control housekeeping gene GAPDH. Panel B shows levels of mRNA for ASFV B646L (VP72) gene.

The deletion mutant BeninΔMGF has a deletion or interruption of 6 members of MGF360 and 4 members of MGF 505 from a region close to the left end of the Benin 97/1 genome. Deletion of these genes increases the induction of IFN-β mRNA in macrophages infected with BeninΔMGF360 compared to parental virulent virus in which IFN-β mRNA was barely detected (see FIG. 26). Type I IFNs induce expression of IFN-stimulated genes which are involved in activation of host innate and adaptive immune response pathways and in creating an antiviral state. Our hypothesis is that induction of type I IFN is important for attenuation of virulent ASFV and induction of a protective immune response.

Example 9—Deletion Mutant BeninΔDP148R

A single gene, DP148R, was deleted from a region close to the right end of the virulent Benin97/1 genome. To achieve this a 529 bp fragment from the left and 740 bp fragment from the right regions flanking the MGF36018R gene were amplified by PCR. FIG. 27 shows the primers used to amplify the left flanking region (360-18RFlankL) and those to amplify the right flanking region (360-18RFlankR). The sequences amplified are between these primers. Shaded in grey is the sequence of the MGF360-18R gene which was deleted from the ASFV genome. The start and stop codons are shown in bold. The flanking regions were cloned either side of a reporter gene consisting of the β-Glucorinidase (β-GUS) gene downstream from the ASFV VP72 promoter. This plasmid was transfected into pig macrophages infected with the Benin 97/1 isolate. Progeny virus was tested for expression of the i-GUS gene and recombinant viruses in which the F-GUS gene replaced the MGF360-18R gene was isolated by limiting dilution. The deletion of the gene and location of the insertion was confirmed by PCR analysis using primers that were from the ASFV genome outside of the regions cloned in the transfer plasmid (see FIG. 27).

Deletion of the DP148R Gene does not Reduce Virus Replication in Macrophages

Replication of the BeninΔMGF36018R virus strain in porcine macrophages was compared with parental Benin 97/1 virus. Porcine alveolar macrophages were infected at a multiplicity of 3 and at different times post-infection (0, 24, 48, 72, 96 hours) virus from cells and supernatants was harvested and titrated using porcine alveolar macrophages. The results (FIG. 28) showed that deletion of the MGF360 18R gene did not reduce virus replication in macrophages.

Deletion of the DP148R Gene Attenuates ASFV in Pigs

A group of 5 male large white/landrace crossbred pigs (15-20 kg) were immunised intramuscularly with $10^3$ HAD$_{50}$ BeninΔDP148R and observed for clinical signs. All 5 pigs displayed transient clinical signs for 1 or 2 days at days 4 or 5 post-immunisation. These signs included transient fever, loss of appetite and lethargy.

Pigs were boosted with the same dose of virus by the same route at day 21 post-immunisation and were challenged with virulent Benin97/1 in parallel with control non-immunised pigs at day 39 post-immunisation. No further clinical signs were observed following the boost and all pigs survived challenge (terminated at 19-21 days post-challenge). No lesions were observed at post-mortem.

A comparison of mean temperatures of the different groups (FIG. 31) showed statistically significant differences between the group immunised with BeninΔDP148R and other groups post-immunisation at day 2 (lower compared to groups BeninΔMGF $10^2$ IM and $10^4$ IM) and day 5 (higher compared to groups BeninΔMGF $10^3$ IM, $10^4$ IM and $10^3$ IN). At days post-boost statistically lower temperatures were observed between BeninΔDP148R and other groups: 5, (BeninΔMGF10 IM, $10^3$ IM) 6 (BeninΔMGF $10^2$ IM), 12 (BeninΔMGF $10^2$ IM, $10^3$ IN), 13 (BeninΔMGF $10^4$ IM, $10^3$ IN), 14 (BeninΔMGF $10^2$ IM, $10^3$ IM, $10^3$ IN), 15 (BeninΔMGF $10^2$ IM, $10^3$ IM), 17-19 (BeninΔMGF all groups). Post-challenge significantly lower temperatures were observed between pigs immunised with BeninΔDP148R and other immunised groups at day 3 (BeninΔMGF $10^3$ IN), 5 ($10^2$ IM), 6 ($10^3$ IM).

A comparison of mean clinical scores of the different groups (FIG. 32) showed statistically significant differences between the group immunised with BeninΔDP148R and other groups post-immunisation at day 4 (higher than BeninΔMGF $10^2$ IM, $10^3$ IM, $10^3$ IN), day 5 (BeninΔMGF $10^2$IM, $10^3$IM, $10^3$IN, $10^4$IM), day 6 (BeninΔMGF $10^3$IM, $10^3$IN, $10^4$IM) and day 6 (BeninΔMGF $10^3$IM, $10^3$IN, $10^4$IM).

In conclusion, BeninΔDP148R demonstrated significantly higher clinical scores and lower temperatures than the other groups post-mortem, and no lesions at post-mortem.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in virology, molecular biology or related fields are intended to be within the scope of the following claims.

The invention claimed is:

1. A vaccine comprising an attenuated African Swine Fever (ASF) virus which lacks a functional version of the following genes:
   multigene-family 360 genes 9L, 10L, 11 L, 12L, 13L and 14L; and
   multigene-family 505 genes 1R, 2R, 3R and 4R.

2. The vaccine according to claim 1, which comprises an ASF virus wherein the following genes are at least partially deleted:
   multigene-family 360 genes 10L, 11 L, 12L, 13L and 14L; and
   multigene-family 505 genes 1R, 2R and 3R.

3. The vaccine according to claim 2, which comprises an ASF virus wherein the following genes are deleted:
   multigene-family 360 genes 10L, 11 L, 12L, 13L and 14L; and
   multigene-family 505 genes 1R, 2R and 3R.

4. The vaccine according to claim 1, which comprises an ASF virus wherein the following genes are interrupted:
   multigene-family 360 gene 9L; and
   multigene-family 505 gene 4R.

5. The vaccine according to claim 1 in which the remainder of the ASF virus genome corresponds to a genome from a virulent ASFV virus isolate.

6. The vaccine according to claim 1 which when administered to a subject, induces a reduced T cell mediated immune response compared to the immune response induced by virus OURT88/3.

7. The vaccine according to claim 6 which comprises a plurality of attenuated ASF viruses of different genotypes.

8. A method of attenuating an African Swine Fever (ASF) virus, which comprises the step of partially or completely deleting, or interrupting the expression of, the following genes:
   multigene-family 360 genes 9L, 10L, 11 L, 12L, 13L and 14L; and
   multigene-family 505 genes 1R, 2R, 3R and 4R.

9. The method according to claim 8, wherein the following genes are at least partially deleted:
   multigene-family 360 genes 10L, 11 L, 12L, 13L and 14L; and
   multigene-family 505 genes 1R, 2R and 3R.

10. The method according to claim 9, wherein the following genes are deleted:
    multigene-family 360 genes 10L, 11 L, 12L, 13L and 14L; and
    multigene-family 505 genes 1R, 2R and 3R.

11. The method according to claim 9, wherein the following genes are interrupted:
    multigene-family 360 gene 9L; and
    multigene-family 505 gene 4R.

12. Tho A method for preventing African Swine Fever in a subject which comprises the step of administering to the subject an effective amount of a vaccine according to claim 1.

13. The method according to claim 12 wherein the subject is a domestic pig.

14. The method according to claim 12, in which the vaccine is administered following a prime-boost regime.

15. The vaccine according to claim 1 wherein the ASF virus belongs to the Genotype I group.

16. The method according to claim 8 wherein the ASF virus belongs to the Genotype I group.

* * * * *

UNITED STATES PATENT AND TRADEMARK OFFICE
CERTIFICATE OF CORRECTION

PATENT NO. : 11,331,383 B2
APPLICATION NO. : 16/668384
DATED : May 17, 2022
INVENTOR(S) : Charles Abrams et al.

It is certified that error appears in the above-identified patent and that said Letters Patent is hereby corrected as shown below:

On the Title Page

At item (57), Line 8, "Lacks" should be -- lacks --.

In the Claims

At Column 75, Line 16, "11 L," should be -- 11L, --.

At Column 75, Line 22, "11 L," should be -- 11L, --.

At Column 75, Line 27, "11 L," should be -- 11L, --.

At Column 76, Line 16, "11 L," should be -- 11L, --.

At Column 76, Line 20, "11 L," should be -- 11L, --.

At Column 76, Line 25, "11 L," should be -- 11L, --.

At Column 76, Line 32, "Tho A" should be -- A --.

Signed and Sealed this
Seventh Day of February, 2023

Katherine Kelly Vidal
*Director of the United States Patent and Trademark Office*